(12) United States Patent
De Kimpe et al.

(10) Patent No.: US 9,528,109 B2
(45) Date of Patent: *Dec. 27, 2016

(54) METHODS AND MEANS FOR EFFICIENT SKIPPING OF EXON 45 IN DUCHENNE MUSCULAR DYSTROPHY PRE-MRNA

(71) Applicants: Prosensa Technologies B.V., Leiden (NL); Academisch Ziekenhuis Leiden, Leiden (NL)

(72) Inventors: Josephus Johannes De Kimpe, Utrecht (NL); Adriana Marie Rus, Hoofddorp (NL); Gerard Johannes Platenburg, Voorschoten (NL); Judith Christina Theodora Van Deutekom, Dordrecht (NL); Garrit-Jan Boudewijn Van Ommen, Amsterdam (NL)

(73) Assignees: BioMarin Technologies B.V., Leiden (NL); Academisch Ziekenhuis Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,183

(22) Filed: Nov. 14, 2014

(65) Prior Publication Data

US 2015/0073037 A1    Mar. 12, 2015

Related U.S. Application Data

(63) Continuation of application No. 14/200,251, filed on Mar. 7, 2014, now abandoned, which is a continuation of application No. 14/134,971, filed on Dec. 19, 2013, now abandoned, which is a continuation of application No. 14/097,210, filed on Dec. 4, 2013, now abandoned, which is a continuation of application No. 13/094,548, filed on Apr. 26, 2011, which is a continuation of application No. PCT/NL2009/050006, filed on Jan. 13, 2009, which is a continuation of application No. PCT/NL2008/050673, filed on Oct. 27, 2008.

(51) Int. Cl.
| | |
|---|---|
| *C12N 15/11* | (2006.01) |
| *A61K 48/00* | (2006.01) |
| *C07H 21/04* | (2006.01) |
| *C12N 15/113* | (2010.01) |
| *A61K 31/56* | (2006.01) |
| *A61K 31/57* | (2006.01) |
| *A61K 38/17* | (2006.01) |
| *A61K 31/7088* | (2006.01) |
| *A61K 45/06* | (2006.01) |

(52) U.S. Cl.
CPC ............ *C12N 15/113* (2013.01); *A61K 31/56* (2013.01); *A61K 31/57* (2013.01); *A61K 31/7088* (2013.01); *A61K 38/1719* (2013.01); *A61K 45/06* (2013.01); *A61K 48/00* (2013.01); *C12N 2310/11* (2013.01); *C12N 2310/315* (2013.01); *C12N 2310/321* (2013.01); *C12N 2310/3233* (2013.01); *C12N 2320/33* (2013.01)

(58) Field of Classification Search
CPC .......................... C12N 15/111; C12N 15/113
See application file for complete search history.

(56) References Cited

U.S. PATENT DOCUMENTS

| | | | |
|---|---|---|---|
| 5,034,506 A | 7/1991 | Summerton et al. | 528/391 |
| 5,418,139 A | 5/1995 | Campbell | 435/7.21 |
| 5,541,308 A | 7/1996 | Hogan et al. | 536/23.1 |
| 5,593,974 A | 1/1997 | Rosenberg et al. | 514/44 |
| 5,608,046 A | 3/1997 | Cook et al. | 536/23.1 |
| 5,627,263 A | 5/1997 | Ruoslahti et al. | 530/327 |
| 5,658,764 A | 8/1997 | Pergolizzi et al. | 435/91.2 |
| 5,741,645 A | 4/1998 | Orr et al. | 435/6 |
| 5,766,847 A | 6/1998 | Jäckle et al. | 435/6 |
| 5,853,995 A | 12/1998 | Lee | 435/6 |
| 5,869,252 A | 2/1999 | Bouma et al. | 435/6 |
| 5,916,808 A | 6/1999 | Kole et al. | 435/375 |
| 5,962,332 A | 10/1999 | Singer et al. | 436/94 |
| 5,968,909 A | 10/1999 | Agrawal et al. | 514/44 |
| 5,976,879 A | 11/1999 | Kole et al. | 435/375 |
| 6,124,100 A | 9/2000 | Jin | 435/6 |
| 6,130,207 A | 10/2000 | Dean et al. | 514/44 |
| 6,133,031 A | 10/2000 | Monia et al. | 435/375 |
| 6,172,208 B1 | 1/2001 | Cook | 536/23.1 |
| 6,172,216 B1 | 1/2001 | Bennett et al. | 536/24.5 |

(Continued)

FOREIGN PATENT DOCUMENTS

| | | | | |
|---|---|---|---|---|
| CA | 2319149 | 10/2001 | | C07H 21/00 |
| CA | 2526893 | 11/2004 | | A61K 31/7008 |

(Continued)

OTHER PUBLICATIONS

Aartsma-Rus et al., Guidelines for antisense oligonucleotide design and insight into splice-modulating mechanisms, *Molecular Therapy*, pp. 548-553, Sep. 2008.

(Continued)

*Primary Examiner* — Dana Shin

(74) *Attorney, Agent, or Firm* — Sunstein Kann Murphy & Timbers LLP

(57) ABSTRACT

The invention relates to a method for inducing or promoting skipping of exon 45 of DMD pre-mRNA in a Duchenne Muscular Dystrophy patient, preferably in an isolated (muscle) cell, the method comprising providing an isolated muscle cell with a molecule that binds to a continuous stretch of at least 21 nucleotides within the exon. The invention further relates to such molecule used in the method.

23 Claims, 2 Drawing Sheets

(56) References Cited

U.S. PATENT DOCUMENTS

| | | | |
|---|---|---|---|
| 6,210,892 B1 | 4/2001 | Bennett et al. | 435/6 |
| 6,251,589 B1 | 6/2001 | Tsuji et al. | 435/6 |
| 6,280,938 B1 | 8/2001 | Ranum et al. | 435/6 |
| 6,300,060 B1 | 10/2001 | Kantoff et al. | 435/6 |
| 6,322,978 B1 | 11/2001 | Kahn et al. | 435/6 |
| 6,329,501 B1 | 12/2001 | Smith et al. | 530/329 |
| 6,355,481 B1 | 3/2002 | Li et al. | 435/331 |
| 6,355,690 B1 | 3/2002 | Tsuji | 514/706 |
| 6,369,038 B1 | 4/2002 | Blumenfeld et al. | 514/44 |
| 6,379,698 B1 | 4/2002 | Leamon | 424/450 |
| 6,399,575 B1 | 6/2002 | Smith et al. | 514/16 |
| 6,514,755 B1 | 2/2003 | Ranum et al. | 435/320.1 |
| 6,623,927 B1 | 9/2003 | Brahmachari et al. | 435/6 |
| 6,653,466 B2 | 11/2003 | Matsuo | 536/24.3 |
| 6,653,467 B1 | 11/2003 | Matsuo et al. | 536/24.5 |
| 6,670,461 B1 | 12/2003 | Wengel et al. | 536/23.1 |
| 6,727,355 B2 | 4/2004 | Matsuo et al. | 536/24.5 |
| 6,794,192 B2 | 9/2004 | Parums et al. | 436/15 |
| 6,902,896 B2 | 6/2005 | Ranum et al. | 435/6 |
| 6,982,150 B2 | 1/2006 | Sheetz et al. | 435/7.2 |
| 7,001,994 B2 | 2/2006 | Zhu | 536/4.1 |
| 7,034,009 B2 | 4/2006 | Pavco et al. | 514/44 |
| 7,118,893 B2 | 10/2006 | Ranum et al. | 435/91.2 |
| 7,189,530 B2 | 3/2007 | Botstein et al. | 435/69.1 |
| 7,202,210 B2 | 4/2007 | Wolfman et al. | 514/12 |
| 7,250,404 B2 | 7/2007 | Felgner et al. | 514/44 |
| 7,320,965 B2 | 1/2008 | Sah et al. | 514/44 |
| 7,355,018 B2 | 4/2008 | Glass | 530/399 |
| 7,405,193 B2 | 7/2008 | Lodish et al. | 514/2 |
| 7,442,782 B2 | 10/2008 | Ranum et al. | 536/23.1 |
| 7,514,551 B2 | 4/2009 | Rabbani et al. | 536/26.6 |
| 7,534,879 B2 | 5/2009 | van Deutekom | 536/24.5 |
| 7,589,189 B2 | 9/2009 | Ichiro et al. | 536/24.5 |
| 7,655,785 B1 | 2/2010 | Bentwich | 536/24.1 |
| 7,771,727 B2 | 8/2010 | Fuselier et al. | 424/185.1 |
| 7,807,816 B2 | 10/2010 | Wilton et al. | 536/24.5 |
| 7,902,160 B2 | 3/2011 | Matsuo et al. | 514/44 |
| 7,960,541 B2 | 6/2011 | Wilton et al. | 536/24.5 |
| 8,084,601 B2 | 12/2011 | Popplewell et al. | 536/24.5 |
| 8,232,384 B2 | 7/2012 | Wilton et al. | 536/24.5 |
| 8,324,371 B2 | 12/2012 | Popplewell et al. | 536/24.5 |
| 8,450,474 B2 | 5/2013 | Wilton et al. | 536/24.5 |
| 8,455,634 B2 | 6/2013 | Wilton et al. | 536/24.5 |
| 8,455,635 B2 | 6/2013 | Wilton et al. | 536/24.5 |
| 8,455,636 B2 | 6/2013 | Wilton et al. | 536/24.5 |
| 8,476,423 B2 | 7/2013 | Wilton et al. | 536/24.5 |
| 8,486,907 B2 | 7/2013 | Wilton et al. | 514/44 |
| 8,524,880 B2 | 9/2013 | Wilton et al. | 536/24.5 |
| 8,865,883 B2* | 10/2014 | Sazani | C12N 15/111 435/325 |
| 2001/0056077 A1 | 12/2001 | Matsuo | 514/44 |
| 2002/0049173 A1 | 4/2002 | Bennett et al. | 514/44 |
| 2002/0055481 A1 | 5/2002 | Matsuo et al. | 514/44 |
| 2002/0115824 A1 | 8/2002 | Engler et al. | 530/324 |
| 2002/0165150 A1 | 11/2002 | Ben-Sasson | 514/44 |
| 2003/0073215 A1 | 4/2003 | Baker et al. | 435/183 |
| 2003/0082763 A1 | 5/2003 | Baker et al. | 435/183 |
| 2003/0082766 A1 | 5/2003 | Baker et al. | 435/183 |
| 2003/0109476 A1 | 6/2003 | Kmiec et al. | 514/44 |
| 2003/0124523 A1 | 7/2003 | Asselbergs et al. | 435/6 |
| 2003/0134790 A1 | 7/2003 | Langenfeld | 514/12 |
| 2003/0235845 A1 | 12/2003 | Van Ommen et al. | 435/6 |
| 2003/0236214 A1 | 12/2003 | Wolff et al. | 514/44 |
| 2004/0101852 A1 | 5/2004 | Bennett et al. | 435/6 |
| 2004/0132684 A1 | 7/2004 | Sampath et al. | 514/44 |
| 2004/0226056 A1 | 11/2004 | Roch et al. | 800/12 |
| 2005/0096284 A1 | 5/2005 | McSwiggen | 514/44 |
| 2005/0222009 A1 | 10/2005 | Lamensdorf et al. | 514/7 |
| 2005/0246794 A1 | 11/2005 | Khvorova et al. | 800/286 |
| 2005/0277133 A1 | 12/2005 | McSwiggen | 435/6 |
| 2006/0074034 A1 | 4/2006 | Collins et al. | 514/44 |
| 2006/0148740 A1 | 7/2006 | Platenburg | 514/44 |
| 2007/0021360 A1 | 1/2007 | Nyce et al. | 514/44 |
| 2007/0082861 A1 | 4/2007 | Matsuo et al. | 514/44 |
| 2007/0141628 A1 | 6/2007 | Cunningham et al. | 435/7.1 |
| 2007/0275914 A1 | 11/2007 | Manoharan et al. | 514/44 |
| 2007/0292408 A1 | 12/2007 | Singh et al. | 424/130.1 |
| 2008/0015158 A1 | 1/2008 | Ichiro et al. | 514/44 |
| 2008/0039418 A1 | 2/2008 | Freier | 514/44 |
| 2008/0113351 A1 | 5/2008 | Naito et al. | 435/6 |
| 2008/0200409 A1 | 8/2008 | Wilson et al. | 514/44 |
| 2008/0207538 A1 | 8/2008 | Lawrence et al. | 514/41 |
| 2008/0249294 A1 | 10/2008 | Haeberli et al. | 536/24.5 |
| 2009/0092981 A1 | 4/2009 | Swayze et al. | 435/6 |
| 2010/0081627 A1 | 4/2010 | Sampath et al. | 514/47 |
| 2010/0099750 A1 | 4/2010 | McSwiggen et al. | 514/44 R |
| 2010/0168212 A1* | 7/2010 | Popplewell | A61K 31/7088 514/44 R |
| 2010/0216238 A1* | 8/2010 | Baker | C12N 15/111 435/375 |
| 2011/0015253 A1 | 1/2011 | Wilton et al. | 514/44 A |
| 2011/0015258 A1 | 1/2011 | Wilton et al. | 514/44 R |
| 2011/0046203 A1 | 2/2011 | Wilton et al. | 514/44 A |
| 2011/0263686 A1 | 10/2011 | Wilton et al. | 514/44 A |
| 2012/0022144 A1 | 1/2012 | Wilton et al. | 514/44 A |
| 2012/0022145 A1 | 1/2012 | Wilton et al. | 514/44 A |
| 2012/0029057 A1 | 2/2012 | Wilton et al. | 514/44 A |
| 2012/0029058 A1 | 2/2012 | Wilton et al. | 514/44 A |
| 2012/0029059 A1 | 2/2012 | Wilton et al. | 514/44 A |
| 2012/0029060 A1 | 2/2012 | Wilton et al. | 514/44 A |
| 2012/0041050 A1 | 2/2012 | Wilton et al. | 514/44 A |
| 2013/0116310 A1 | 5/2013 | Wilton et al. | 514/44 A |
| 2013/0217755 A1 | 8/2013 | Wilton et al. | 514/44 A |
| 2013/0253033 A1 | 9/2013 | Wilton et al. | 514/44 A |
| 2013/0253180 A1 | 9/2013 | Wilton et al. | 536/24.5 |
| 2013/0274313 A1 | 10/2013 | Wilton et al. | 514/44 A |
| 2013/0331438 A1 | 12/2013 | Wilton et al. | 514/44 A |

FOREIGN PATENT DOCUMENTS

| | | | |
|---|---|---|---|
| EP | 0614977 | 9/1994 | C12N 15/12 |
| EP | 0438512 | 12/1997 | C12Q 1/68 |
| EP | 0850300 | 7/1998 | C12N 15/11 |
| EP | 1015628 | 7/2000 | C12Q 1/68 |
| EP | 1054058 | 11/2000 | C12N 15/11 |
| EP | 1133993 | 9/2001 | A61K 38/17 |
| EP | 1160318 | 12/2001 | C12N 15/11 |
| EP | 1191097 | 3/2002 | C12N 15/11 |
| EP | 1191098 | 3/2002 | C12N 15/11 |
| EP | 1380644 | 1/2004 | C12N 15/11 |
| EP | 1487493 | 12/2004 | A61K 47/48 |
| EP | 1495769 | 1/2005 | A61K 47/48 |
| EP | 1501931 | 2/2005 | C12N 15/11 |
| EP | 1544297 | 6/2005 | C12N 15/11 |
| EP | 1567667 | 8/2005 | C12Q 1/68 |
| EP | 1568769 | 8/2005 | C12N 15/11 |
| EP | 1619249 | 1/2006 | C12N 15/11 |
| EP | 2 344 637 B1 | 12/2014 | |
| KR | 2003-0035047 | 5/2003 | A61K 48/00 |
| WO | WO 93/01286 | 1/1993 | C12N 15/11 |
| WO | WO 95/16718 | 6/1995 | C08F 255/02 |
| WO | WO 95/21184 | 8/1995 | C07H 19/16 |
| WO | WO 95/30774 | 11/1995 | C12Q 1/68 |
| WO | WO 97/12899 | 4/1997 | C07H 21/04 |
| WO | WO 97/30067 | 8/1997 | C07H 21/04 |
| WO | WO 98/18920 | 5/1998 | C12N 15/12 |
| WO | WO 98/43993 | 10/1998 | C07H 21/00 |
| WO | WO 98/49345 | 11/1998 | C12Q 1/68 |
| WO | WO 98/53804 | 12/1998 | A61K 31/00 |
| WO | WO 99/16871 | 4/1999 | C12N 15/11 |
| WO | WO 99/55857 | 11/1999 | C12N 15/11 |
| WO | WO 00/24885 | 5/2000 | C12N 15/11 |
| WO | WO 01/16312 A2 | 3/2001 | C12N 15/11 |
| WO | WO 01/59102 A2 | 8/2001 | C12N 15/11 |
| WO | WO 01/79283 | 10/2001 | C07K 14/47 |
| WO | WO 01/83503 | 11/2001 | C07H 21/00 |
| WO | WO 01/83695 | 11/2001 | |
| WO | WO 02/24906 | 3/2002 | C12N 15/11 |
| WO | WO 02/26812 | 4/2002 | C07K 14/47 |
| WO | WO 02/29006 A2 | 4/2002 | |
| WO | WO 02/29056 | 4/2002 | C12N 15/12 |
| WO | WO 03/002739 | 1/2003 | C12N 15/11 |
| WO | WO 03/013437 | 2/2003 | |
| WO | WO 03/014145 | 2/2003 | C07K 7/00 |

(56) References Cited

FOREIGN PATENT DOCUMENTS

| WO | WO 03/037172 | 5/2003 | |
|---|---|---|---|
| WO | WO 03/062258 A1 | 7/2003 | ............ C07H 21/02 |
| WO | WO 03/095647 | 11/2003 | ............ C12N 15/11 |
| WO | WO 2004/011060 | 2/2004 | |
| WO | WO 2004/015106 | 2/2004 | ............ C12N 15/11 |
| WO | WO 2004/016787 | 2/2004 | ............ C12N 15/11 |
| WO | WO 2004/037854 | 5/2004 | ............... C07K 1/04 |
| WO | WO 2004/047741 A2 | 6/2004 | |
| WO | WO 2004/083432 | 9/2004 | ............ C12N 15/11 |
| WO | WO 2004/083446 | 9/2004 | |
| WO | WO 2004/101787 | 11/2004 | ............ C12N 15/11 |
| WO | WO 2004/108157 | 12/2004 | .......... A61K 39/395 |
| WO | WO 2005/019453 | 3/2005 | ............ C12N 15/11 |
| WO | WO 2005/023836 | 3/2005 | |
| WO | WO 2005/035550 | 4/2005 | |
| WO | WO 2005/085476 | 9/2005 | ............... C12Q 1/68 |
| WO | WO 2005/086768 | 9/2005 | |
| WO | WO 2005/105995 | 11/2005 | ............ C12N 15/11 |
| WO | WO 2005/115439 | 12/2005 | ............ A61K 38/18 |
| WO | WO 2005/115479 | 12/2005 | ............ A61K 48/00 |
| WO | WO 2005/116204 | 12/2005 | ............ C12N 15/09 |
| WO | WO 2006/000057 | 1/2006 | ........... C12N 15/111 |
| WO | WO 2006/007910 | 1/2006 | ............ A61K 31/56 |
| WO | WO 2006/017522 | 2/2006 | ............ A61K 48/00 |
| WO | WO 2006/031267 | 3/2006 | ............ C12N 15/11 |
| WO | WO 2006/054262 | 5/2006 | |
| WO | WO 2006/083800 | 8/2006 | |
| WO | WO 2006/108052 | 10/2006 | ............ A61K 47/48 |
| WO | WO 2006/112705 | 10/2006 | ......... A61K 31/7088 |
| WO | WO 2006/121960 | 11/2006 | ............ C12N 15/11 |
| WO | WO 2007/002904 | 1/2007 | ............... C12Q 1/68 |
| WO | WO 2007/004979 | 1/2007 | ............ A61K 38/00 |
| WO | WO 2007/044362 | 4/2007 | ............ A61K 48/00 |
| WO | WO 2007/089584 | 8/2007 | ............ A61K 48/00 |
| WO | WO 2007/089611 | 8/2007 | ............ C12N 15/11 |
| WO | WO 2007/135105 | 11/2007 | ............ C12N 15/11 |
| WO | WO 2009/054725 A2 | 4/2009 | |
| WO | WO 2011/057350 | 5/2011 | ........... C12N 15/113 |

OTHER PUBLICATIONS

Aartsma-Rus et al., Exploring the frontiers of therapeutic exon skipping for Duchenne Muscular Dystrophy by double targeting within one or multiple exons, *Molecular Therapy*, 14(3): 401-407, Sep. 2006.

Aartsma-Rus et al., Functional Analysis of 114 Exon-Internal AONs for Targeted DMD Exon Skipping: Indication for Steric Hindrance of SR Protein Binding Sites, *Oligonucleotides*, 15: 284-297, 2005.

Aartsma-Rus et al., Antisense Mediated exon skipping; A Versatile Tool with Therapeutic and Research Applications, *RNA*, 13(10):1609-1624, 2007.

Aartsma-Rus et al., Antisense-Induced Exon Skipping for Duplications in Duchenne Muscular Dystrophy, *BMC Med. Genet.* 8:43, 9 pages, Jul. 5, 2007.

Aartsma-Rus et al., Therapeutic Modulation of DMD splicing by Blocking Exonic Splicing Enhancer Sites with Antisense Oligonucleotides, *Ann NY Acad Sci*, 1082, pp. 74-76, 2006.

Aartsma-Rus et al., Antisense-Induced Multiexon Skipping for Duchenne Muscular Dystrophy Makes More Sense, *Am. J. Hum. Genet*, 74: 83-92, 2004.

Aartsma-Rus et al., Targeted exon skipping as a potential gene correction therapy for Duchenne muscular dystrophy, *Neuromuscular Disorders*, 12: S71-S77, 2002.

Aartsma-Rus et al., Therapeutic antisense-induced exon skipping in cultured muscle cells from six different DMD patients, *Human Molecular Genetics*, 12(8): 907-14, 2003.

Aartsma-Rus et al., Comparative analysis of antisense oligonucleotide analogs for targeted DMD exon 46 skipping in muscle cells, *Gene Therapy*, 11: 1391-1398, 2004.

Aartsma-Rus et al., Theoretic Applicability of Antisense-Mediated Exon Skipping for Duchenne Muscular Dystrophy Mutations, *Human Mutation*, 30(3): 293-299, 2009.

Abbs et al., A convenient multiplex Pcr system for the detection of dystrophin gene deletions: a comparative analysis with cDNA hybridisation shows mistypings by both methods, *J. Med. Genet*, 28:304-311, 1991.

Agrawal et al., Antisense therapeutics: is it as simple as complementary base recognition? *Mol. Med. Today*, 6:72-81, Feb. 2000.

Alter et al., Systemic delivery of morpholino oligonucleotide restores dystrophin expression bodywide and improves dystrophic pathology. *Nature Medicine*, 12(2):175-177, Feb. 2006; Epub Jan. 26, 2006.

Amalfitano et al., Structure and mutation of the dystrophin gene, In: Dystrophin: Gene, protein and cell biology, (Brown and Lucy, eds). Cambridge University Press, pp. 1-16,1997.

Anderson et al., Correlated NOS-I[mu] and myf5 expression by satellite cells in mdx mouse muscle regeneration during NOS manipulation and deflazacort treatment, *Neuromusccular Disorders*, 13(5): 388-396, Jan. 2003.

Arap, Steps toward mapping the human vasculature by phage display, *Nature Medicine*, 8(2):121-127, Feb. 2002.

Arechavala-Gomeza. et al., Comparative Analysis of Antisense Oligonucleotide Sequences for Targeted Skipping of Exon 51 During Dystrophin pre-mRNA Splicing in Human Muscle, *Hum Gene Ther* 18(9):798-810, Sep. 2007.

Arruda, The role of immunosuppression in gene and cell based treatments for Duchenne Muscular Dystrophy, *Molecular Therapy*, 15(6): 1040-1041, Jun. 2007.

Arzumanov et al., Inhibition of HIV-1 Tat-dependent trans activation by steric block chimeric 2'-O-methyl/LNA oligoribonucleotides. *Biochemistry*, 40(48): 14645-14654, 2001.

Austin et al., Cloning and characterization of alternatively spliced isoforms of Dp71, *Human Molecular Genetics* 4(9): 1475-1483, 1995.

Austin et al., Expression and synthesis of alternatively spliced variants of Dp71 in adult human brain, *Neuromuscular Disorders*,10:187-193, 2000.

Barabino et al., Antisense probes targeted to an internal domain in U2 snRNP specifically inhibit the second step of pre-mRNA splicing, *Nucleic Acids Research*, 20(17): 4457-4464, 1992.

Barany, The ligase chain reaction in a PCR world, PCR Methods and Applications, 1(1): 5-16, Aug. 1991.

Beggs et al., Detection of 98% of DMD/BMD gene deletions by polymerase chain reaction, *Human Genetics*, 86: 45-48, 1990.

Bremmer-Bout, et al., Targeted exon skipping in transgenic hDMD mice: A model for direct preclinical screening of human-specific antisense oligonucleotides, Molecular Therapy, 10(2): 232-240, Aug. 2004.

Brett et al., EST comparison indicates 38% of human mRNAs contain possible alternative splice forms, FEBS Letters, 474(1): 83-86, 2000.

Brown et al., Gene delivery with synthetic (non viral) carriers., *Int. J. Pharm.*, vol. 229, Nos. 1-2, pp. 1-21, Oct. 23, 2001 (Abstract).

Buck et al., Design Strategies and Performance of Custom DNA Sequencing Primers, BioTechniques, 27(3): 528-536, Sep. 1999.

Burnett et al., DNA sequence-specific polyamides alleviate transcription inhibition associated with long GAA-TTC repeats in Friedreich's ataxia, *PNAS*, 103(31): 11497-11502, Aug. 2006.

Caplen, et al., Rescue of polyglutamine-mediated cytotoxicity by double-stranded RNA-mediated RNA interference, *Human Molecular Genetics*, 11(2): 175-184, 2002.

Cartegni, et al, Listening to silence and understanding nonsense: exonic mutations that affect splicing, *Nature Reviews Genetics*, 3: 285-298, Apr. 2002.

Chaubourt et al., Muscular nitric oxide synthase ([mu]NOS) and utrophin, *J. Physiology Paris*, 96(1-2): 43-52, Jan.-Mar. 2002.

Coulter et al., Identification of a new class of exonic splicing enhancers by in vivo selection, *Mol. Cell. Biol.* 17(4) 2143-2150, Apr. 1997.

Cooke, Basic Principles of Antisense Therapeutics, Antisense Research and Application, Handbook of Experimental Pharmacology, 131: 1-50, 1998.

Dahlqvist et al., Functional notch signaling is required for BMP4-induced inhibition of myogenic differentiation, *Development* 130: 6089-6099, Aug. 2003.

(56) References Cited

OTHER PUBLICATIONS

De Angelis et al., Chimeric snRNA molecules carrying antisense sequences against the splice junctions of exon 51 of the dystrophin pre-mRNA exon skipping and restoration of a dystrophin synthesis in delta 48-50 DMD cells, *PNAS*, 99(14): 9456-9461, Jul. 9, 2002.
Denny et al., Oligo-riboprobes, Tools for in situ hybridization. *Histochemistry* 89:481-493, 1988.
Dickson et al., Screening for antisense modulation of dystropin pre-mRNA splicing, *Neuromuscul. Disord.*, Supp. 1, S67-S70, 2002.
Dirksen et al., Mapping the SF2/ASF Binding Sites in the Bovine Growth Hormone Exonic Splicing Enhancer, *J. Biological Chemistry*, 275(37): 29170-29177, Sep. 15, 2000.
Dorchies et al., Green tea extract and its major polyphenol (-)-epigallocatechin gallate improve muscle function in a mouse model for Duchenne muscular dystrophy, *Am .J. Cell Physiological*, 290: C616-C625, 2006.
Duboc et al., Effect of Perindopril on the Onset and Progression of Left Ventricular Dysfunction in Duchenne Muscular Dystrophy, *J. Amer. Coll. Cardiology*, 45(6): 855-857, Mar. 15, 2005.
Dubowitz, Foreword, Neuromuscular Disorders, 12: S1-S2, 2002.
Dubowitz, Special Centennial Workshop, 101$^{st}$ ENMC International Workshop: Therapeutic Possibilities in Duchenne Muscular Dystrophy, Nov. 30-Dec. 2, 2001, Naarden, The Netherlands, *Neuromuscular Disorders*, 12: 421-431, 2002.
Dunckley et al., Modulation of Splicing in the DMD Gene by Antisense Oligoribonucleotides, *Nucleosides & Nucleotides*, 16 (7-9):1665-1668, 1997.
Dunckley et al., Modification of splicing in the Dsytrophin gene in cultured Mdx muscle cells by antisense oligoribonucleotides, *Human Molecular Genetics*, 7(7):1083-1090, 1995.
El-Andaloussi et al., Abstract: Induction of splice correction by cell-penetrating peptide nucleic acids., *J. Gene Med.*, 8(10):1262-1273, Oct. 2006.
Erba et al., Structure, chromosome location, and expression of the human gamma-actin gene: differential evolution, location, and expression of the cytoskeletal beta- and gamma-actin genes, *Mol. Cell. Biology*, 8(4): 1775-1789, Apr. 1988.
Errington et al., Target selection for antisense oligonucleotide induced exon skipping in the dystrophin gene. *J Gene Med*, 5(6):518-527, 2003.
Fainsod et al., The dorsalizing and neural inducing gene *follistatin* in an antagonist of BMP-4, *Mechanisms of Development*, 63: 39-50,1997.
Feener et al., Alternative splicing of human dystrophin mRNA generates isoforms at the carboxy terminus, *Nature*, 338: 509-511, Apr. 6, 1989.
Fluiter, K., In Vivo tumor growth inhibition and biodistribution studies of locked nucleic acid (LNA) antisense oligonucleotides, *Nucl. Acids Research*, 31(3): 953-962, 2003.
Fu et al., An Unstable Triplet Repeat in a Gene Related to Myotonic Muscular Dystrophy *Science*, 255: 1256-1258, 1992.
Furling et al., Viral vector producing antisense RNA restores myotonic dystrophy myoblast functions, *Gene Therapy*, 10: 795-802, 2003.
Galderisi et al., Myotonic dystrophy: antisense oligonucleotide inhibition of DMPK gene expression in vitro, *Biochem Biophys Res Commun* 221: 750-754, 1996.
Galderisi et al., Antisense Oligonucleotides as Therapeutic Agents, *Journal of Cellular Physiology*, 181: 251-257, 1999.
Garcia-Blanco et al., Alternative splicing in disease and therapy, *Nature Biotechnology*, 22(5): 535-546, May 2004.
Ginjaar et al, Dystrophin nonsense mutation induces different levels of exon 29 skipping and leads to variable phenotypes within one BMD family, *European J. Human Genetics* 8: 793-796, 2000.
Gollins et al., High-efficiency plasmid gene transfer into dystrophic muscle, *Gene Therapy*, 10: 504-512, 2003.
Grady, Promising Dystrophy Drug Clears Early Test, *The New York Times*, 3 pages, Dec. 27, 2007.

Granchelli et al. Pre-clinical screening of drugs using the mdx mouse, *Neuromuscular Disorders*, 10(4-5): 235-239, 2000.
Gryaznov, Oligonucleotide N3' → P5' phosphoramidates as potential therapeutic agents, *Biochem Biophys. Acta*, 1489: 131-140, 1999.
Hagiwara et al., A novel point mutation ($G^{-1}$ to T) in a 5' splice donor site of intron 13 of the dystrophin gene results in exon skipping and is responsible for Becker muscular dystrophy, *Am J. Hum Genet.*, 54(1): 53-61, 1994.
Handa et al., The AUUCU repeats responsible for spinocerebellar ataxia type 10 form unusual RNA hairpins, *J. Biological Chemistry*, 280(32): 29340-29345, Aug. 12, 2005.
Harding et al., The Influence of Antisense Oligonucleotide Length on Dystrophin Exon Skipping, *Molecular Therapy*, 15(1): 157-166, Jan. 2007.
Hasholt et al., Antisense downregulation of mutant huntingtin in a cell model, *J. Gene Medicine*, 5: 528-538, 2003.
Heemskerk et al., Development of Antisense-Mediated Exon Skipping as a Treatment for Duchenne Muscular Dystrophy, *Ann. NY Acad. Sci.*, 1175: 71-79, 2009.
Heemskerk et al., Preclinical PK and PD Studies on 2' O-methyl-phosphorothioate RNA antisense Oligonucleotides in the MDX Mouse Model, *Mol. Ther.*, 18(6): 1210-1217, Jun. 2010.
Highfield, Science: Boffin log, The Daily Telegraph, http://www.telegraph.co.uk/science/science-news/3320286/Science-Boffin-log.html, (Hope for Muscular Dystrophy Drug) Jan. 1, 2008, 5 pages.
Hoffman, Skipping toward Personalized Molecular Medicine, *N. Eng. J. Med.*,357(26): 2719-2722, Dec. 27, 2007.
Hoffman et al., Somatic reversion/suppression of the mouse *mdx* phenotype in vivo, *J. Neurological Sciences*, 99: 9-25, 1990.
Hussey et al., Analysis of five Duchenne muscular dystrophy exons and gender determination using conventional duplex polymerase chain reaction on single cells, *Molecular Human Reproduction*, 5(11): 1089-1094, 1999.
Iezzi et al., Decetylase inhibitors increase muscle cell size by promoting myoblast recruitment and fusion through induction of follistation, *Development Cell*, 6: 673-684, May 2004.
Ikezawa et al., Dystrophin gene analysis on 130 patients with Duchenne Muscular dystrophy with a special reference to muscle mRNA analysis, *Brain & Develop.*, 20: 165-168, 1998.
Ito et al. Purine-Rich Exon Sequences Are Not Necessarily Splicing Enhancer Sequence in the Dystrophin Gene, *Kobe J. Med. Sci.*, 47: 193-202, Oct. 4, 2001.
Karras et al., Deletion of Individual Exons and Induction of Soluble Murine Interleukin-5 Receptor-alpha Chain Expression through Antisense Oligonucleotide-Mediated Redirection of Pre-mRNA Splicing, *Molecular Pharmacology*,58: 380-387, 2000.
Kerr et al., Bmp Regulates Skeletal Myogenesis at Two Steps, Molecular Cellular Proteomics 2.9: 976. 123.8, 2003 (Abstract Only).
Kinali et al, Local Restoration of Dystrophin Expression With the Morpholino Oligomer AVI-4658 in Duchenne Muscular Dystrophy: A Single-blind, Placebo-Controlled Dose-Escalation, Proof-of Concept Study, *Lancet Neurol.*, 8: 918-928, Aug. 26, 2009.
Kurrek et al., Design of antisense oligonucleotides stabilized by locked nucleic acids, *Nucleic Acids Research*, 30(9): 1911-1918, 2002.
Langlois et al., Hammerhead ribozyme-mediated destruction of nuclear foci in myotonic dystrophy myoblasts, *Molecular Therapy*, 7(5): 670-680, May 2003.
Laptev et al., Specific inhibition of expression of a human collagen gene (COL1A1) with modified antisense oligonucleotides. The most effective target sites are clustered in double-stranded regions of the predicted secondary structure for the mRNA *Biochemistry*, 33(36): 11033-11039, 1994.
Lee et al., Receptor mediated uptake of peptides that bind the human transferrin receptor, *Eur. J. Biochem.*, 268: 2004-2012, 2001.
Liu et al., A mechanism for exon skipping caused by nonsense or missense mutations in BRCA1 and other genes, *Nature Genetics*, 27(1):55-58, Jan. 2001.
Liu et al., Specific inhibition of Huntington's disease gene expression by siRNAs in cultured cells, *Proc. Japan Acad.*, 79,Ser. B: 293-298, 2003.

(56) References Cited

OTHER PUBLICATIONS

Liu et al., Identification of functional exonic splicing enhancer motifs recognized by individual SR proteins, *Genes & Development*, 12:1998-2012, 1998.
Lu et al., Functional Amounts of Dystrophin Produced by Skipping the Mutated Exon in the mdx Dystrophic Mouse *Nature Medicine*, 9(8): 1009-1014, Aug. 2003.
Lu et al., Massive Idiosyncratic Exon Skipping Corrects the Nonsense Mutation in Dystrophic Mouse Muscle and Produces Functional Revertant Fibers by Clonal Expansion, *The Journal of Cell Biology*, 148(5): 985-995, Mar. 6, 2000.
Lu et al., Non-viral gene delivery in skeletal muscle: a protein factory, *Gene Therapy*, 10:131-142, 2003.
Lu et al., Systemic delivery of antisense oligoribonucleotide restores dystrophin expression in body-wide skeletal muscles, *PNAS*, 102(1): 198-203, Jan. 4, 2005.
Mann et al., Antisense-induced exon skipping and synthesis of dystrophin in the mdx mouse, *PNAS*, 98(1): 42-47, Jan. 2, 2001.
Mann et al., Improved antisense oligonucleotide induced exon skipping in the mdx mouse model of muscular dystrophy, *J Gene Med.*, 4(6): 644-654, 2002.
Martiniuk et al., Correction of glycogen storage disease type II by enzyme replacement with a recombinant human acid maltase produced by over-expression in a CHO-DHFR(neg) cell line, *Biochem. Biophys. Res. Commun.*, 276( 3): 917-923, Oct. 5, 2000 (Abstract).
Matsuo et al., Partial deletion of a dystrophin gene leads to exon skipping and to loss of an intra-exon hairpin structure from the predicted mRNA precursor, *Biochem. Biophys. Res. Commun.*, 182(2): 495-500, Jan. 31, 1992.
Matsuo, Duchenne/ Becker muscular dystrophy: from molecular diagnosis to gene therapy, *Brain and Development*, 18(3): 167-172, 1996.
Matsuo et al., Exon Skipping during Splicing of Dystrophin mRNA Precursor due to an Intraexon Deletion in the Dystrophin Gene of Duchenne Muscular Dystrophy Kobe, *J. Clin. Invest.*, 87: 2127-2131, Jun. 1991.
Matsuo, Duchenne and Becker Muscular Dystrophy: From Gene Diagnosis to Molecular Therapy, IUBMB Life, 53: 147152, 2002.
Matteucci, Structural modifications toward improved antisense oligonucleotides, *Perspectives in Drug Discovery and Design*, 4: 1-16, 1996.
McClorey et al., Induced Dystrophin Exon Skipping in Human Muscle Explants, Neuromuscul Disorders,16: 583-590, 2006.
Miller et al., Antisense oligonucleotides: strategies for delivery, *PSTT*, 9(1): 377-386, Dec. 1998.
Monaco et al., An Explanation for the Phenotypic Differences between Patients Bearing Partial Deletions of the DMD Locus, Genomics, 2: 90-95, 1988.
Moon et. al., Target site Search and effective inhibition of leukaemic cell growth by a covalently closed multiple anti-sense oligonucleotide to c-myb, *Biochemical Journal*, 346: 295-303, 2000.
Munroe, Antisense RNA inhibits splicing of pre-mRNA in vitro, The EMBO Journal, 7(8): 2523-2532, 1988.
Muntoni et al., A Mutation in the Dystrophin Gene Selectively Affecting Dystrophin Expression in the Heart. *J. Clin Invest.*, 96: 693-699, Aug. 1995.
Muntoni et al., 149th ENMC International Workshop and 1st TREAT-NMD Workshop on: Planning Phase I/II Clinical trials using Systemically Delivered Antisense Oligonucleotides in Duchenne Muscular Dystrophy, *Neuromuscular Disorders*, 18: 268-275, 2008.
Nishio, et al., Identification of a novel first exon in the human dystrophin gene and of a new promoter located more than 500 kb upstream of the nearest known promoter. *J. Clin. Investigation*, 94: 1037-1042, Sep. 1994.
Onlo Nederlandsch Octroobureau, Grounds of Appeal—EP1619249, 16 pages, Jan. 8, 2014.
Onlo Nederlandsch Octroobureau, List of all submitted documents—EP1619249, 4 pages, Jan. 8, 2014.
Onlo Nederlandsch Octroobureau, Reply to the Grounds of Appeal filed in the opposition Proceedings of EP1619249, dated Jan. 8, 2014.
Opalinska et al., Nucleic-acid therapeutics: basic principles and recent applications, *Nature Reviews Drug Discovery*, 1:503-514, Jul. 2002.
O'Shaughnessy et al., Superior Survival With Capecitabine Plus Docetaxel Combination Therapy in Anthracycline-Pretreated Patients With Advanced Breast Cancer: Phase III Trial Results, *J. Clinical Oncology*, 20(12): 2812-2823, Jun. 15, 2002.
Patel et al., The Function of Myostatin and strategies of Myostatin blockade—new hope for therapies aimed at promoting growth of skeletal muscle, *Neuromuscular Disorders* ,15(2): 117-126, 2005.
Phillips, Antisense Inhibition and Adeno-Associated Viral Vector Delivery for Reducing Hypertension, Hypertension, 29(1), Part 2: 177-187, Jan. 1997.
Politano et al., Gentamicin administration in Duchenne patients with premature stop codon. *Acta Myologica* 22(1):15-21, 2003.
Popplewell et al., Design of Phosphorodiamidate Morpholino Oligomers (PMOs) for the Induction of Exon Skipping of the Human DMD Gene, *Mol. Therap.* 17(3): 554-561, Mar. 2009.
Pramono et al., Induction of Exon Skipping of the Dystrophin Transcript in Lymphoblastoid Cells by Transfecting an Antisense Oligodeoxynucleotide Complementary to an Exon Recognition Sequence, *BBRC*, 226:445-449, 1996.
Radley et al., Duchenne muscular dystrophy: Focus on pharmaceutical and nutritional interventions, *International J. Biochem. and Cell Biol.*, 39(3): 469-477, Oct. 2006.
Rando, Thomas A., Oligonucleotide-mediated gene therapy for muscular dystrophies, *Neuromuscular Disorders*, 12: S55-S60, 2002.
Reitter B., Deflazacort vs. prednisone in Duchenne muscular dystrophy: trends of an ongoing study, *Brain & Dev.*, 17 Suppl: 39-43, 1995.
Reuser et al., Uptake and Stability of Human and Bovine Acid α-Glucosidase in Cultured Fibroblasts and Skeletal Muscle Cells from Glycogenosis Type II Patients, *Experimental Cell Research*, 155: 178-189, 1984.
Roberts et al., Direct detection of dystrophin gene rearrangements by analysis of dystrophin mRNA in peripheral blood lymphocytes, *Am. J. Hum. Genet.*, 49(2): 298-310, 1991.
Roberts et al., Exon structure of the human dystrophin gene, *Genomics*, 1993, 16(2): 536-538, 1993.
Roberts et al., Direct diagnosis of carriers of Duchenne and Becker muscular dystrophy by amplification of lymphocyte RNA, *Lancet*, 336: 1523-1526, 1990.
Roberts et al., Searching for the 1 in 2,400,000: a review of dystrophin gene point mutations, *Human Mutation*, 4: 1-11, 1994.
Rolland et al., Overactivity of exercise-sensitive cation channels and their impaired modulation by IGF-1 in mdx native muscle fibers: beneficial effect of pentoxifylline. *Neurobiology of Disease*, 24(3): 466-474, 2006.
Rosen et al., Combination Chemotherapy and Radiation Therapy in the Treatment of Metastatic Osteogenic Sarcoma, *Cancer* 35: 622-630, 1975.
Samoylova et al., Elucidation of muscle-binding peptides by phage display screening, *Muscle & Nerve*,22: 460-466, Apr. 1999.
Sarepta Therapeutics, Inc., Sarepta Therapeutics and University of Western Australia Announce Exclusive Worldwide Licensing Agreement for Exon-Skipping Program in Duchenne Muscular Dystrophy, *News Release*, EP1619249, 3 pages, Nov. 4, 2013.
Scanlon, Anti-genes: siRNA, ribozymes, and antisense, *Curr. Pharmaceutical Biotechnology*, 5: 415-420, 2004.
Segalat et al., CAPON expression in skeletal muscle is regulated by position, repair, NOS activity, and dystrophy, *Exp. Cell Research*, 302(2): 170-179, 2005.
Sertic et al., Deletion screening of Duchenne/Becker muscular dystrophy gene in Croatian population, *Coll. Antropol.*, 1:151-156, 1997.
Shapiro and Senapathy, RNA splice junctions of different classes of eukaryotes: sequence statistics and functional implications in gene expression. *Nucleic Acids Research*, 15(17): 7155-7174, 1987.

(56) References Cited

OTHER PUBLICATIONS

Sherratt et al., Exon Skipping and Translation in Patients with Frameshift Deletions in the Dystrophin Gene, *Am. J. Hum. Genet*, 53:1007-1015, 1993.
Shiga et al., Disruption of the Splicing Enhancer Sequence within Exon 27 of the Dystrophin Gene by a Nonsense Mutation Induces Partial Skipping of the Exon and is Responsible for Becker Muscular Dystrophy, *J. Clin. Invest.*, 100(9): 2204-10, Nov. 1997.
Simoes-Wust et al., bcl-xL Antisense Treatment Induces Apoptosis in Breast Carcinoma Cells, *Int. J. Cancer*,87: 582-590, 2000.
Smith et al., Muscle-specific peptide #5, Mar. 23, 1999. From http://www.ebi.ac.uk/cgi-bin/epo/epofetch?AAW89659, downloaded Jul. 16, 2007. XP 002442550.
Sterrenburg et al., Gene expression of profiling highlights defective myogenesis in DMD patients and a possible role for bone morphogenetic protein 4, *Neurobiology of Disease*, 23(1): 228-236, 2006.
Summerton et al., Morpholino Antisense Oligomers: Design, Preparation, and Properties, *Antisense & Nucleic Acid Drug Development*, 7: 187-195, 1997.
Surono et al., Chimeric RNA/ethylene-Bridged Nucleic Acids Promote Dystrophin Expression in Myocytes of Duchenne Muscular Dystrophy by Inducing Skipping of the Nonsense Mutation-Encoding Exon, *Human Gene Therapy*, 15:749-757, Aug. 2004.
Surono et al., Six Novel Transcripts that Remove a Huge Intron Ranging from 250 to 800 kb are Produced by Alternative Splicing of the 5' Region of the Dystrophin Gene in Human Skeletal Muscle, *BBRC*, 239:895-899, 1997.
Suter et al., Double-target antisense U7 snRNAs promote efficient skipping of an aberrant exon in three human B-thalassemic mutations, *Human Molecular Genetics*, 8(13): 2415-2423, 1999.
Suwanmanee et al., Restoration of Human β-Globin Gene Expression in Murine and Human IVS2-654 Thalassemic Erythroid Cells by Free Uptake of Antisense Oligonucleotides, *Mol. Pharmacology* 62(3):545-553, 2002.
Takashima et al., Oligonucleotides Against a Splicing Enhancer Sequence Led to Dystrophin Production in Muscle Cells From a Duchenne Muscular Dystrophy Patient, *Brain & Development*, 23: 788-790, 2001.
Takeshima et al, Intravenous Infusion of an Antisense Oligonucleotide Results in Exon Skipping in Muscle Dystrophin mRNA of Duchenne Muscular Dystrophy. *Pediatric Res*, 59(5):690-694, 2006.
Takeshima et al., Expression of Dystrophin Protein in Cultured Duchenne Muscular Dystrophy Cells by Exon Skipping Induced by Antisense Oligonucleotide, (Abstract); *Abstract of the Japan Society of Human Genetics General Meeting Program*, 8 pages, Nov. 17-19, 1999.
Takeshima, et al., Modulation of In Vitro Splicing of the Upstream Intron by Modifying an Intra-Exon Sequence Which is Deleted from the Dystrophin Gene in Dystrophin Kobe, *J. Clin. Invest.*, 95:515-520, Feb. 1995.
Tanaka, et al., Polypurine Sequences within a Downstream Exon Function as a Splicing Enhancer, *Molecular and Cellular Biology*, 14(2):1347-1354, Feb. 1994.
Thanh et al., Characterization of revertant muscle fibers in Duchenne muscular dystrophy, using exon-specific monoclonal antibodies against dystrophin, *Am. J. Hum. Genet.* 56:725-731, 1995.
Tian and Kole, Selection of novel exon recognition elements from a pool of random sequences, *Mol Cell Biol*, 15(11): 6291-6298, Nov. 1995.
Tsuchida, Peptides, Proteins & Antisense: the role of myostatin and bone morphogenetic proteins in muscular disorders, *Expert Opinion of Biologica Therapy*, 6(2):147-153, 2006.
Van Deutekom et al., Advances in Duchenne Muscular Dystrophy Gene Therapy *Nat Rev Genet*, 4(10): 774-783, Oct. 2003.
Van Deutekom et al., Antisense-induced exon skipping restores dystrophin expression in DMD patient derived muscle cells, *Hum Mol Genet.*, 10(15): 1547-1554, 2001.
Van Deutekom et al., Local Dystrophin Restoration with Antisense Oligonucleotide PRO051, *N. England J. Med.*, 357: 2677-2686, 2007.
Van Ommen, The Therapeutic Potential of Antisense-Mediated Exon-Skipping, *Curr Opin Mol. Ther* ,10(2) 140-149, 2008.
Van Vliet, et al., Assessment of the feasibility of exon 45-55 multiexon skipping for duchenne muscular dystrophy, *BMC Medical Genetics*, 9:105 (7 pages), 2008.
Varani et al., The G•U wobble base pair, *EMBO Reports*, 1(1): 18-23, 2000.
Verhaart et al., Prednisolone treatment does not interfere with 2'-O-methyl phosphorothioate antisense-mediated exon skipping in Duchenne muscular dystrophy. *Hum Gene Ther*. 23(3):262-73, Mar. 2012; Epub Jan. 26, 2012.
Verreault, et al., Gene silencing in the development of personalized cancer treatment: the targets, the agents and the delivery systems, *Curr. Gene Therapy*, 6: 505-553, 2006.
Vickers, et al., Efficient reduction of target RNAs by small interfering RNA and RNase H-dependent antisense agents, A comparative analysis, *J. Biol. Chem.*, 278(9): 7108-7118, 2003.
Vossius & Partners, Grounds of Appeal filed in the opposition proceeding of EP1619249, dated Aug. 23, 2013, 41 pages.
Vossius & Partners, Reply of the Opponent to the Grounds of Appeal, dated Jan. 8, 2014, 31 pages.
Wang et al., Adeno-associated virus vector carrying human minidystrophin genes effectively ameliorates muscular dystrophy in mdx mouse model, PNAS, 97(25):13714-13719, Dec. 5, 2000.
Watakabe et al., The role of exon sequences in splice site selection, Genes & Development, 7: 407-418, 1993.
Weiler et al., Identical mutation in patients with limb girdle muscular dystrophy type 2B or Miyoshi myopathy suggests a role for modifier gene(s), *Human Molecular Genetics*, 8(5): 871-877, 1999.
Weisbart et al., Cell type specific targeted intracellular delivery into muscle of a monoclonal antibody that binds myosin llb., *Molecular Immunology*, 39(13): 783-789, Mar. 2003 (Abstract).
Wells et al., Enhanced in Vivo Delivery of Antisense Oligonucleotide to Restore Dystrophin Expression in Adult MDX Mouse Muscle, FEBS Letters, 552: 145-149, 2003.
Wheway and Roberts, The Dystrophin Lymphocyte promoter revisited: 4.5-megabase intron, or artefact? *Neuromuscular Disorders*,13:17-20, 2003.
Wilton et al., Antisense oligonucleotides, exon skipping and the dysrophin gene transcript, *Acta Myologica*, XXIV:222-229, 2005.
Wilton et al., Specific removal of the nonsense mutation from the mdx dystrophin protein mRNA using antisense oligonucleotides. Neuromuscular Disorders, 9: 330-338, 1999.
Wilton et al., Antisense oligonucleotide-induced exon skipping across the human dystrophin gene transcript, Mol Ther,15(7):1288-1296, Jul. 2007.
Wilton, Declaration of Dr. Steve Wilton in Support of Appeal of Opposition Decision to Maintain EP 1619249, dated Aug. 21, 2013, 25 pages.
Yen et al., Sequence-Specific Cleavage of Huntingtin mRNA by Catalytic DNA, *Annals of Neurology*, 46(3): 366-373, Sep. 1999.
Yu et al., A hairpin ribozyme inhibits expression of diverse strains of human immunodeficiency virus type 1, *Proc. Natl. Acad. Sci. USA*, 90: 6340-6344, Jul. 1993.
Zhang et al., Efficient expression of naked dna delivered intraarterially to limb muscles of nonhuman primates., *Hum. Gene. Ther.*, 12(4): 427-438, Mar. 1, 2001 (Abstract).
Zhou et al., Current understanding of dystrophin-related muscular dystrophy and therapeutic challenges ahead, *Chinese Medical Journal*, 119(16): 1381-1391, 2006.
Bionity, Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.
Biopharmaceutiques, Biopharmaceutiques, Merging Pharma & Biotech, Edition 48, Jan. 10, 2008. http://www.biopharmaceutiques.com/en/num>, visited Jan. 11, 2008.
GenBank, GenBank accession No. AZ993191.1, 2MO278E12F mouse 10kb plasmid UUGC2M library Mus muscu genomic clone

(56) References Cited

OTHER PUBLICATIONS

UUGC2MO278E12F, genomic survey sequence, entry created and last updated on Apr. 27, 2001, 2 pages.
GenBank, GenBank accession No. EW162121.1, rfat0126_k17.y1 fat Sus scrofa cDNA5-, mRNA sequence, entry created on Aug. 13, 2007, last updated on Mar. 3, 2011, 2 pages.
Medical News Today, New Clinical Trial Results Show How Personalized Medicine Will Alter Treatment of Genetic Disorders, *Medical News Today*, Dec. 29, 2007, 2 pages, http://www.medicalnewstoday.com/article/92777.php.
Leiden, University Medical Center and Prosensa B.V. Announce New England Journal of Medicine Publication of First Successful Clinical Study with RNA-based Therapeutic PRO051 in Duchenne Muscular Dystrophy, Dec. 27, 2007, 2 pages.
Vermylen, Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided), 5 pages.
Prosensa, Letter from Prosensa Therapeutics B.V. to Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy, 2 pages.
Red Orbit News, LUMC and Prosensa report positive results of DMD study, Pharmaceutical Business Review Online, dated Dec. 28, 2007, http://www.pharmaceutical-business-review.com/article_news_print.asp?guid=8462FD44-F35D-4EOB-BC, 1 page.
TREAT-NMD Neuromuscular Network, TREAT-NMD Neuromuscular Network, Newsletter No. 24, Jan. 11, 2008, 6 pages.
Australia Patent Office, Office Action for Australian Application No. 2009240879, dated Jun. 22, 2011, 3 pages.
Canadian Patent Office, Office Action for Canadian Application No. 2,524,255, dated Jul. 6, 2011, 2 pages.
European Patent Office, European Search Report Annex—Application No. EP03077205, dated Nov. 19, 2003, 1 page.
European Patent Office, Partial European Search Report—Application No. EP03077205, dated Dec. 10, 2003, 2 pages.
European Patent Office, Office Action—Application No. EP05076770.6, dated Jan. 29, 2007, 5 pages.
U.S. Patent Office, Office Action for U.S. Appl. No. 10/395,031, dated Jul. 8, 2005, 20 pages.
U.S. Patent Office, Office Action for U.S. Appl. No. 10/395,031, dated Feb. 6, 2006, 16 pages.
U.S. Patent Office, Office Action for U.S. Appl. No. 10/395,031, dated Nov. 30, 2006, 15 pages.
U.S. Patent Office, Office Action for U.S. Appl. No. 11/233,507, dated Jun. 15, 2007, 16 pages.
U.S. Patent Office Office, Action for U.S. Appl. No. 10/395,031, dated Aug. 23, 2007, 35 pages.
U.S. Patent Office, Office Action for U.S. Appl. No. 11/233,507, dated Mar. 19, 2008, 12 pages.
U.S. Patent Office, Office Action for U.S. Appl. No. 10/395,031, dated May 30, 2008, 44 pages.
U.S. Patent Office, Office Action for U.S. Appl. No. 11/233,507, dated Nov. 12, 2008, 17 pages.
U.S. Patent Office, Office Action for U.S. Appl. No. 11/233,495, dated Dec. 1, 2008, 14 pages.
U.S. Patent Office, Office Action for U.S. Appl. No. 10/395,031, dated Apr. 2, 2009, 26 pages.
U.S. Patent Office, Office Action of U.S. Appl. No. 11/982,285, dated May 4, 2009, 16 pages.
U.S. Patent Office, Office Action for U.S. Appl. No. 11/233,507, dated May 29, 2009, 17 pages.
U.S. Patent Office, Office Action for U.S. Appl. No. 11/233,495, dated Jun. 25, 2009, 11 pages.
U.S. Patent Office, Office Action for U.S. Appl. No. 11/982,285, dated Sep. 18, 2009, 22 pages.
U.S. Patent Office, Office Action for U.S. Appl. No. 10/395,031, dated Oct. 16, 2009, 7 pages.
European Patent Office, Notice of Opposition filed against EP1619249, dated Jun. 23, 2009, 47 pages.
International Searching Authority, International Preliminary Report on Patentability, International Application No. PCT/EP2007/054842, dated Nov. 21, 2008, together with the Written Opinion, 8 pages.
International Searching Authority, International Preliminary Examination Report, International Application No. PCT/NL01/00697, dated Aug. 1, 2002, 2 pages.
International Searching Authority, International Search Report, International Application No. PCT/NL01/00697, dated Dec. 21, 2001, 2 pages.
International Searching Authority, International Search Report, International Application No. PCT/NL2004/000196, dated Dec. 10, 2004, 7 pages.
International Searching Authority, International Search Report, International Application No. PCT/NL2006/000209, dated Oct. 5, 2006, 4 pages.
International Searching Authority, International Search Report for PCT/EP2007/054842, dated Aug. 21, 2007, 3 pages.
International Searching Authority, International Search Report, International Application No. PCT/NL 2008/050475, dated Jun. 25, 2009, 30 pages.
International Searching Authority, International Search Report, International Application No. PCT/NL 2008/050470, dated Jul. 2, 2009, 4 pages.
International Searching Authority, International Search Report for PCT/NL2009/050006 dated Jul. 31, 2009, 5 pages.
International Searching Authority, International Search Report, International Application No. PCT/NL 2008/050673, dated Sep. 2, 2009, 8 pages.
International Searching Authority, International Search Report for PCT/NL2009/050113, dated Jun. 30, 2010, 8 pages.
Nederlandsch Octrooibureau, Patentee's response during prosecution of opposed patent, dated Jan. 27, 2010, 41 pages.
Mewburn Ellis LLP, Request for an Opinion under Section 74(A) in relation to Patent No. EP (UK) 1 619 249B in the name of Academisch Ziekenhuis Leiden, opinion issued on Jun. 4, 2009, 14 pages.
Mewburn Ellis LLP, Request for UK IPO Opinion (Section 74A & Rule 93)—EP(UK) 1619249 dated Mar. 9, 2009, 24 pages.
Third Party, Third Party's Statement for Japan Appl. No. 2002-529499, dated Oct. 29, 2010, 28 pages.
Nederlandsch Octrooibureau, Exon 46 Alignment—EP1619249, 1 page, Aug. 23, 2013.
Nederlandsch Octrooibureau, Exon 53 Alignment—EP1619249, 1 page, Aug. 23, 2013.
Nederlandsch Octrooibureau, Comparative analysis of AONs for inducing the skipping of exon 45 or 53 from thedystrophin gene in human control muscle cells, EP1619249, 3 pages, Aug. 23, 2013.
van Deutekom, Declaration of Dr. JCT van Deutekom, EP1619249, 2 pages, Aug. 23, 2013.
Nederlandsch Octrooibureau, Exon 45 Alignment—EP1619249, 1 page, Aug. 23, 2013.
Krainer, Declaration of Dr. Adrian Krainer (submitted in Third Party's Stmt for JP Appl. No. 2002-529499, dated Oct. 29, 2010), 7 pages.
Cavanaugh, Third-Party Submission Under 35 U.S.C. §122(e) and 37 C.F.R. §1.290 for U.S. Appl. No. 11/233,495, 6 pages, Jun. 5, 2013.
van Deutekom, Declaration of Dr. JCT van Deutekom—EP1619249, 6 pages, Jan. 7, 2014.
Schnell, Declaration of Dr. Fred Schnell in Support of Appeal of the Opposition Division's Decision to Maintain EP-B1 1 619 249 in amended form, 6 pages, Jan. 7, 2014.
Onlo Nederlandsch Octrooibureau, Schematic of dystrophin exon 53 with alignment of SES/AON, EP1619249, 1 page, Jan. 8, 2014.
Onlo Nederlandsch Octrooibureau, Comparative Analysis of AONs for inducing the skipping of exon 53 from the dystrophin gene in human control muscle cells, EP1619249, 3 pages, Jan. 8, 2014.

(56) References Cited

OTHER PUBLICATIONS

Onlo Nederlandsch Octrooibureau, Alignments of AON exon 53, EP1619249, 1 page, Jan. 8, 2014.
Aartsma-Rus et al., "Guidelines for Antisense Oligonucleotide Design and Insight Into Splice-modulating Mechanisms," Molecular Therapy, vol. 17, No. 3, Mar. 2009, pp. 548-553, (published online Sep. 23, 2008), (attached Supplementary Table, 7 pages).
Heemskerk et al., "In vivo comparison of 2'-$O$-methyl phosphorothioate and morpholino antisense oligonucleotides for Duchenne muscular dystrophy exon skipping," The Journal of Gene Medicine, vol. 11, Mar. 2009, pp. 257-266, (published online Jan. 12, 2009).
Popplewell et al., Poster of Design of Phosphorodiamidate Morpholino Oligomers (PMOs) for the Induction of Exon Skipping of the Human DMD Gene, $5^{th}$ Annual Conference of the British Society for Gene & Cell Therapy, Apr. 7-9, 2008, 1 page.
Popplewell et al., "Design of Phosphorodiamidate Morpholino Oligomers (PMOs) for the Induction of Exon Skipping of the Human DMD Gene," published Oct. 15, 2008, Abstract, 1 page.
Popplewell et al., "Design of Phosphorodiamidate Morpholino Oligomers (PMOs) for the Induction of Exon Skipping of the Human DMD Gene," Molecular Therapy, vol. 17, No. 3, Mar. 2009, pp. 554-561, (published online Jan. 13, 2009), (attached Supplementary Table 1, 1 page).
Popplewell, Information Disclosure Statement for U.S. Appl. No. 14/045,841, filed Sep. 1, 2015, 3 pages, (attached non-patent literature document, 1 page).
Wright et al., Opposition to EP 2 322 637, Sep. 24, 2015, 28 pages.
Wu et al., "Targeted Skipping of Human Dystrophin Exons in Transgenic Mouse Model Systemically for Antisense Drug Development," PLoS ONE, vol. 6, issue 5, May 17, 2011, 11 pages.
Sironi et al., "The dystrophin gene is alternatively spliced throughout its coding sequence," FEBS Letters 517, pp. 163-166, 2002.

\* cited by examiner

Screening of Exon 45 specific AONs PS220-225 in Human Control Myotubes

Screening of Exon 45 specific PS220 at Increasing Concentrations in Human Control Myotubes Comparison of 17-mer AON45-5 vs. 25-mer PS220 in Human Control Myotubes

METHODS AND MEANS FOR EFFICIENT SKIPPING OF EXON 45 IN DUCHENNE MUSCULAR DYSTROPHY PRE-MRNA

PRIORITY

This application is a U.S. continuation patent application Ser. No. 14/200,251 filed Mar. 7, 2014, which is a U.S. continuation patent application of U.S. patent application Ser. No. 14/134,971 filed Dec. 19, 2013 which is a U.S. continuation patent application of U.S. patent application Ser. No. 14/097,210 filed Dec. 4, 2013, which is a U.S. continuation patent application of U.S. patent application Ser. No. 13/094,548 filed Apr. 26, 2011, which is a U.S. continuation patent application of PCT/NL2009/050006, filed on Jan. 13, 2009, which claims priority to PCT/NL2008/050673, filed on Oct. 27, 2008, the entirety of which is incorporated herein by reference.

SEQUENCE LISTING

The attached sequence listing is hereby incorporated by reference.

FIELD

The invention relates to the field of genetics, more specifically human genetics. The invention in particular relates to human Duchenne Muscular Dystrophy.

BACKGROUND OF THE INVENTION

Myopathies are disorders that result in functional impairment of muscles. Muscular dystrophy (MD) refers to genetic diseases that are characterized by progressive weakness and degeneration of skeletal muscles. Duchenne muscular dystrophy (DMD) and Becker muscular dystrophy (BMD) are the most common childhood forms of muscular dystrophy. They are recessive disorders and because the gene responsible for DMD and BMD resides on the X-chromosome, mutations mainly affect males with an incidence of about 1 in 3500 boys.

DMD and BMD are caused by genetic defects in the DMD gene encoding dystrophin, a muscle protein that is required for interactions between the cytoskeleton and the extracellular matrix to maintain muscle fiber stability during contraction. DMD is a severe, lethal neuromuscular disorder resulting in a dependency on wheelchair support before the age of 12 and DMD patients often die before the age of thirty due to respiratory- or heart failure. In contrast, BMD patients often remain ambulatory until later in life, and have near normal life expectancies. DMD mutations in the DMD gene are mainly characterized by frame shifting insertions or deletions or nonsense point mutations, resulting in the absence of functional dystrophin. BMD mutations in general keep the reading frame intact, allowing synthesis of a partly functional dystrophin.

During the last decade, specific modification of splicing in order to restore the disrupted reading frame of the DMD transcript has emerged as a promising therapy for Duchenne muscular dystrophy (DMD) (van Ommen, van Deutekom, Aartsma-Rus, Curr Opin Mol Ther. 2008; 10(2):140-9, Yokota, Duddy, Partidge, Acta Myol. 2007; 26(3):179-84, van Deutekom et al., N Engl J Med. 2007; 357(26):2677-86. Using antisense oligonucleotides (AONs) interfering with splicing signals the skipping of specific exons can be induced in the DMD pre-mRNA, thus restoring the open reading frame and converting the severe DMD into a milder BMD phenotype (van Deutekom et al. Hum Mol Genet. 2001; 10: 1547-54; Aartsma-Rus et al., Hum Mol Genet 2003; 12(8):907-14.). In vivo proof-of-concept was first obtained in the mdx mouse model, which is dystrophin-deficient due to a nonsense mutation in exon 23. Intramuscular and intravenous injections of AONs targeting the mutated exon 23 restored dystrophin expression for at least three months (Lu et al. Nat Med. 2003; 8: 1009-14; Lu et al., Proc Natl Acad Sci USA. 2005; 102(1):198-203). This was accompanied by restoration of dystrophin-associated proteins at the fiber membrane as well as functional improvement of the treated muscle. In vivo skipping of human exons has also been achieved in the hDMD mouse model, which contains a complete copy of the human DMD gene integrated in chromosome 5 of the mouse (Bremmer-Bout et al. Molecular Therapy. 2004; 10: 232-40; 't Hoen et al. J Biol Chem. 2008; 283: 5899-907).

As the majority of DMD patients have deletions that cluster in hotspot regions, the skipping of a small number of exons is applicable to relatively large numbers of patients. The actual applicability of exon skipping can be determined for deletions, duplications and point mutations reported in DMD mutation databases such as the Leiden DMD mutation database available at www.dmd.nl. Therapeutic skipping of exon 45 of the DMD pre-mRNA would restore the open reading frame of DMD patients having deletions including but not limited to exons 12-44, 18-44, 44, 46, 46-47, 46-48, 46-49, 46-51, 46-53, 46-55, 46-59, 46-60 of the DMD pre-mRNA, occurring in a total of 16% of all DMD patients with a deletion (Aartsma-Rus and van Deutekom, 2007, Antisense Elements (Genetics) Research Focus, 2007 Nova Science Publishers, Inc). Furthermore, for some DMD patients the simultaneous skipping of one of more exons in addition to exon 45, such as exons 51 or 53 is required to restore the correct reading frame. None-limiting examples include patients with a deletion of exons 46-50 requiring the co-skipping of exons 45 and 51, or with a deletion of exons 46-52 requiring the co-skipping of exons 45 and 53.

Recently, a first-in-man study was successfully completed where an AON inducing the skipping of exon 51 was injected into a small area of the tibialis anterior muscle of four DMD patients. Novel dystrophin expression was observed in the majority of muscle fibers in all four patients treated, and the AON was safe and well tolerated (van Deutekom et al. N Engl J Med. 2007; 357: 2677-86).

Most AONs studied contain up to 20 nucleotides, and it has been argued that this relatively short size improves the tissue distribution and/or cell penetration of an AON. However, such short AONs will result in a limited specificity due to an increased risk for the presence of identical sequences elsewhere in the genome, and a limited target binding or target affinity due to a low free energy of the AON-target complex. Therefore the inventors decided to design new and optionally improved oligonucleotides that would not exhibit all of these drawbacks.

DESCRIPTION OF THE INVENTION

Method

In a first aspect, the invention provides a method for inducing and/or promoting skipping of exon 45 of DMD pre-mRNA in a patient, preferably in an isolated cell of said patient, the method comprising providing said cell and/or said patient with a molecule that binds to a continuous stretch of at least 21 nucleotides within said exon.

Accordingly, a method is herewith provided for inducing and/or promoting skipping of exon 45 of DMD pre-mRNA, preferably in an isolated cell of a patient, the method comprising providing said cell and/or said patient with a molecule that binds to a continuous stretch of at least 21 nucleotides within said exon.

It is to be understood that said method encompasses an in vitro, in vivo or ex vivo method.

As defined herein a DMD pre-mRNA preferably means the pre-mRNA of a DMD gene of a DMD or BMD patient. The DMD gene or protein corresponds to the dystrophin gene or protein.

A patient is preferably intended to mean a patient having DMD or BMD as later defined herein or a patient susceptible to develop DMD or BMD due to his or her genetic background.

Exon skipping refers to the induction in a cell of a mature mRNA that does not contain a particular exon that is normally present therein. Exon skipping is achieved by providing a cell expressing the pre-mRNA of said mRNA with a molecule capable of interfering with sequences such as, for example, the splice donor or splice acceptor sequence that are both required for allowing the enzymatic process of splicing, or a molecule that is capable of interfering with an exon inclusion signal required for recognition of a stretch of nucleotides as an exon to be included in the mRNA. The term pre-mRNA refers to a non-processed or partly processed precursor mRNA that is synthesized from a DNA template in the cell nucleus by transcription.

Within the context of the invention inducing and/or promoting skipping of an exon as indicated herein means that at least 1%, 10%, 20%, 30%, 40%, 50%, 60%, 70%, 80%, 90% or more of the DMD mRNA in one or more (muscle) cells of a treated patient will not contain said exon. This is preferably assessed by PCR as described in the examples.

Preferably, a method of the invention by inducing or promoting skipping of exon 45 of the DMD pre-mRNA in one or more cells of a patient provides said patient with a functional dystrophin protein and/or decreases the production of an aberrant dystrophin protein in said patient. Therefore a preferred method is a method, wherein a patient or a cell of said patient is provided with a functional dystrophin protein and/or wherein the production of an aberrant dystrophin protein in said patient or in a cell of said patient is decreased Decreasing the production of an aberrant dystrophin may be assessed at the mRNA level and preferably means that 99%, 90%, 80%, 70%, 60%, 50%, 40%, 30%, 20%, 10%, 5% or less of the initial amount of aberrant dystrophin mRNA, is still detectable by RT PCR. An aberrant dystrophin mRNA or protein is also referred to herein as a non-functional dystrophin mRNA or protein. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein.

Increasing the production of a functional dystrophin in said patient or in a cell of said patient may be assessed at the mRNA level (by RT-PCR analysis) and preferably means that a detectable amount of a functional dystrophin mRNA is detectable by RT PCR. In another embodiment, 1%, 5%, 10%, 20%, 30%, 40%, 50%, 60%, 70%, 80%, 90% or more of the detectable dystrophin mRNA is a functional dystrophin mRNA.

Increasing the production of a functional dystrophin in said patient or in a cell of said patient may be assessed at the protein level (by immunofluorescence and western blot analyses) and preferably means that a detectable amount of a functional dystrophin protein is detectable by immunofluorescence or western blot analysis. In another embodiment, 1%, 5%, 10%, 20%, 30%, 40%, 50%, 60%, 70%, 80%, 90% or more of the detectable dystrophin protein is a functional dystrophin protein.

As defined herein, a functional dystrophin is preferably a wild type dystrophin corresponding to a protein having the amino acid sequence as identified in SEQ ID NO: 1. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO:1. In other words, a functional dystrophin is a dystrophin which exhibits at least to some extent an activity of a wild type dystrophin. "At least to some extent" preferably means at least 10%, 20%, 30%, 40%, 50%, 60%, 70%, 80%, 90%, 95% or 100% of a corresponding activity of a wild type functional dystrophin. In this context, an activity of a functional dystrophin is preferably binding to actin and to the dystrophin-associated glycoprotein complex (DGC) (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). Binding of dystrophin to actin and to the DGC complex may be visualized by either co-immunoprecipitation using total protein extracts or immunofluorescence analysis of cross-sections, from a muscle biopsy, as known to the skilled person.

Individuals or patients suffering from Duchenne muscular dystrophy typically have a mutation in the DMD gene that prevent synthesis of the complete dystrophin protein, i.e of a premature stop prevents the synthesis of the C-terminus. In Becker muscular dystrophy the DMD gene also comprises a mutation compared to the wild type gene but the mutation does typically not induce a premature stop and the C-terminus is typically synthesized. As a result a functional dystrophin protein is synthesized that has at least the same activity in kind as the wild type protein, not although not necessarily the same amount of activity. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). Exon-skipping for the treatment of DMD is typically directed to overcome a premature stop in the pre-mRNA by skipping an exon in the rod-shaped domain to correct the reading frame and allow synthesis of the remainder of the dystrophin protein including the C-terminus, albeit that the protein is somewhat smaller as a result of a smaller rod domain. In a preferred embodiment, an individual having DMD and being treated by a method as defined herein will be provided a dystrophin which exhibits at least to some extent an activity of a wild type dystrophin. More preferably, if said individual is a Duchenne patient or is suspected to be a Duchenne patient, a functional dystrophin is a dystrophin of an individual having BMD: typically said dystrophin is able to interact with both actin and the DGC, but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The central rod-shaped domain of wild type dystrophin comprises 24 spectrin-like repeats (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). For example, a central rod-shaped domain of a dystrophin as provided herein may comprise 5 to 23, 10 to 22 or 12 to 18 spectrin-like repeats as long as it can bind to actin and to DGC.

A method of the invention may alleviate one or more characteristics of a muscle cell from a DMD patient comprising deletions including but not limited to exons 12-44, 18-44, 44, 46, 46-47, 46-48, 46-49, 46-51, 46-53, 46-55, 46-59, 46-60 of the DMD pre-mRNA of said patient (Aartsma-Rus and van Deutekom, 2007, Antisense Elements (Genetics) Research Focus, 2007 Nova Science Publishers, Inc) as well as from DMD patients requiring the simultaneous skipping of one of more exons in addition to exon 45 including but not limited to patients with a deletion of exons 46-50 requiring the co-skipping of exons 45 and 51, or with a deletion of exons 46-52 requiring the co-skipping of exons 45 and 53.

In a preferred method, one or more symptom(s) or characteristic(s) of a myogenic cell or muscle cell from a DMD patient is/are alleviated. Such symptoms or characteristics may be assessed at the cellular, tissue level or on the patient self.

An alleviation of one or more symptoms or characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

The improvement of muscle fiber function, integrity and/or survival may also be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in Hodgetts et al (Hodgetts S., et al, (2006), Neuromuscular Disorders, 16: 591-602.2006). A detectable decrease in creatine kinase may mean a decrease of 5%, 10%, 20%, 30%, 40%, 50%, 60%, 70%, 80%, 90% or more compared to the concentration of creatine kinase in a same DMD patient before treatment.

A detectable decrease of necrosis of muscle fibers is preferably assessed in a muscle biopsy, more preferably as described in Hodgetts et al (Hodgetts S., et al, (2006), Neuromuscular Disorders, 16: 591-602.2006) using biopsy cross-sections. A detectable decrease of necrosis may be a decrease of 5%, 10%, 20%, 30%, 40%, 50%, 60%, 70%, 80%, 90% or more of the area wherein necrosis has been identified using biopsy cross-sections. The decrease is measured by comparison to the necrosis as assessed in a same DMD patient before treatment.

A detectable increase of the homogeneity of the diameter of muscle fibers is preferably assessed in a muscle biopsy cross-section, more preferably as described in Hodgetts et al (Hodgetts S., et al, (2006), Neuromuscular Disorders, 16: 591-602.2006). The increase is measured by comparison to the homogeneity of the diameter of muscle fibers in a muscle biopsy cross-section of a same DMD patient before treatment.

An alleviation of one or more symptoms or characteristics may be assessed by any of the following assays on the patient self: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (Manzur A Y et al, (2008), Glucocorticoid corticosteroids for Duchenne muscular dystrophy (review), Wiley publishers, The Cochrane collaboration.) gives an extensive explanation of each of these assays. For each of these assays, as soon as a detectable improvement or prolongation of a parameter measured in an assay has been found, it will preferably mean that one or more symptoms of Duchenne Muscular Dystrophy has been alleviated in an individual using a method of the invention. Detectable improvement or prolongation is preferably a statistically significant improvement or prolongation as described in Hodgetts et al (Hodgetts S., et al, (2006), Neuromuscular Disorders, 16: 591-602.2006). Alternatively, the alleviation of one or more symptom(s) of Duchenne Muscular Dystrophy may be assessed by measuring an improvement of a muscle fiber function, integrity and/or survival as later defined herein.

A treatment in a method according to the invention may have a duration of at least one week, at least one month, at least several months, at least one year, at least 2, 3, 4, 5, 6 years or more. The frequency of administration of an oligonucleotide, composition, compound of the invention may depend on several parameters such as the age of the patient, the type of mutation, the number of molecules (dose), the formulation of said molecule. The frequency may be ranged between at least once in a two weeks, or three weeks or four weeks or five weeks or a longer time period.

Each molecule or oligonucleotide or equivalent thereof as defined herein for use according to the invention may be suitable for direct administration to a cell, tissue and/or an organ in vivo of individuals affected by or at risk of developing DMD and may be administered directly in vivo, ex vivo or in vitro. An oligonucleotide as used herein may be suitable for administration to a cell, tissue and/or an organ in vivo of individuals affected by or at risk of developing DMD, and may be administered in vivo, ex vivo or in vitro. Said oligonucleotide may be directly or indirectly administrated to a cell, tissue and/or an organ in vivo of an individual affected by or at risk of developing DMD, and may be administered directly or indirectly in vivo, ex vivo or in vitro. As Duchenne muscular dystrophy has a pronounced phenotype in muscle cells, it is preferred that said cells are muscle cells, it is further preferred that said tissue is a muscular tissue and/or it is further preferred that said organ comprises or consists of a muscular tissue. A preferred organ is the heart. Preferably said cells comprise a gene encoding a mutant dystrophin protein. Preferably said cells are cells of an individual suffering from DMD.

A molecule or oligonucleotide or equivalent thereof can be delivered as is to a cell. When administering said molecule, oligonucleotide or equivalent thereof to an individual, it is preferred that it is dissolved in a solution that is compatible with the delivery method. For intravenous, subcutaneous, intramuscular, intrathecal and/or intraventricular administration it is preferred that the solution is a physiological salt solution. Particularly preferred for a method of the invention is the use of an excipient that will further enhance delivery of said molecule, oligonucleotide or functional equivalent thereof as defined herein, to a cell and into a cell, preferably a muscle cell. Preferred excipient are defined in the section entitled "pharmaceutical composition". In vitro, we obtained very good results using polyethylenimine (PEI, ExGen500, MBI Fermentas) as shown in the example.

In a preferred method of the invention, an additional molecule is used which is able to induce and/or promote skipping of a distinct exon of the DMD pre-mRNA of a patient. Preferably, the second exon is selected from: exon 7, 44, 46, 51, 53, 59, 67 of the dystrophin pre-mRNA of a patient. Molecules which can be used are depicted in table 2. Preferred molecules comprise or consist of any of the oligonucleotides as disclosed in table 2. Several oligonucleotides may also be used in combination. This way, inclusion of two or more exons of a DMD pre-mRNA in mRNA produced from this pre-mRNA is prevented. This embodiment is further referred to as double- or multi-exon skipping (Aartsma-Rus A, Janson A A, Kaman W E, et al. Antisense-induced multiexon skipping for Duchenne muscular dystrophy makes more sense. Am J Hum Genet 2004; 74(1):83-92, Aartsma-Rus A, Kaman W E, Weij R, den Dunnen J T, van Ommen G J, van Deutekom J C. Exploring the frontiers of therapeutic exon skipping for Duchenne muscular dystrophy by double targeting within one or multiple exons. Mol Ther 2006; 14(3):401-7). In most cases double-exon skipping results in the exclusion of only the two targeted exons from the dystrophin pre-mRNA. However, in other cases it was found that the targeted exons and the entire region in between said exons in said pre-mRNA were not present in the produced mRNA even when other exons (intervening exons) were present in such region. This multi-skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other.

It is possible to specifically promote the skipping of also the intervening exons by providing a linkage between the two complementary oligonucleotides. Hence, in one embodiment stretches of nucleotides complementary to at least two dystrophin exons are separated by a linking moiety. The at least two stretches of nucleotides are thus linked in this embodiment so as to form a single molecule.

In case, more than one compounds are used in a method of the invention, said compounds can be administered to an individual in any order. In one embodiment said compounds are administered simultaneously (meaning that said compounds are administered within 10 hours, preferably within one hour). This is however not necessary. In another embodiment, said compounds are administered sequentially.

Molecule

In a second aspect, there is provided a molecule for use in a method as described in the previous section entitled "Method". This molecule preferably comprises or consists of an oligonucleotide, Said oligonucleotide is preferably an antisense oligonucleotide (AON) or antisense oligoribonucleotide.

It was found by the present investigators that especially exon 45 is specifically skipped at a high frequency using a molecule that binds to a continuous stretch of at least 21 nucleotides within said exon. Although this effect can be associated with a higher binding affinity of said molecule, compared to a molecule that binds to a continuous stretch of less than 21 nucleotides, there could be other intracellular parameters involved that favor thermodynamic, kinetic, or structural characteristics of the hybrid duplex. In a preferred embodiment, a molecule that binds to a continuous stretch of at least 21, 25, 30, 35, 40, 45, 50 nucleotides within said exon is used.

In a preferred embodiment, a molecule or an oligonucleotide of the invention which comprises a sequence that is complementary to a part of exon 45 of DMD pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% and most preferably up to 100%. "A part of exon 45" preferably means a stretch of at least 21 nucleotides. In a most preferred embodiment, an oligonucleotide of the invention consists of a sequence that is complementary to part of exon 45 dystrophin pre-mRNA as defined herein. Alternatively, an oligonucleotide may comprise a sequence that is complementary to part of exon 45 dystrophin pre-mRNA as defined herein and additional flanking sequences. In a more preferred embodiment, the length of said complementary part of said oligonucleotide is of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Several types of flanking sequences may be used. Preferably, additional flanking sequences are used to modify the binding of a protein to said molecule or oligonucleotide, or to modify a thermodynamic property of the oligonucleotide, more preferably to modify target RNA binding affinity. In another preferred embodiment, additional flanking sequences are complementary to sequences of the DMD pre-mRNA which are not present in exon 45. Such flanking sequences are preferably complementary to sequences comprising or consisting of the splice site acceptor or donor consensus sequences of exon 45. In a preferred embodiment, such flanking sequences are complementary to sequences comprising or consisting of sequences of an intron of the DMD pre-mRNA which is adjacent to exon 45; i.e. intron 44 or 45.

A continuous stretch of at least 21, 25, 30, 35, 40, 45, 50 nucleotides within exon 45 is preferably selected from the sequence:

(SEQ ID NO 2)
5'-CCAGGAUGGCAUUGGGCAGCGGCAAACUGUUGUCAGA

ACAUUGAAUGCAACUGGGGAAGAAAUAAUUCAGCAAUC-3'.

It was found that a molecule that binds to a nucleotide sequence comprising or consisting of a continuous stretch of at least 21, 25, 30, 35, 40, 45, 50 nucleotides of SEQ ID NO.

2 results in highly efficient skipping of exon 45 in a cell provided with this molecule. Molecules that bind to a nucleotide sequence comprising a continuous stretch of less than 21 nucleotides of SEQ ID NO:2 were found to induce exon skipping in a less efficient way than the molecules of the invention. Therefore, in a preferred embodiment, a method is provided wherein a molecule binds to a continuous stretch of at least 21, 25, 30, 35 nucleotides within SEQ ID NO:2. Contrary to what was generally thought, the inventors surprisingly found that a higher specificity and efficiency of exon skipping may be reached using an oligonucleotides having a length of at least 21 nucleotides. None of the indicated sequences is derived from conserved parts of splice-junction sites. Therefore, said molecule is not likely to mediate differential splicing of other exons from the DMD pre-mRNA or exons from other genes.

In one embodiment, a molecule of the invention capable of interfering with the inclusion of exon 45 of the DMD pre-mRNA is a compound molecule that binds to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are for example disclosed in PCT/NL01/00697 and U.S. Pat. No. 6,875,736, which are herein enclosed by reference. Methods for designing RNA-binding Zinc-finger proteins that bind specific nucleotide sequences are disclosed by Friesen and Darby, Nature Structural Biology 5: 543-546 (1998) which is herein enclosed by reference.

In a further embodiment, a molecule of the invention capable of interfering with the inclusion of exon 45 of the DMD pre-mRNA comprises an antisense oligonucleotide that is complementary to and can base-pair with the coding strand of the pre-mRNA of the DMD gene. Said antisense oligonucleotide preferably contains a RNA residue, a DNA residue, and/or a nucleotide analogue or equivalent, as will be further detailed herein below.

A preferred molecule of the invention comprises a nucleotide-based or nucleotide or an antisense oligonucleotide sequence of between 21 and 50 nucleotides or bases, more preferred between 21 and 40 nucleotides, more preferred between 21 and 30 nucleotides, such as 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides or 50 nucleotides.

A most preferred molecule of the invention comprises a nucleotide-based sequence of 25 nucleotides.

In a preferred embodiment, a molecule of the invention binds to a continuous stretch of or is complementary to or is antisense to at least a continuous stretch of at least 21 nucleotides within the nucleotide sequence SEQ ID NO:2.

In a certain embodiment, the invention provides a molecule comprising or consisting of an antisense nucleotide sequence selected from the antisense nucleotide sequences as depicted in Table 1, except SEQ ID NO:68. A molecule of the invention that is antisense to the sequence of SEQ ID NO 2, which is present in exon 45 of the DMD gene preferably comprises or consists of the antisense nucleotide sequence of SEQ ID NO 3; SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66 and/or SEQ ID NO:67.

In a more preferred embodiment, the invention provides a molecule comprising or consisting of the antisense nucleotide sequence of SEQ ID NO 3; SEQ ID NO 4, SEQ ID NO 5, SEQ ID NO 6, SEQ ID NO 7 and/or SEQ ID NO 8.

In a most preferred embodiment, the invention provides a molecule comprising or consisting of the antisense nucleotide sequence of SEQ ID NO 3. It was found that this molecule is very efficient in modulating splicing of exon 45 of the DMD pre-mRNA in a muscle cell.

A nucleotide sequence of a molecule of the invention may contain a RNA residue, a DNA residue, a nucleotide analogue or equivalent as will be further detailed herein below. In addition, a molecule of the invention may encompass a functional equivalent of a molecule of the invention as defined herein.

It is preferred that a molecule of the invention comprises a or at least one residue that is modified to increase nuclease resistance, and/or to increase the affinity of the antisense nucleotide for the target sequence. Therefore, in a preferred embodiment, an antisense nucleotide sequence comprises a or at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, a nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred antisense oligonucleotide according to the invention comprises a 2'-O-alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

A most preferred antisense oligonucleotide according to the invention comprises a 2'-O-methyl phosphorothioate ribose.

A functional equivalent of a molecule of the invention may be defined as an oligonucleotide as defined herein wherein an activity of said functional equivalent is retained to at least some extent. Preferably, an activity of said functional equivalent is inducing exon 45 skipping and providing a functional dystrophin protein. Said activity of said functional equivalent is therefore preferably assessed by detection of exon 45 skipping and quantifying the amount of a functional dystrophin protein. A functional dystrophin is herein preferably defined as being a dystrophin able to bind actin and members of the DGC protein complex. The assessment of said activity of an oligonucleotide is preferably done by RT-PCR or by immunofluorescence or Western blot analysis. Said activity is preferably retained to at least some extent when it represents at least 50%, or at least 60%, or at least 70% or at least 80% or at least 90% or at least 95% or more of corresponding activity of said oligonucleotide the functional equivalent derives from. Throughout this application, when the word oligonucleotide is used it may be replaced by a functional equivalent thereof as defined herein.

It will also be understood by a skilled person that distinct antisense oligonucleotides can be combined for efficiently skipping of exon 45 of the human DMD pre-mRNA. In a preferred embodiment, a combination of at least two antisense oligonucleotides are used in a method of the invention, such as two distinct antisense oligonucleotides, three distinct antisense oligonucleotides, four distinct antisense oligonucleotides, or five distinct antisense oligonucleotides or even more. It is also encompassed by the present invention to combine several oligonucleotides or molecules as depicted in table 1 except SEQ ID NO:68.

An antisense oligonucleotide can be linked to a moiety that enhances uptake of the antisense oligonucleotide in cells, preferably myogenic cells or muscle cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

A preferred antisense oligonucleotide comprises a peptide-linked PMO.

A preferred antisense oligonucleotide comprising one or more nucleotide analogs or equivalents of the invention modulates splicing in one or more muscle cells, including heart muscle cells, upon systemic delivery. In this respect, systemic delivery of an antisense oligonucleotide comprising a specific nucleotide analog or equivalent might result in targeting a subset of muscle cells, while an antisense oligonucleotide comprising a distinct nucleotide analog or equivalent might result in targeting of a different subset of muscle cells. Therefore, in one embodiment it is preferred to use a combination of antisense oligonucleotides comprising different nucleotide analogs or equivalents for modulating skipping of exon 45 of the human DMD pre-mRNA.

A cell can be provided with a molecule capable of interfering with essential sequences that result in highly efficient skipping of exon 45 of the human DMD pre-mRNA by plasmid-derived antisense oligonucleotide expression or viral expression provided by viral-based vector. Such a viral-based vector comprises an expression cassette that drives expression of an antisense molecule as defined herein. Preferred virus-based vectors include adenovirus- or adeno-associated virus-based vectors. Expression is preferably driven by a polymerase III promoter, such as a U1, a U6, or a U7 RNA promoter. A muscle or myogenic cell can be provided with a plasmid for antisense oligonucleotide expression by providing the plasmid in an aqueous solution. Alternatively, a plasmid can be provided by transfection using known transfection agentia such as, for example, LipofectAMINE™ 2000 (Invitrogen) or polyethyleneimine (PEI; ExGen500 (MBI Fermentas)), or derivatives thereof.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of exon 45 of the DMD pre-mRNA.

A preferred AAV-based vector comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of one or more antisense sequences of the invention for inducing skipping of exon 45 of the human DMD pre-mRNA.

Pharmaceutical Composition

If required, a molecule or a vector expressing an antisense oligonucleotide of the invention can be incorporated into a pharmaceutically active mixture or composition by adding a pharmaceutically acceptable carrier.

Therefore, in a further aspect, the invention provides a composition, preferably a pharmaceutical composition comprising a molecule comprising an antisense oligonucleotide according to the invention, and/or a viral-based vector expressing the antisense sequence(s) according to the invention and a pharmaceutically acceptable carrier.

A preferred pharmaceutical composition comprises a molecule as defined herein and/or a vector as defined herein, and a pharmaceutical acceptable carrier or excipient, optionally combined with a molecule and/or a vector which is able to modulate skipping of exon 7, 44, 46, 51, 53, 59, 67 of the DMD pre-mRNA.

Preferred excipients include excipients capable of forming complexes, vesicles and/or liposomes that deliver such a molecule as defined herein, preferably an oligonucleotide complexed or trapped in a vesicle or liposome through a cell membrane. Many of these excipients are known in the art. Suitable excipients comprise polyethylenimine and derivatives, or similar cationic polymers, including polypropyleneimine or polyethylenimine copolymers (PECs) and derivatives, synthetic amphiphils, Lipofectin™, DOTAP and/or viral capsid proteins that are capable of self assembly into particles that can deliver such molecule, preferably an oligonucleotide as defined herein to a cell, preferably a muscle cell. Such excipients have been shown to efficiently deliver (oligonucleotide such as antisense) nucleic acids to a wide variety of cultured cells, including muscle cells. We obtained very good results using polyethylenimine (PEI, ExGen500, MBI Fermentas) as shown in the example. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver a molecule or a compound as defined herein, preferably an oligonucleotide across cell membranes into cells.

In addition to these common nanoparticle materials, the cationic peptide protamine offers an alternative approach to formulate a compound as defined herein, preferably an oligonucleotide as colloids. This colloidal nanoparticle system can form so called proticles, which can be prepared by a simple self-assembly process to package and mediate intracellular release of a compound as defined herein, preferably an oligonucleotide. The skilled person may select and adapt any of the above or other commercially available alternative excipients and delivery systems to package and deliver a compound as defined herein, preferably an oligonucleotide for use in the current invention to deliver said compound for the treatment of Duchenne Muscular Dystrophy in humans.

In addition, a compound as defined herein, preferably an oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an a compound as defined herein, preferably an oligonucleotide from vesicles, e.g. endosomes or lysosomes.

Therefore, in a preferred embodiment, a compound as defined herein, preferably an oligonucleotide are formulated in a medicament which is provided with at least an excipient and/or a targeting ligand for delivery and/or a delivery device of said compound to a cell and/or enhancing its intracellular delivery. Accordingly, the invention also encompasses a pharmaceutically acceptable composition comprising a compound as defined herein, preferably an oligonucleotide and further comprising at least one excipient and/or a targeting ligand for delivery and/or a delivery device of said compound to a cell and/or enhancing its intracellular delivery.

It is to be understood that a molecule or compound or oligonucleotide may not be formulated in one single composition or preparation. Depending on their identity, the skilled person will know which type of formulation is the most appropriate for each compound.

In a preferred embodiment, an in vitro concentration of a molecule or an oligonucleotide as defined herein, which is ranged between 0.1 nM and 1 ☐M is used. More preferably, the concentration used is ranged between 0.3 to 400 nM, even more preferably between 1 to 200 nM. molecule or an oligonucleotide as defined herein may be used at a dose which is ranged between 0.1 and 20 mg/kg, preferably 0.5 and 10 mg/kg. If several molecules or oligonucleotides are used, these concentrations may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, a compound preferably an oligonucleotide and an adjunct compound to be used in the invention to prevent, treat DMD are synthetically produced and administered directly to a cell, a tissue, an organ and/or patients in formulated form in a pharmaceutically acceptable composition or preparation. The delivery of a pharmaceutical composition to the subject is preferably carried out by one or more parenteral injections, e.g. intravenous and/or subcutaneous and/or intramuscular and/or intrathecal and/or intraventricular administrations, preferably injections, at one or at multiple sites in the human body.

Use

In yet a further aspect, the invention provides the use of an antisense oligonucleotide or molecule according to the invention, and/or a viral-based vector that expresses one or more antisense sequences according to the invention and/or a pharmaceutical composition, for inducing and/or promoting splicing of the DMD pre-mRNA. The splicing is preferably modulated in a human myogenic cell or a muscle cell in vitro. More preferred is that splicing is modulated in human a myogenic cell or muscle cell in vivo.

Accordingly, the invention further relates to the use of the molecule as defined herein and/or the vector as defined herein and/or the pharmaceutical composition as defined herein for inducing and/or promoting splicing of the DMD pre-mRNA or for the preparation of a medicament for the treatment of a DMD patient.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a molecule or a viral-based vector or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each embodiment as identified herein may be combined together unless otherwise indicated. All patent and literature references cited in the present specification are hereby incorporated by reference in their entirety.

The following examples are offered for illustrative purposes only, and are not intended to limit the scope of the present invention in any way.

EXAMPLES

Examples 1 and 2

Materials and Methods

AON design was based on (partly) overlapping open secondary structures of the target exon RNA as predicted by the m-fold program (Zuker, M. (2003) Mfold web server for nucleic acid folding and hybridization prediction. *Nucleic Acids Res.*, 31, 3406-3415), and on (partly) overlapping putative SR-protein binding sites as predicted by numerous software programs such as ESEfinder (Cartegni, L. et al. (2003) ESEfinder: A web resource to identify exonic splicing enhancers. *Nucleic Acids Res*, 31, 3568-71; Smith, P. J. et al. (2006) An increased specificity score matrix for the prediction of SF2/ASF-specific exonic splicing enhancers. *Hum. Mol. Genet.*, 15, 2490-2508) that predicts binding sites for the four most abundant SR proteins (SF2/ASF, SC35, SRp40 and SRp55). AONs were synthesized by Prosensa Therapeutics B.V. (Leiden, Netherlands), and contain 2'-O-methyl RNA and full-length phosphorothioate (PS) backbones.

Tissue Culturing, Transfection and RT-PCR Analysis

Myotube cultures derived from a healthy individual ("human control") were obtained as described previously (Aartsma-Rus et al. Hum Mol Genet 2003; 12(8): 907-14). For the screening of AONs, myotube cultures were transfected with 0 to 500 nM of each AON. The transfection reagent polyethylenimine (PEI, ExGen500 MBI Fermentas) was used according to manufacturer's instructions, with 2 µl PEI per µg AON. Exon skipping efficiencies were determined by nested RT-PCR analysis using primers in the exons flanking exon 45. PCR fragments were isolated from agarose gels for sequence verification. For quantification, the PCR products were analyzed using the Agilent DNA 1000 LabChip Kit and the Agilent 2100 bioanalyzer (Agilent Technologies, USA).

Results

Figure 1:
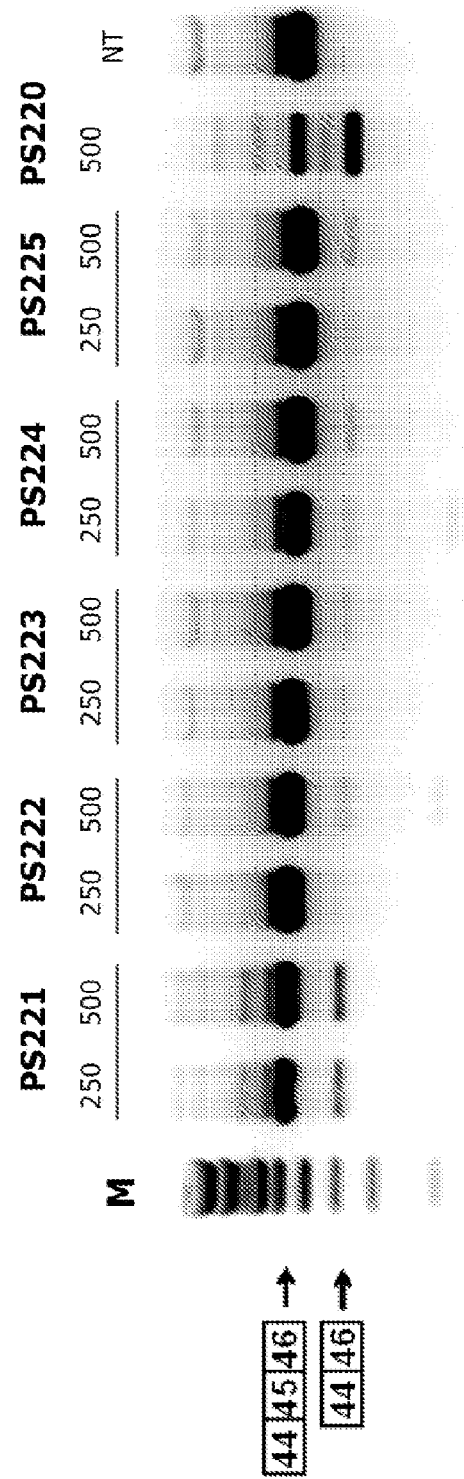
FIG. 1. In human control myotubes, a series of AONs (PS220 to PS225; SEQ ID NO: 3 to 8), all binding to a continuous stretch of at least 21 nucleotides within a specific sequence of exon 45 (i.e. SEQ ID NO:2), were tested at two different concentrations (200 and 500 nM). All six AONs were effective in inducing specific exon 45 skipping, as confirmed by sequence analysis (not shown). PS220 (SEQ ID NO:3) however, reproducibly induced highest levels of exon 45 skipping (see FIG. 2). (NT: non-treated cells, M: size marker).
Figure 2:
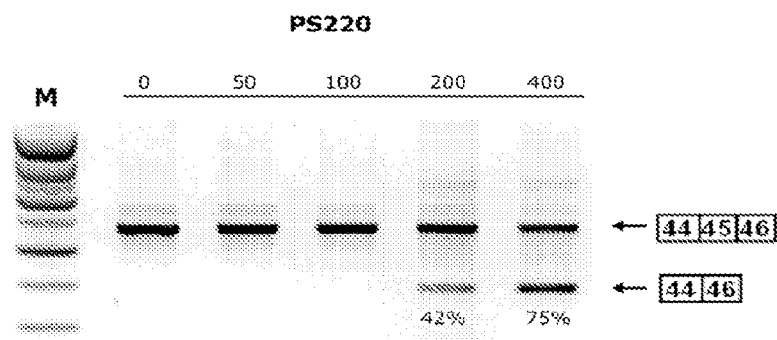
FIG. 2. In human control myotubes, 25-mer PS220 (SEQ ID NO: 3) was tested at increasing concentration. Levels of exon 45 skipping of up to 75% (at 400 nM) were observed reproducibly, as assessed by Agilent LabChip Analysis.
Figure 3:
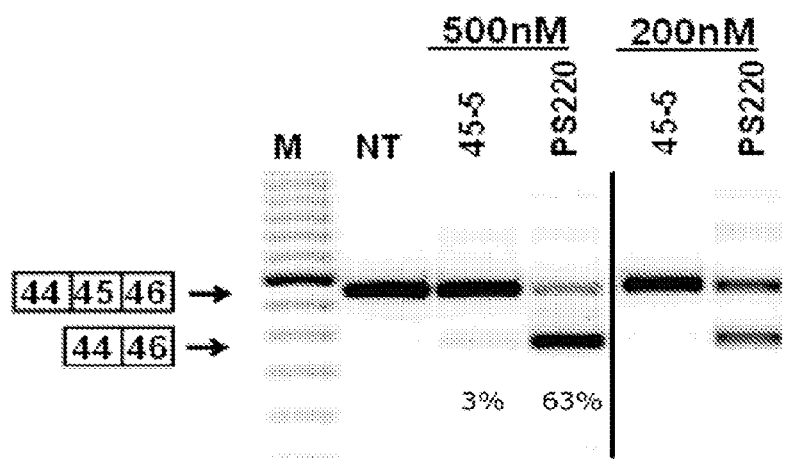
FIG. 3. In human control myotubes, the efficiencies of a "short" 17-mer AON45-5 (SEQ ID NO:68) and its overlapping "long" 25-mer counterpart PS220 were directly compared at 200 nM and 500 nM. PS220 was markedly more efficient at both concentrations: 63% when compared to 3% obtained with 45-5. (NT: non-treated cells, M: size marker).

A series of AONs targeting sequences within SEQ ID NO:2 within exon 45 were designed and tested in normal myotube cultures, by transfection and subsequent RT-PCR and sequence analysis of isolated RNA. PS220 (SEQ ID NO: 3) reproducibly induced highest levels of exon 45 skipping, when compared to PS221-PS225 (FIG. 1). High levels of exon 45 skipping of up to 75% were already obtained at 400 nM PS220 (FIG. 2). In a direct comparison, PS220 (a 25-mer) was reproducibly more efficient in inducing exon 45 skipping than its shorter 17-mer counterpart AON 45-5 (SEQ ID NO: 68; previously published as h45AON5 (Aartsma-Rus et al. Am J Hum Genet 2004; 74: 83-92)), at both AON concentrations of 200 nM and 500 nM and with 63% versus 3% respectively at 500 nM (FIG. 3). This result is probably due to the fact that the extended length of PS220, in fact completely overlapping AON 45-5, increases the free energy of the AON-target complex such that the efficiency of inducing exon 45 skipping is also increased.

TABLE 1

| AONs in exon 45 | | |
|---|---|---|
| SEQ ID NO 3 (PS220) | UUUGCCGCUGCCCAAUGCCAUCCUG | |
| SEQ ID NO 4 (PS221) | AUUCAAUGUUCUGACAACAGUUUGC | |
| SEQ ID NO 5 (PS222) | CCAGUUGCAUUCAAUGUUCUGACAA | |
| SEQ ID NO 6 (PS223) | CAGUUGCAUUCAAUGUUCUGAC | |
| SEQ ID NO 7 (PS224) | AGUUGCAUUCAAUGUUCUGA | |
| SEQ ID NO 8 (PS225) | GAUUGCUGAAUUAUUUCUUCC | |
| SEQ ID NO 9 | GAUUGCUGAAUUAUUUCUUCCCCAG | |
| SEQ ID NO 10 | AUUGCUGAAUUAUUUCUUCCCCAGU | |
| SEQ ID NO 11 | UUGCUGAAUUAUUUCUUCCCCAGUU | |
| SEQ ID NO 12 | UGCUGAAUUAUUUCUUCCCCAGUUG | |
| SEQ ID NO 13 | GCUGAAUUAUUUCUUCCCCAGUUGC | |
| SEQ ID NO 14 | CUGAAUUAUUUCUUCCCCAGUUGCA | |
| SEQ ID NO 15 | UGAAUUAUUUCUUCCCCAGUUGCAU | |
| SEQ ID NO 16 | GAAUUAUUUCUUCCCCAGUUGCAUU | |
| SEQ ID NO 17 | AAUUAUUUCUUCCCCAGUUGCAUUC | |
| SEQ ID NO 18 | AUUAUUUCUUCCCCAGUUGCAUUCA | |
| SEQ ID NO 19 | UUAUUUCUUCCCCAGUUGCAUUCAA | |
| SEQ ID NO 20 | UAUUUCUUCCCCAGUUGCAUUCAAU | |
| SEQ ID NO 21 | AUUUCUUCCCCAGUUGCAUUCAAUG | |
| SEQ ID NO 22 | UUUCUUCCCCAGUUGCAUUCAAUGU | |
| SEQ ID NO 23 | UUCUUCCCCAGUUGCAUUCAAUGUU | |
| SEQ ID NO 24 | UCUUCCCCAGUUGCAUUCAAUGUUC | |
| SEQ ID NO 25 | CUUCCCCAGUUGCAUUCAAUGUUCU | |
| SEQ ID NO 26 | UUCCCCAGUUGCAUUCAAUGUUCUG | |
| SEQ ID NO 27 | UCCCCAGUUGCAUUCAAUGUUCUGA | |
| SEQ ID NO 28 | CCCCAGUUGCAUUCAAUGUUCUGAC | |
| SEQ ID NO 29 | CCCAGUUGCAUUCAAUGUUCUGACA | |
| SEQ ID NO 30 | CCAGUUGCAUUCAAUGUUCUGACAA | |
| SEQ ID NO 31 | CAGUUGCAUUCAAUGUUCUGACAAC | |
| SEQ ID NO 32 | AGUUGCAUUCAAUGUUCUGACAACA | |
| SEQ ID NO 33 | UCC UGU AGA AUA CUG GCA UC | |
| SEQ ID NO 34 | UGC AGA CCU CCU GCC ACC GCA GAU UCA | |
| SEQ ID NO 35 | UUGCAGACCUCCUGCCACCGCAGAUUCAGGCUUC | |
| SEQ ID NO 36 | GUUGCAUUCAAUGUUCUGACAACAG | |
| SEQ ID NO 37 | UUGCAUUCAAUGUUCUGACAACAGU | |
| SEQ ID NO 38 | UGCAUUCAAUGUUCUGACAACAGUU | |
| SEQ ID NO 39 | GCAUUCAAUGUUCUGACAACAGUUU | |
| SEQ ID NO 40 | CAUUCAAUGUUCUGACAACAGUUUG | |
| SEQ ID NO 41 | AUUCAAUGUUCUGACAACAGUUUGC | |
| SEQ ID NO 42 | UCAAUGUUCUGACAACAGUUUGCCG | |
| SEQ ID NO 43 | CAAUGUUCUGACAACAGUUUGCCGC | |
| SEQ ID NO 44 | AAUGUUCUGACAACAGUUUGCCGCU | |
| SEQ ID NO 45 | AUGUUCUGACAACAGUUUGCCGCUG | |
| SEQ ID NO 46 | UGUUCUGACAACAGUUUGCCGCUGC | |
| SEQ ID NO 47 | GUUCUGACAACAGUUUGCCGCUGCC | |
| SEQ ID NO 48 | UUCUGACAACAGUUUGCCGCUGCCC | |
| SEQ ID NO 49 | UCUGACAACAGUUUGCCGCUGCCCA | |
| SEQ ID NO 50 | CUGACAACAGUUUGCCGCUGCCCAA | |
| SEQ ID NO 51 | UGACAACAGUUUGCCGCUGCCCAAU | |
| SEQ ID NO 52 | GACAACAGUUUGCCGCUGCCCAAUG | |
| SEQ ID NO 53 | ACAACAGUUUGCCGCUGCCCAAUGC | |
| SEQ ID NO 54 | CAACAGUUUGCCGCUGCCCAAUGCC | |
| SEQ ID NO 55 | AACAGUUUGCCGCUGCCCAAUGCCA | |
| SEQ ID NO 56 | ACAGUUUGCCGCUGCCCAAUGCCAU | |
| SEQ ID NO 57 | CAGUUUGCCGCUGCCCAAUGCCAUC | |
| SEQ ID NO 58 | AGUUUGCCGCUGCCCAAUGCCAUCC | |
| SEQ ID NO 59 | GUUUGCCGCUGCCCAAUGCCAUCCU | |
| SEQ ID NO 60 | UUUGCCGCUGCCCAAUGCCAUCCUG | |
| SEQ ID NO 61 | UUGCCGCUGCCCAAUGCCAUCCUGG | |
| SEQ ID NO 62 | UGCCGCUGCCCAAUGCCAUCCUGGA | |
| SEQ ID NO 63 | GCCGCUGCCCAAUGCCAUCCUGGAG | |
| SEQ ID NO 64 | CCGCUGCCCAAUGCCAUCCUGGAGU | |

TABLE 1-continued

AONs in exon 45

| | |
|---|---|
| SEQ ID NO 65 | CGCUGCCCAAUGCCAUCCUGGAGUU |
| SEQ ID NO 66 | UGU UUU UGA GGA UUG CUG AA |
| SEQ ID NO 67 | UGUUCUGACAACAGUUUGCCGCUGCCCAAUGCCAUCCUGG |
| SEQ ID NO 68 (45-5) | GCCCAAUGCCAUCCUGG |

TABLE 2

AONs in exons 51, 53, 7, 44, 46, 59, and 67

DMD Gene Exon 51

| | |
|---|---|
| SEQ ID NO 69 | AGAGCAGGUACCUCCAACAUCAAGG |
| SEQ ID NO 70 | GAGCAGGUACCUCCAACAUCAAGGA |
| SEQ ID NO 71 | AGCAGGUACCUCCAACAUCAAGGAA |
| SEQ ID NO 72 | GCAGGUACCUCCAACAUCAAGGAAG |
| SEQ ID NO 73 | CAGGUACCUCCAACAUCAAGGAAGA |
| SEQ ID NO 74 | AGGUACCUCCAACAUCAAGGAAGAU |
| SEQ ID NO 75 | GGUACCUCCAACAUCAAGGAAGAUG |
| SEQ ID NO 76 | GUACCUCCAACAUCAAGGAAGAUGG |
| SEQ ID NO 77 | UACCUCCAACAUCAAGGAAGAUGGC |
| SEQ ID NO 78 | ACCUCCAACAUCAAGGAAGAUGGCA |
| SEQ ID NO 79 | CCUCCAACAUCAAGGAAGAUGGCAU |
| SEQ ID NO 80 | CUCCAACAUCAAGGAAGAUGGCAUU |
| SEQ ID NO 81 | CUCCAACAUCAAGGAAGAUGGCAUUUCUAG |
| SEQ ID NO 82 | UCCAACAUCAAGGAAGAUGGCAUUU |
| SEQ ID NO 83 | CCAACAUCAAGGAAGAUGGCAUUUC |
| SEQ ID NO 84 | CAACAUCAAGGAAGAUGGCAUUUCU |
| SEQ ID NO 85 | AACAUCAAGGAAGAUGGCAUUUCUA |
| SEQ ID NO 86 | ACAUCAAGGAAGAUGGCAUUUCUAG |
| SEQ ID NO 87 | ACAUCAAGGAAGAUGGCAUUUCUAGUUUGG |
| SEQ ID NO 88 | ACAUCAAGGAAGAUGGCAUUUCUAG |
| SEQ ID NO 89 | CAUCAAGGAAGAUGGCAUUUCUAGU |
| SEQ ID NO 90 | AUCAAGGAAGAUGGCAUUUCUAGUU |
| SEQ ID NO 91 | UCAAGGAAGAUGGCAUUUCUAGUUU |
| SEQ ID NO 92 | UCAAGGAAGAUGGCAUUUCU |
| SEQ ID NO 93 | CAAGGAAGAUGGCAUUUCUAGUUUG |
| SEQ ID NO 94 | AAGGAAGAUGGCAUUUCUAGUUUGG |
| SEQ ID NO 95 | AGGAAGAUGGCAUUUCUAGUUUGGA |
| SEQ ID NO 96 | GGAAGAUGGCAUUUCUAGUUUGGAG |
| SEQ ID NO 97 | GAAGAUGGCAUUUCUAGUUUGGAGA |

TABLE 2-continued

AONs in exons 51, 53, 7, 44, 46, 59, and 67

| | |
|---|---|
| SEQ ID NO 98 | AAGAUGGCAUUUCUAGUUUGGAGAU |
| SEQ ID NO 99 | AGAUGGCAUUUCUAGUUUGGAGAUG |
| SEQ ID NO 100 | GAUGGCAUUUCUAGUUUGGAGAUGG |
| SEQ ID NO 101 | AUGGCAUUUCUAGUUUGGAGAUGGC |
| SEQ ID NO 102 | UGGCAUUUCUAGUUUGGAGAUGGCA |
| SEQ ID NO 103 | GGCAUUUCUAGUUUGGAGAUGGCAG |
| SEQ ID NO 104 | GCAUUUCUAGUUUGGAGAUGGCAGU |
| SEQ ID NO 105 | CAUUUCUAGUUUGGAGAUGGCAGUU |
| SEQ ID NO 106 | AUUUCUAGUUUGGAGAUGGCAGUUU |
| SEQ ID NO 107 | UUUCUAGUUUGGAGAUGGCAGUUUC |
| SEQ ID NO 108 | UUCUAGUUUGGAGAUGGCAGUUUCC |

DMD Gene Exon 53

| | |
|---|---|
| SEQ ID NO 109 | CCAUUGUGUUGAAUCCUUUAACAUU |
| SEQ ID NO 110 | CCAUUGUGUUGAAUCCUUUAAC |
| SEQ ID NO 111 | AUUGUGUUGAAUCCUUUAAC |
| SEQ ID NO 112 | CCUGUCCUAAGACCUGCUCA |
| SEQ ID NO 113 | CUUUUGGAUUGCAUCUACUGUAUAG |
| SEQ ID NO 114 | CAUUCAACUGUUGCCUCCGGUUCUG |
| SEQ ID NO 115 | CUGUUGCCUCCGGUUCUGAAGGUG |
| SEQ ID NO 116 | CAUUCAACUGUUGCCUCCGGUUCUGAAGGUG |
| SEQ ID NO 117 | CUGAAGGUGUUCUUGUACUUCAUCC |
| SEQ ID NO 118 | UGUAUAGGGACCCUCCUUCCAUGACUC |
| SEQ ID NO 119 | AUCCCACUGAUUCUGAAUUC |
| SEQ ID NO 120 | UUGGCUCUGGCCUGUCCUAAGA |
| SEQ ID NO 121 | AAGACCUGCUCAGCUUCUUCCUUAGCUUCCAGCCA |

DMD Gene Exon 7

| | |
|---|---|
| SEQ ID NO 122 | UGCAUGUUCCAGUCGUUGUGUGG |
| SEQ ID NO 123 | CACUAUUCCAGUCAAAUAGGUCUGG |
| SEQ ID NO 124 | AUUUACCAACCUUCAGGAUCGAGUA |
| SEQ ID NO 125 | GGCCUAAAACACAUACACAUA |

DMD Gene Exon 44

| | |
|---|---|
| SEQ ID NO 126 | UCAGCUUCUGUUAGCCACUG |
| SEQ ID NO 127 | UUCAGCUUCUGUUAGCCACU |
| SEQ ID NO 128 | UUCAGCUUCUGUUAGCCACUG |
| SEQ ID NO 129 | UCAGCUUCUGUUAGCCACUGA |
| SEQ ID NO 130 | UUCAGCUUCUGUUAGCCACUGA |
| SEQ ID NO 131 | UCAGCUUCUGUUAGCCACUGA |
| SEQ ID NO 132 | UUCAGCUUCUGUUAGCCACUGA |
| SEQ ID NO 133 | UCAGCUUCUGUUAGCCACUGAU |

TABLE 2-continued

AONs in exons 51, 53, 7, 44, 46, 59, and 67

| | |
|---|---|
| SEQ ID NO 134 | UUCAGCUUCUGUUAGCCACUGAU |
| SEQ ID NO 135 | UCAGCUUCUGUUAGCCACUGAUU |
| SEQ ID NO 136 | UUCAGCUUCUGUUAGCCACUGAUU |
| SEQ ID NO 137 | UCAGCUUCUGUUAGCCACUGAUUA |
| SEQ ID NO 138 | UUCAGCUUCUGUUAGCCACUGAUA |
| SEQ ID NO 139 | UCAGCUUCUGUUAGCCACUGAUUAA |
| SEQ ID NO 140 | UUCAGCUUCUGUUAGCCACUGAUUAA |
| SEQ ID NO 141 | UCAGCUUCUGUUAGCCACUGAUUAAA |
| SEQ ID NO 142 | UUCAGCUUCUGUUAGCCACUGAUUAAA |
| SEQ ID NO 143 | CAGCUUCUGUUAGCCACUG |
| SEQ ID NO 144 | CAGCUUCUGUUAGCCACUGAU |
| SEQ ID NO 145 | AGCUUCUGUUAGCCACUGAUU |
| SEQ ID NO 146 | CAGCUUCUGUUAGCCACUGAUU |
| SEQ ID NO 147 | AGCUUCUGUUAGCCACUGAUUA |
| SEQ ID NO 148 | CAGCUUCUGUUAGCCACUGAUUA |
| SEQ ID NO 149 | AGCUUCUGUUAGCCACUGAUUAA |
| SEQ ID NO 150 | CAGCUUCUGUUAGCCACUGAUUAA |
| SEQ ID NO 151 | AGCUUCUGUUAGCCACUGAUUAAA |
| SEQ ID NO 152 | CAGCUUCUGUUAGCCACUGAUUAAA |
| SEQ ID NO 153 | AGCUUCUGUUAGCCACUGAUUAAAA |
| SEQ ID NO 154 | AGCUUCUGUUAGCCACUGAU |
| SEQ ID NO 155 | GCUUCUGUUAGCCACUGAUU |
| SEQ ID NO 156 | AGCUUCUGUUAGCCACUGAUU |
| SEQ ID NO 157 | GCUUCUGUUAGCCACUGAUUA |
| SEQ ID NO 158 | AGCUUCUGUUAGCCACUGAUUA |
| SEQ ID NO 159 | GCUUCUGUUAGCCACUGAUUAA |
| SEQ ID NO 160 | AGCUUCUGUUAGCCACUGAUUAA |
| SEQ ID NO 161 | GCUUCUGUUAGCCACUGAUUAAA |
| SEQ ID NO 162 | AGCUUCUGUUAGCCACUGAUUAAA |
| SEQ ID NO 163 | GCUUCUGUUAGCCACUGAUUAAAA |
| SEQ ID NO 164 | CCAUUUGUAUUUAGCAUGUUCCC |
| SEQ ID NO 165 | AGAUACCAUUUGUAUUUAGC |
| SEQ ID NO 166 | GCCAUUUCUCAACAGAUCU |
| SEQ ID NO 167 | GCCAUUUCUCAACAGAUCUGUCA |
| SEQ ID NO 168 | AUUCUCAGGAAUUUGUGUCUUUC |
| SEQ ID NO 169 | UCUCAGGAAUUUGUGUCUUUC |
| SEQ ID NO 170 | GUUCAGCUUCUGUUAGCC |
| SEQ ID NO 171 | CUGAUUAAAUAUCUUUAUAU C |
| SEQ ID NO 172 | GCCGCCAUUUCUCAACAG |

TABLE 2-continued

AONs in exons 51, 53, 7, 44, 46, 59, and 67

| | |
|---|---|
| SEQ ID NO 173 | GUAUUUAGCAUGUUCCCA |
| SEQ ID NO 174 | CAGGAAUUUGUGUCUUUC |

DMD Gene Exon 46

| | |
|---|---|
| SEQ ID NO 175 | GCUUUUCUUUUAGUUGCUGCUCUUU |
| SEQ ID NO 176 | CUUUUCUUUUAGUUGCUGCUCUUUU |
| SEQ ID NO 177 | UUUUCUUUUAGUUGCUGCUCUUUUC |
| SEQ ID NO 178 | UUUCUUUUAGUUGCUGCUCUUUUCC |
| SEQ ID NO 179 | UUCUUUUAGUUGCUGCUCUUUUCCA |
| SEQ ID NO 180 | UCUUUUAGUUGCUGCUCUUUUCCAG |
| SEQ ID NO 181 | CUUUUAGUUGCUGCUCUUUUCCAGG |
| SEQ ID NO 182 | UUUUAGUUGCUGCUCUUUUCCAGGU |
| SEQ ID NO 183 | UUUAGUUGCUGCUCUUUUCCAGGUU |
| SEQ ID NO 184 | UUAGUUGCUGCUCUUUUCCAGGUUC |
| SEQ ID NO 185 | UAGUUGCUGCUCUUUUCCAGGUUCA |
| SEQ ID NO 186 | AGUUGCUGCUCUUUUCCAGGUUCAA |
| SEQ ID NO 187 | GUUGCUGCUCUUUUCCAGGUUCAAG |
| SEQ ID NO 188 | UUGCUGCUCUUUUCCAGGUUCAAGU |
| SEQ ID NO 189 | UGCUGCUCUUUUCCAGGUUCAAGUG |
| SEQ ID NO 190 | GCUGCUCUUUUCCAGGUUCAAGUGG |
| SEQ ID NO 191 | CUGCUCUUUUCCAGGUUCAAGUGGG |
| SEQ ID NO 192 | UGCUCUUUUCCAGGUUCAAGUGGGA |
| SEQ ID NO 193 | GCUCUUUUCCAGGUUCAAGUGGGAC |
| SEQ ID NO 194 | CUCUUUUCCAGGUUCAAGUGGGAUA |
| SEQ ID NO 195 | UCUUUUCCAGGUUCAAGUGGGAUAC |
| SEQ ID NO 196 | CUUUUCCAGGUUCAAGUGGGAUACU |
| SEQ ID NO 197 | UUUUCCAGGUUCAAGUGGGAUACUA |
| SEQ ID NO 198 | UUUCCAGGUUCAAGUGGGAUACUAG |
| SEQ ID NO 199 | UUCCAGGUUCAAGUGGGAUACUAGC |
| SEQ ID NO 200 | UCCAGGUUCAAGUGGGAUACUAGCA |
| SEQ ID NO 201 | CCAGGUUCAAGUGGGAUACUAGCAA |
| SEQ ID NO 202 | CAGGUUCAAGUGGGAUACUAGCAAU |
| SEQ ID NO 203 | AGGUUCAAGUGGGAUACUAGCAAUG |
| SEQ ID NO 204 | GGUUCAAGUGGGAUACUAGCAAUGU |
| SEQ ID NO 205 | GUUCAAGUGGGAUACUAGCAAUGUU |
| SEQ ID NO 206 | UUCAAGUGGGAUACUAGCAAUGUUA |
| SEQ ID NO 207 | UCAAGUGGGAUACUAGCAAUGUUAU |
| SEQ ID NO 208 | CAAGUGGGAUACUAGCAAUGUUAUC |
| SEQ ID NO 209 | AAGUGGGAUACUAGCAAUGUUAUCU |
| SEQ ID NO 210 | AGUGGGAUACUAGCAAUGUUAUCUG |

TABLE 2-continued

AONs in exons 51, 53, 7, 44, 46, 59, and 67

| | |
|---|---|
| SEQ ID NO 211 | GUGGGAUACUAGCAAUGUUAUCUGC |
| SEQ ID NO 212 | UGGGAUACUAGCAAUGUUAUCUGCU |
| SEQ ID NO 213 | GGGAUACUAGCAAUGUUAUCUGCUU |
| SEQ ID NO 214 | GGAUACUAGCAAUGUUAUCUGCUUC |
| SEQ ID NO 215 | GAUACUAGCAAUGUUAUCUGCUUCC |
| SEQ ID NO 216 | AUACUAGCAAUGUUAUCUGCUUCCU |
| SEQ ID NO 217 | UACUAGCAAUGUUAUCUGCUUCCUC |
| SEQ ID NO 218 | ACUAGCAAUGUUAUCUGCUUCCUCC |
| SEQ ID NO 219 | CUAGCAAUGUUAUCUGCUUCCUCCA |
| SEQ ID NO 220 | UAGCAAUGUUAUCUGCUUCCUCCAA |
| SEQ ID NO 221 | AGCAAUGUUAUCUGCUUCCUCCAAC |
| SEQ ID NO 222 | GCAAUGUUAUCUGCUUCCUCCAACC |
| SEQ ID NO 223 | CAAUGUUAUCUGCUUCCUCCAACCA |
| SEQ ID NO 224 | AAUGUUAUCUGCUUCCUCCAACCAU |

TABLE 2-continued

AONs in exons 51, 53, 7, 44, 46, 59, and 67

| | |
|---|---|
| SEQ ID NO 225 | AUGUUAUCUGCUUCCUCCAACCAUA |
| SEQ ID NO 226 | UGUUAUCUGCUUCCUCCAACCAUAA |
| SEQ ID NO 227 | GUUAUCUGCUUCCUCCAACCAUAAA |
| SEQ ID NO 228 | GCUGCUCUUUUCCAGGUUC |
| SEQ ID NO 229 | UCUUUUCCAGGUUCAAGUGG |
| SEQ ID NO 230 | AGGUUCAAGUGGGAUACUA |
| DMD Gene Exon 59 | |
| SEQ ID NO 231 | CAAUUUUUCCCACUCAGUAUU |
| SEQ ID NO 232 | UUGAAGUUCCUGGAGUCUU |
| SEQ ID NO 233 | UCCUCAGGAGGCAGCUCUAAAU |
| DMD Gene Exon 67 | |
| SEQ ID NO 234 | GCGCUGGUCACAAAAUCCUGUUGAAC |
| SEQ ID NO 235 | CACUUGCUUGAAAAGGUCUACAAAGGA |
| SEQ ID NO 236 | GGUGAAUAACUUACAAAUUUGGAAGC |

---

We claim:

1. An antisense oligonucleotide whose base sequence consists of the base sequence of 5 'UUUGCCGCUGC-CCAAUGCCAUCCUG-3' (SEQ ID: NO: 3), said oligonucleotide comprising a modification.

2. The oligonucleotide of claim 1, comprising a phosphorodiamidate morpholino oligomer (PMO).

3. The oligonucleotide of claim 1, wherein said oligonucleotide comprises a locked nucleic acid (LNA).

4. The antisense oligonucleotide of claim 1 wherein the oligonucleotide comprises a modified base.

5. The antisense oligonucleotide of claim 1 wherein the oligonucleotide comprises a modified sugar moiety.

6. The antisense oligonucleotide of claim 1 wherein the oligonucleotide comprises a modified internucleoside linkage.

7. The oligonucleotide of claim 1 wherein said oligonucleotide comprises a phosphorothioate internucleoside linkage and a 2'-O-alkyl substituted ribose moiety.

8. The oligonucleotide of claim 5, wherein the modified sugar moiety is selected from the group consisting of: a ribose that is mono- or di-substituted at the 2', 3', and/or 5' position.

9. The oligonucleotide of claim 8, wherein the ribose is a 2'-O-substituted ribose.

10. The oligonucleotide of claim 9, wherein the ribose is a 2'-O-methyl ribose.

11. The oligonucleotide of claim 6, said oligonucleotide comprising a modified backbone such that all of internucleoside linkages of said oligonucleotide are modified.

12. The oligonucleotide of claim 11, said internucleoside linkages comprising phosphorothioate.

13. The oligonucleotide of claim 11, said internucleoside linkages comprising a phosphorodiamidate morpholino oligomer (PMO).

14. The oligonucleotide of claim 1 said modification comprising a peptide nucleic acid, and/or locked nucleic acid.

15. The oligonucleotide of claim 11, wherein said backbone is selected from the group consisting of a morpholino backbone, a carbamate backbone, a siloxane backbone, a sulfide backbone, a sulfoxide backbone, a sulfone backbone, a formacetyl backbone, a thioformacetyl backbone, a methyleneformacetyl backbone, a riboacetyl backbone, an alkene containing backbone, a sulfamate backbone, a sulfonate backbone, a sulfonamide backbone, a methyleneimino backbone, a methylenehydrazino backbone and an amide backbone.

16. The antisense oligonucleotide of claim 1 wherein said oligonucleotide is capable of inducing skipping of exon 45 by at least 50%.

17. The antisense oligonucleotide of claim 16, wherein said oligonucleotide is capable of inducing skipping of exon 45 by at least 60%.

18. The antisense oligonucleotide of claim 17, wherein said oligonucleotide is capable of inducing skipping of exon 45 by at least 70%.

19. The antisense oligonucleotide of claim 18, wherein said oligonucleotide is capable of inducing skipping of exon 45 by at least 80%.

20. The antisense oligonucleotide of claim 19, wherein said oligonucleotide is capable of inducing skipping of exon 45 by at least 90%.

21. A viral-based vector comprising an expression cassette comprising a nucleotide sequence encoding the oligonucleotide of claim 1.

22. A pharmaceutical composition comprising the oligonucleotide of claim 1, and a pharmaceutically acceptable carrier.

23. The pharmaceutical composition of claim 1, further comprising an antisense oligonucleotide which induces or promotes skipping of exon 7, 44, 46, 51, 53, 59, or 67 of dystrophin pre-mRNA of a patient.

* * * * *

SEQUENCE LISTING

<160> NUMBER OF SEQ ID NOS: 236

<210> SEQ ID NO 1
<211> LENGTH: 3685
<212> TYPE: PRT
<213> ORGANISM: homo sapiens

<400> SEQUENCE: 1

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
```

```
                180               185               190
Thr Gln Arg Leu Glu His Ala Phe Asn Ile Ala Arg Tyr Gln Leu Gly
            195               200               205
Ile Glu Lys Leu Leu Asp Pro Glu Asp Val Asp Thr Thr Tyr Pro Asp
        210               215               220
Lys Lys Ser Ile Leu Met Tyr Ile Thr Ser Leu Phe Gln Val Leu Pro
225               230               235               240
Gln Gln Val Ser Ile Glu Ala Ile Gln Glu Val Glu Met Leu Pro Arg
            245               250               255
Pro Pro Lys Val Thr Lys Glu Glu His Phe Gln Leu His His Gln Met
            260               265               270
His Tyr Ser Gln Gln Ile Thr Val Ser Leu Ala Gln Gly Tyr Glu Arg
            275               280               285
Thr Ser Ser Pro Lys Pro Arg Phe Lys Ser Tyr Ala Tyr Thr Gln Ala
            290               295               300
Ala Tyr Val Thr Thr Ser Asp Pro Thr Arg Ser Pro Phe Pro Ser Gln
305               310               315               320
His Leu Glu Ala Pro Glu Asp Lys Ser Phe Gly Ser Ser Leu Met Glu
            325               330               335
Ser Glu Val Asn Leu Asp Arg Tyr Gln Thr Ala Leu Glu Glu Val Leu
            340               345               350
Ser Trp Leu Leu Ser Ala Glu Asp Thr Leu Gln Ala Gln Gly Glu Ile
            355               360               365
Ser Asn Asp Val Glu Val Val Lys Asp Gln Phe His Thr His Glu Gly
            370               375               380
Tyr Met Met Asp Leu Thr Ala His Gln Gly Arg Val Gly Asn Ile Leu
385               390               395               400
Gln Leu Gly Ser Lys Leu Ile Gly Thr Gly Lys Leu Ser Glu Asp Glu
            405               410               415
Glu Thr Glu Val Gln Glu Gln Met Asn Leu Leu Asn Ser Arg Trp Glu
            420               425               430
Cys Leu Arg Val Ala Ser Met Glu Lys Gln Ser Asn Leu His Arg Val
            435               440               445
Leu Met Asp Leu Gln Asn Gln Lys Leu Lys Glu Leu Asn Asp Trp Leu
        450               455               460
Thr Lys Thr Glu Glu Arg Thr Arg Lys Met Glu Glu Pro Leu Gly
465               470               475               480
Pro Asp Leu Glu Asp Leu Lys Arg Gln Val Gln Gln His Lys Val Leu
            485               490               495
Gln Glu Asp Leu Glu Gln Glu Gln Val Arg Val Asn Ser Leu Thr His
            500               505               510
Met Val Val Val Asp Glu Ser Ser Gly Asp His Ala Thr Ala Ala
        515               520               525
Leu Glu Glu Gln Leu Lys Val Leu Gly Asp Arg Trp Ala Asn Ile Cys
        530               535               540
Arg Trp Thr Glu Asp Arg Trp Val Leu Leu Gln Asp Ile Leu Leu Lys
545               550               555               560
Trp Gln Arg Leu Thr Glu Glu Cys Leu Phe Ser Ala Trp Leu Ser
            565               570               575
Glu Lys Glu Asp Ala Val Asn Lys Ile His Thr Thr Gly Phe Lys Asp
            580               585               590
Gln Asn Glu Met Leu Ser Ser Leu Gln Lys Leu Ala Val Leu Lys Ala
            595               600               605
```

-continued

```
Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Val Met Glu Thr Val Thr Thr Val
        675                 680                 685

Thr Thr Arg Glu Gln Ile Leu Val Lys His Ala Gln Glu Glu Leu Pro
690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
    1010                1015                1020
```

```
Glu Ile Glu Gly Arg Trp Lys Lys Leu Ser Ser Gln Leu Val Glu
    1025                1030                1035

His Cys Gln Lys Leu Glu Glu Gln Met Asn Lys Leu Arg Lys Ile
    1040                1045                1050

Gln Asn His Ile Gln Thr Leu Lys Lys Trp Met Ala Glu Val Asp
    1055                1060                1065

Val Phe Leu Lys Glu Glu Trp Pro Ala Leu Gly Asp Ser Glu Ile
    1070                1075                1080

Leu Lys Lys Gln Leu Lys Gln Cys Arg Leu Leu Val Ser Asp Ile
    1085                1090                1095

Gln Thr Ile Gln Pro Ser Leu Asn Ser Val Asn Glu Gly Gly Gln
    1100                1105                1110

Lys Ile Lys Asn Glu Ala Glu Pro Glu Phe Ala Ser Arg Leu Glu
    1115                1120                1125

Thr Glu Leu Lys Glu Leu Asn Thr Gln Trp Asp His Met Cys Gln
    1130                1135                1140

Gln Val Tyr Ala Arg Lys Glu Ala Leu Lys Gly Gly Leu Glu Lys
    1145                1150                1155

Thr Val Ser Leu Gln Lys Asp Leu Ser Glu Met His Glu Trp Met
    1160                1165                1170

Thr Gln Ala Glu Glu Glu Tyr Leu Glu Arg Asp Phe Glu Tyr Lys
    1175                1180                1185

Thr Pro Asp Glu Leu Gln Lys Ala Val Glu Glu Met Lys Arg Ala
    1190                1195                1200

Lys Glu Glu Ala Gln Gln Lys Glu Ala Lys Val Lys Leu Leu Thr
    1205                1210                1215

Glu Ser Val Asn Ser Val Ile Ala Gln Ala Pro Pro Val Ala Gln
    1220                1225                1230

Glu Ala Leu Lys Lys Glu Leu Glu Thr Leu Thr Thr Asn Tyr Gln
    1235                1240                1245

Trp Leu Cys Thr Arg Leu Asn Gly Lys Cys Lys Thr Leu Glu Glu
    1250                1255                1260

Val Trp Ala Cys Trp His Glu Leu Leu Ser Tyr Leu Glu Lys Ala
    1265                1270                1275

Asn Lys Trp Leu Asn Glu Val Glu Phe Lys Leu Lys Thr Thr Glu
    1280                1285                1290

Asn Ile Pro Gly Gly Ala Glu Glu Ile Ser Glu Val Leu Asp Ser
    1295                1300                1305

Leu Glu Asn Leu Met Arg His Ser Glu Asp Asn Pro Asn Gln Ile
    1310                1315                1320

Arg Ile Leu Ala Gln Thr Leu Thr Asp Gly Gly Val Met Asp Glu
    1325                1330                1335

Leu Ile Asn Glu Glu Leu Glu Thr Phe Asn Ser Arg Trp Arg Glu
    1340                1345                1350

Leu His Glu Glu Ala Val Arg Arg Gln Lys Leu Leu Glu Gln Ser
    1355                1360                1365

Ile Gln Ser Ala Gln Glu Thr Glu Lys Ser Leu His Leu Ile Gln
    1370                1375                1380

Glu Ser Leu Thr Phe Ile Asp Lys Gln Leu Ala Ala Tyr Ile Ala
    1385                1390                1395

Asp Lys Val Asp Ala Ala Gln Met Pro Gln Glu Ala Gln Lys Ile
    1400                1405                1410

Gln Ser Asp Leu Thr Ser His Glu Ile Ser Leu Glu Glu Met Lys
```

-continued

```
                1415                1420                1425

Lys His Asn Gln Gly Lys Glu Ala Ala Gln Arg Val Leu Ser Gln
        1430                1435                1440

Ile Asp Val Ala Gln Lys Lys Leu Gln Asp Val Ser Met Lys Phe
        1445                1450                1455

Arg Leu Phe Gln Lys Pro Ala Asn Phe Glu Gln Arg Leu Gln Glu
        1460                1465                1470

Ser Lys Met Ile Leu Asp Glu Val Lys Met His Leu Pro Ala Leu
        1475                1480                1485

Glu Thr Lys Ser Val Glu Gln Glu Val Val Gln Ser Gln Leu Asn
        1490                1495                1500

His Cys Val Asn Leu Tyr Lys Ser Leu Ser Glu Val Lys Ser Glu
        1505                1510                1515

Val Glu Met Val Ile Lys Thr Gly Arg Gln Ile Val Gln Lys Lys
        1520                1525                1530

Gln Thr Glu Asn Pro Lys Glu Leu Asp Glu Arg Val Thr Ala Leu
        1535                1540                1545

Lys Leu His Tyr Asn Glu Leu Gly Ala Lys Val Thr Glu Arg Lys
        1550                1555                1560

Gln Gln Leu Glu Lys Cys Leu Lys Leu Ser Arg Lys Met Arg Lys
        1565                1570                1575

Glu Met Asn Val Leu Thr Glu Trp Leu Ala Ala Thr Asp Met Glu
        1580                1585                1590

Leu Thr Lys Arg Ser Ala Val Glu Gly Met Pro Ser Asn Leu Asp
        1595                1600                1605

Ser Glu Val Ala Trp Gly Lys Ala Thr Gln Lys Glu Ile Glu Lys
        1610                1615                1620

Gln Lys Val His Leu Lys Ser Ile Thr Glu Val Gly Glu Ala Leu
        1625                1630                1635

Lys Thr Val Leu Gly Lys Lys Glu Thr Leu Val Glu Asp Lys Leu
        1640                1645                1650

Ser Leu Leu Asn Ser Asn Trp Ile Ala Val Thr Ser Arg Ala Glu
        1655                1660                1665

Glu Trp Leu Asn Leu Leu Leu Glu Tyr Gln Lys His Met Glu Thr
        1670                1675                1680

Phe Asp Gln Asn Val Asp His Ile Thr Lys Trp Ile Ile Gln Ala
        1685                1690                1695

Asp Thr Leu Leu Asp Glu Ser Glu Lys Lys Lys Pro Gln Gln Lys
        1700                1705                1710

Glu Asp Val Leu Lys Arg Leu Lys Ala Glu Leu Asn Asp Ile Arg
        1715                1720                1725

Pro Lys Val Asp Ser Thr Arg Asp Gln Ala Ala Asn Leu Met Ala
        1730                1735                1740

Asn Arg Gly Asp His Cys Arg Lys Leu Val Glu Pro Gln Ile Ser
        1745                1750                1755

Glu Leu Asn His Arg Phe Ala Ala Ile Ser His Arg Ile Lys Thr
        1760                1765                1770

Gly Lys Ala Ser Ile Pro Leu Lys Glu Leu Glu Gln Phe Asn Ser
        1775                1780                1785

Asp Ile Gln Lys Leu Leu Glu Pro Leu Glu Ala Glu Ile Gln Gln
        1790                1795                1800

Gly Val Asn Leu Lys Glu Glu Asp Phe Asn Lys Asp Met Asn Glu
        1805                1810                1815
```

```
Asp Asn Glu Gly Thr Val Lys Glu Leu Leu Gln Arg Gly Asp Asn
    1820            1825                1830
Leu Gln Gln Arg Ile Thr Asp Glu Arg Lys Arg Glu Ile Lys
    1835            1840                1845
Ile Lys Gln Gln Leu Leu Gln Thr Lys His Asn Ala Leu Lys Asp
    1850            1855                1860
Leu Arg Ser Gln Arg Arg Lys Lys Ala Leu Glu Ile Ser His Gln
    1865            1870                1875
Trp Tyr Gln Tyr Lys Arg Gln Ala Asp Asp Leu Leu Lys Cys Leu
    1880            1885                1890
Asp Asp Ile Glu Lys Lys Leu Ala Ser Leu Pro Glu Pro Arg Asp
    1895            1900                1905
Glu Arg Lys Ile Lys Glu Ile Asp Arg Glu Leu Gln Lys Lys Lys
    1910            1915                1920
Glu Glu Leu Asn Ala Val Arg Arg Gln Ala Glu Gly Leu Ser Glu
    1925            1930                1935
Asp Gly Ala Ala Met Ala Val Glu Pro Thr Gln Ile Gln Leu Ser
    1940            1945                1950
Lys Arg Trp Arg Glu Ile Glu Ser Lys Phe Ala Gln Phe Arg Arg
    1955            1960                1965
Leu Asn Phe Ala Gln Ile His Thr Val Arg Glu Glu Thr Met Met
    1970            1975                1980
Val Met Thr Glu Asp Met Pro Leu Glu Ile Ser Tyr Val Pro Ser
    1985            1990                1995
Thr Tyr Leu Thr Glu Ile Thr His Val Ser Gln Ala Leu Leu Glu
    2000            2005                2010
Val Glu Gln Leu Leu Asn Ala Pro Asp Leu Cys Ala Lys Asp Phe
    2015            2020                2025
Glu Asp Leu Phe Lys Gln Glu Glu Ser Leu Lys Asn Ile Lys Asp
    2030            2035                2040
Ser Leu Gln Gln Ser Ser Gly Arg Ile Asp Ile Ile His Ser Lys
    2045            2050                2055
Lys Thr Ala Ala Leu Gln Ser Ala Thr Pro Val Glu Arg Val Lys
    2060            2065                2070
Leu Gln Glu Ala Leu Ser Gln Leu Asp Phe Gln Trp Glu Lys Val
    2075            2080                2085
Asn Lys Met Tyr Lys Asp Arg Gln Gly Arg Phe Asp Arg Ser Val
    2090            2095                2100
Glu Lys Trp Arg Arg Phe His Tyr Asp Ile Lys Ile Phe Asn Gln
    2105            2110                2115
Trp Leu Thr Glu Ala Glu Gln Phe Leu Arg Lys Thr Gln Ile Pro
    2120            2125                2130
Glu Asn Trp Glu His Ala Lys Tyr Lys Trp Tyr Leu Lys Glu Leu
    2135            2140                2145
Gln Asp Gly Ile Gly Gln Arg Gln Thr Val Val Arg Thr Leu Asn
    2150            2155                2160
Ala Thr Gly Glu Glu Ile Ile Gln Gln Ser Ser Lys Thr Asp Ala
    2165            2170                2175
Ser Ile Leu Gln Glu Lys Leu Gly Ser Leu Asn Leu Arg Trp Gln
    2180            2185                2190
Glu Val Cys Lys Gln Leu Ser Asp Arg Lys Lys Arg Leu Glu Glu
    2195            2200                2205
```

-continued

```
Gln Lys Asn Ile Leu Ser Glu Phe Gln Arg Asp Leu Asn Glu Phe
2210                2215                2220

Val Leu Trp Leu Glu Glu Ala Asp Asn Ile Ala Ser Ile Pro Leu
    2225                2230                2235

Glu Pro Gly Lys Glu Gln Gln Leu Lys Glu Lys Leu Glu Gln Val
2240                2245                2250

Lys Leu Leu Val Glu Glu Leu Pro Leu Arg Gln Gly Ile Leu Lys
    2255                2260                2265

Gln Leu Asn Glu Thr Gly Gly Pro Val Leu Val Ser Ala Pro Ile
2270                2275                2280

Ser Pro Glu Glu Gln Asp Lys Leu Glu Asn Lys Leu Lys Gln Thr
    2285                2290                2295

Asn Leu Gln Trp Ile Lys Val Ser Arg Ala Leu Pro Glu Lys Gln
2300                2305                2310

Gly Glu Ile Glu Ala Gln Ile Lys Asp Leu Gly Gln Leu Glu Lys
    2315                2320                2325

Lys Leu Glu Asp Leu Glu Glu Gln Leu Asn His Leu Leu Leu Trp
2330                2335                2340

Leu Ser Pro Ile Arg Asn Gln Leu Glu Ile Tyr Asn Gln Pro Asn
    2345                2350                2355

Gln Glu Gly Pro Phe Asp Val Gln Glu Thr Glu Ile Ala Val Gln
2360                2365                2370

Ala Lys Gln Pro Asp Val Glu Glu Ile Leu Ser Lys Gly Gln His
    2375                2380                2385

Leu Tyr Lys Glu Lys Pro Ala Thr Gln Pro Val Lys Arg Lys Leu
2390                2395                2400

Glu Asp Leu Ser Ser Glu Trp Lys Ala Val Asn Arg Leu Leu Gln
    2405                2410                2415

Glu Leu Arg Ala Lys Gln Pro Asp Leu Ala Pro Gly Leu Thr Thr
2420                2425                2430

Ile Gly Ala Ser Pro Thr Gln Thr Val Thr Leu Val Thr Gln Pro
    2435                2440                2445

Val Val Thr Lys Glu Thr Ala Ile Ser Lys Leu Glu Met Pro Ser
2450                2455                2460

Ser Leu Met Leu Glu Val Pro Ala Leu Ala Asp Phe Asn Arg Ala
    2465                2470                2475

Trp Thr Glu Leu Thr Asp Trp Leu Ser Leu Leu Asp Gln Val Ile
2480                2485                2490

Lys Ser Gln Arg Val Met Val Gly Asp Leu Glu Asp Ile Asn Glu
    2495                2500                2505

Met Ile Ile Lys Gln Lys Ala Thr Met Gln Asp Leu Glu Gln Arg
2510                2515                2520

Arg Pro Gln Leu Glu Glu Leu Ile Thr Ala Ala Gln Asn Leu Lys
    2525                2530                2535

Asn Lys Thr Ser Asn Gln Glu Ala Arg Thr Ile Ile Thr Asp Arg
2540                2545                2550

Ile Glu Arg Ile Gln Asn Gln Trp Asp Glu Val Gln Glu His Leu
    2555                2560                2565

Gln Asn Arg Arg Gln Gln Leu Asn Glu Met Leu Lys Asp Ser Thr
2570                2575                2580

Gln Trp Leu Glu Ala Lys Glu Ala Glu Gln Val Leu Gly Gln
    2585                2590                2595

Ala Arg Ala Lys Leu Glu Ser Trp Lys Glu Gly Pro Tyr Thr Val
2600
```

```
                2600                2605               2610

Asp Ala Ile Gln Lys Lys Ile Thr Glu Thr Lys Gln Leu Ala Lys
        2615                2620               2625

Asp Leu Arg Gln Trp Gln Thr Asn Val Asp Val Ala Asn Asp Leu
        2630                2635               2640

Ala Leu Lys Leu Leu Arg Asp Tyr Ser Ala Asp Asp Thr Arg Lys
        2645                2650               2655

Val His Met Ile Thr Glu Asn Ile Asn Ala Ser Trp Arg Ser Ile
        2660                2665               2670

His Lys Arg Val Ser Glu Arg Glu Ala Ala Leu Glu Glu Thr His
        2675                2680               2685

Arg Leu Leu Gln Gln Phe Pro Leu Asp Leu Glu Lys Phe Leu Ala
        2690                2695               2700

Trp Leu Thr Glu Ala Glu Thr Thr Ala Asn Val Leu Gln Asp Ala
        2705                2710               2715

Thr Arg Lys Glu Arg Leu Leu Glu Asp Ser Lys Gly Val Lys Glu
        2720                2725               2730

Leu Met Lys Gln Trp Gln Asp Leu Gln Gly Glu Ile Glu Ala His
        2735                2740               2745

Thr Asp Val Tyr His Asn Leu Asp Glu Asn Ser Gln Lys Ile Leu
        2750                2755               2760

Arg Ser Leu Glu Gly Ser Asp Asp Ala Val Leu Leu Gln Arg Arg
        2765                2770               2775

Leu Asp Asn Met Asn Phe Lys Trp Ser Glu Leu Arg Lys Lys Ser
        2780                2785               2790

Leu Asn Ile Arg Ser His Leu Glu Ala Ser Ser Asp Gln Trp Lys
        2795                2800               2805

Arg Leu His Leu Ser Leu Gln Glu Leu Leu Val Trp Leu Gln Leu
        2810                2815               2820

Lys Asp Asp Glu Leu Ser Arg Gln Ala Pro Ile Gly Gly Asp Phe
        2825                2830               2835

Pro Ala Val Gln Lys Gln Asn Asp Val His Arg Ala Phe Lys Arg
        2840                2845               2850

Glu Leu Lys Thr Lys Glu Pro Val Ile Met Ser Thr Leu Glu Thr
        2855                2860               2865

Val Arg Ile Phe Leu Thr Glu Gln Pro Leu Glu Gly Leu Glu Lys
        2870                2875               2880

Leu Tyr Gln Glu Pro Arg Glu Leu Pro Pro Glu Arg Ala Gln
        2885                2890               2895

Asn Val Thr Arg Leu Leu Arg Lys Gln Ala Glu Glu Val Asn Thr
        2900                2905               2910

Glu Trp Glu Lys Leu Asn Leu His Ser Ala Asp Trp Gln Arg Lys
        2915                2920               2925

Ile Asp Glu Thr Leu Glu Arg Leu Gln Glu Leu Gln Glu Ala Thr
        2930                2935               2940

Asp Glu Leu Asp Leu Lys Leu Arg Gln Ala Glu Val Ile Lys Gly
        2945                2950               2955

Ser Trp Gln Pro Val Gly Asp Leu Leu Ile Asp Ser Leu Gln Asp
        2960                2965               2970

His Leu Glu Lys Val Lys Ala Leu Arg Gly Glu Ile Ala Pro Leu
        2975                2980               2985

Lys Glu Asn Val Ser His Val Asn Asp Leu Ala Arg Gln Leu Thr
        2990                2995               3000
```

-continued

Thr Leu Gly Ile Gln Leu Ser Pro Tyr Asn Leu Ser Thr Leu Glu
3005                3010                3015

Asp Leu Asn Thr Arg Trp Lys Leu Leu Gln Val Ala Val Glu Asp
3020                3025                3030

Arg Val Arg Gln Leu His Glu Ala His Arg Asp Phe Gly Pro Ala
3035                3040                3045

Ser Gln His Phe Leu Ser Thr Ser Val Gln Gly Pro Trp Glu Arg
3050                3055                3060

Ala Ile Ser Pro Asn Lys Val Pro Tyr Tyr Ile Asn His Glu Thr
3065                3070                3075

Gln Thr Thr Cys Trp Asp His Pro Lys Met Thr Glu Leu Tyr Gln
3080                3085                3090

Ser Leu Ala Asp Leu Asn Asn Val Arg Phe Ser Ala Tyr Arg Thr
3095                3100                3105

Ala Met Lys Leu Arg Arg Leu Gln Lys Ala Leu Cys Leu Asp Leu
3110                3115                3120

Leu Ser Leu Ser Ala Ala Cys Asp Ala Leu Asp Gln His Asn Leu
3125                3130                3135

Lys Gln Asn Asp Gln Pro Met Asp Ile Leu Gln Ile Ile Asn Cys
3140                3145                3150

Leu Thr Thr Ile Tyr Asp Arg Leu Glu Gln Glu His Asn Asn Leu
3155                3160                3165

Val Asn Val Pro Leu Cys Val Asp Met Cys Leu Asn Trp Leu Leu
3170                3175                3180

Asn Val Tyr Asp Thr Gly Arg Thr Gly Arg Ile Arg Val Leu Ser
3185                3190                3195

Phe Lys Thr Gly Ile Ile Ser Leu Cys Lys Ala His Leu Glu Asp
3200                3205                3210

Lys Tyr Arg Tyr Leu Phe Lys Gln Val Ala Ser Ser Thr Gly Phe
3215                3220                3225

Cys Asp Gln Arg Arg Leu Gly Leu Leu Leu His Asp Ser Ile Gln
3230                3235                3240

Ile Pro Arg Gln Leu Gly Glu Val Ala Ser Phe Gly Gly Ser Asn
3245                3250                3255

Ile Glu Pro Ser Val Arg Ser Cys Phe Gln Phe Ala Asn Asn Lys
3260                3265                3270

Pro Glu Ile Glu Ala Ala Leu Phe Leu Asp Trp Met Arg Leu Glu
3275                3280                3285

Pro Gln Ser Met Val Trp Leu Pro Val Leu His Arg Val Ala Ala
3290                3295                3300

Ala Glu Thr Ala Lys His Gln Ala Lys Cys Asn Ile Cys Lys Glu
3305                3310                3315

Cys Pro Ile Ile Gly Phe Arg Tyr Arg Ser Leu Lys His Phe Asn
3320                3325                3330

Tyr Asp Ile Cys Gln Ser Cys Phe Phe Ser Gly Arg Val Ala Lys
3335                3340                3345

Gly His Lys Met His Tyr Pro Met Val Glu Tyr Cys Thr Pro Thr
3350                3355                3360

Thr Ser Gly Glu Asp Val Arg Asp Phe Ala Lys Val Leu Lys Asn
3365                3370                3375

Lys Phe Arg Thr Lys Arg Tyr Phe Ala Lys His Pro Arg Met Gly
3380                3385                3390

| Tyr | Leu | Pro | Val | Gln | Thr | Val | Leu | Glu | Gly | Asp | Asn | Met | Glu | Thr |
|---|---|---|---|---|---|---|---|---|---|---|---|---|---|---|
| | | 3395 | | | | 3400 | | | | 3405 | | | | |

| Pro | Val | Thr | Leu | Ile | Asn | Phe | Trp | Pro | Val | Asp | Ser | Ala | Pro | Ala |
|---|---|---|---|---|---|---|---|---|---|---|---|---|---|---|
| 3410 | | | | | 3415 | | | | | 3420 | | | | |

| Ser | Ser | Pro | Gln | Leu | Ser | His | Asp | Asp | Thr | His | Ser | Arg | Ile | Glu |
|---|---|---|---|---|---|---|---|---|---|---|---|---|---|---|
| 3425 | | | | | 3430 | | | | | 3435 | | | | |

| His | Tyr | Ala | Ser | Arg | Leu | Ala | Glu | Met | Glu | Asn | Ser | Asn | Gly | Ser |
|---|---|---|---|---|---|---|---|---|---|---|---|---|---|---|
| 3440 | | | | | 3445 | | | | | 3450 | | | | |

| Tyr | Leu | Asn | Asp | Ser | Ile | Ser | Pro | Asn | Glu | Ser | Ile | Asp | Asp | Glu |
|---|---|---|---|---|---|---|---|---|---|---|---|---|---|---|
| | 3455 | | | | | 3460 | | | | | 3465 | | | |

| His | Leu | Leu | Ile | Gln | His | Tyr | Cys | Gln | Ser | Leu | Asn | Gln | Asp | Ser |
|---|---|---|---|---|---|---|---|---|---|---|---|---|---|---|
| | 3470 | | | | | 3475 | | | | | 3480 | | | |

| Pro | Leu | Ser | Gln | Pro | Arg | Ser | Pro | Ala | Gln | Ile | Leu | Ile | Ser | Leu |
|---|---|---|---|---|---|---|---|---|---|---|---|---|---|---|
| | 3485 | | | | | 3490 | | | | | 3495 | | | |

| Glu | Ser | Glu | Glu | Arg | Gly | Glu | Leu | Glu | Arg | Ile | Leu | Ala | Asp | Leu |
|---|---|---|---|---|---|---|---|---|---|---|---|---|---|---|
| | 3500 | | | | | 3505 | | | | | 3510 | | | |

| Glu | Glu | Glu | Asn | Arg | Asn | Leu | Gln | Ala | Glu | Tyr | Asp | Arg | Leu | Lys |
|---|---|---|---|---|---|---|---|---|---|---|---|---|---|---|
| | 3515 | | | | | 3520 | | | | | 3525 | | | |

| Gln | Gln | His | Glu | His | Lys | Gly | Leu | Ser | Pro | Leu | Pro | Ser | Pro | Pro |
|---|---|---|---|---|---|---|---|---|---|---|---|---|---|---|
| | 3530 | | | | | 3535 | | | | | 3540 | | | |

| Glu | Met | Met | Pro | Thr | Ser | Pro | Gln | Ser | Pro | Arg | Asp | Ala | Glu | Leu |
|---|---|---|---|---|---|---|---|---|---|---|---|---|---|---|
| | 3545 | | | | | 3550 | | | | | 3555 | | | |

| Ile | Ala | Glu | Ala | Lys | Leu | Leu | Arg | Gln | His | Lys | Gly | Arg | Leu | Glu |
|---|---|---|---|---|---|---|---|---|---|---|---|---|---|---|
| | 3560 | | | | | 3565 | | | | | 3570 | | | |

| Ala | Arg | Met | Gln | Ile | Leu | Glu | Asp | His | Asn | Lys | Gln | Leu | Glu | Ser |
|---|---|---|---|---|---|---|---|---|---|---|---|---|---|---|
| | 3575 | | | | | 3580 | | | | | 3585 | | | |

| Gln | Leu | His | Arg | Leu | Arg | Gln | Leu | Leu | Glu | Gln | Pro | Gln | Ala | Glu |
|---|---|---|---|---|---|---|---|---|---|---|---|---|---|---|
| | 3590 | | | | | 3595 | | | | | 3600 | | | |

| Ala | Lys | Val | Asn | Gly | Thr | Thr | Val | Ser | Ser | Pro | Ser | Thr | Ser | Leu |
|---|---|---|---|---|---|---|---|---|---|---|---|---|---|---|
| | 3605 | | | | | 3610 | | | | | 3615 | | | |

| Gln | Arg | Ser | Asp | Ser | Ser | Gln | Pro | Met | Leu | Leu | Arg | Val | Val | Gly |
|---|---|---|---|---|---|---|---|---|---|---|---|---|---|---|
| | 3620 | | | | | 3625 | | | | | 3630 | | | |

| Ser | Gln | Thr | Ser | Asp | Ser | Met | Gly | Glu | Glu | Asp | Leu | Leu | Ser | Pro |
|---|---|---|---|---|---|---|---|---|---|---|---|---|---|---|
| | 3635 | | | | | 3640 | | | | | 3645 | | | |

| Pro | Gln | Asp | Thr | Ser | Thr | Gly | Leu | Glu | Glu | Val | Met | Glu | Gln | Leu |
|---|---|---|---|---|---|---|---|---|---|---|---|---|---|---|
| | 3650 | | | | | 3655 | | | | | 3660 | | | |

| Asn | Asn | Ser | Phe | Pro | Ser | Ser | Arg | Gly | Arg | Asn | Thr | Pro | Gly | Lys |
|---|---|---|---|---|---|---|---|---|---|---|---|---|---|---|
| | 3665 | | | | | 3670 | | | | | 3675 | | | |

| Pro | Met | Arg | Glu | Asp | Thr | Met |
|---|---|---|---|---|---|---|
| | 3680 | | | | | 3685 |

<210> SEQ ID NO 2
<211> LENGTH: 75
<212> TYPE: RNA
<213> ORGANISM: Artificial Sequence
<220> FEATURE:
<223> OTHER INFORMATION: exon

<400> SEQUENCE: 2
ccaggauggc auugggcagc ggcaaacugu gucagaaca uugaaugcaa cuggggaaga    60
aauaauucag caauc                                                    75

<210> SEQ ID NO 3
<211> LENGTH: 25
<212> TYPE: RNA
<213> ORGANISM: Artificial Sequence

```
<220> FEATURE:
<223> OTHER INFORMATION: oligonucleotide

<400> SEQUENCE: 3
uuugccgcug cccaaugcca uccug                                    25

<210> SEQ ID NO 4
<211> LENGTH: 25
<212> TYPE: RNA
<213> ORGANISM: Artificial Sequence
<220> FEATURE:
<223> OTHER INFORMATION: oligonucleotide

<400> SEQUENCE: 4
auucaauguu cugacaacag uuugc                                    25

<210> SEQ ID NO 5
<211> LENGTH: 25
<212> TYPE: RNA
<213> ORGANISM: Artificial Sequence
<220> FEATURE:
<223> OTHER INFORMATION: oligonucleotide

<400> SEQUENCE: 5
ccaguugcau ucaauguucu gacaa                                    25

<210> SEQ ID NO 6
<211> LENGTH: 22
<212> TYPE: RNA
<213> ORGANISM: Artificial Sequence
<220> FEATURE:
<223> OTHER INFORMATION: oligonucleotide

<400> SEQUENCE: 6
caguugcauu caauguucug ac                                       22

<210> SEQ ID NO 7
<211> LENGTH: 20
<212> TYPE: RNA
<213> ORGANISM: Artificial Sequence
<220> FEATURE:
<223> OTHER INFORMATION: oligonucleotide

<400> SEQUENCE: 7
aguugcauuc aauguucuga                                          20

<210> SEQ ID NO 8
<211> LENGTH: 21
<212> TYPE: RNA
<213> ORGANISM: Artificial Sequence
<220> FEATURE:
<223> OTHER INFORMATION: oligonucleotide

<400> SEQUENCE: 8
gauugcugaa uuauuucuuc c                                        21

<210> SEQ ID NO 9
<211> LENGTH: 25
<212> TYPE: RNA
<213> ORGANISM: Artificial Sequence
<220> FEATURE:
<223> OTHER INFORMATION: oligonucleotide

<400> SEQUENCE: 9
gauugcugaa uuauuucuuc ccag                                     25
```

```
<210> SEQ ID NO 10
<211> LENGTH: 25
<212> TYPE: RNA
<213> ORGANISM: Artificial Sequence
<220> FEATURE:
<223> OTHER INFORMATION: oligonucleotide

<400> SEQUENCE: 10
auugcugaau uauuucuucc ccagu                                              25

<210> SEQ ID NO 11
<211> LENGTH: 25
<212> TYPE: RNA
<213> ORGANISM: Artificial Sequence
<220> FEATURE:
<223> OTHER INFORMATION: oligonucleotide

<400> SEQUENCE: 11
uugcugaauu auuucuuccc caguu                                              25

<210> SEQ ID NO 12
<211> LENGTH: 25
<212> TYPE: RNA
<213> ORGANISM: Artificial Sequence
<220> FEATURE:
<223> OTHER INFORMATION: oligonucleotide

<400> SEQUENCE: 12
ugcugaauua uuucuucccc aguug                                              25

<210> SEQ ID NO 13
<211> LENGTH: 25
<212> TYPE: RNA
<213> ORGANISM: Artificial Sequence
<220> FEATURE:
<223> OTHER INFORMATION: oligonucleotide

<400> SEQUENCE: 13
gcugaauuau uucuucccca guugc                                              25

<210> SEQ ID NO 14
<211> LENGTH: 25
<212> TYPE: RNA
<213> ORGANISM: Artificial Sequence
<220> FEATURE:
<223> OTHER INFORMATION: oligonucleotide

<400> SEQUENCE: 14
cugaauuauu ucuucccag uugca                                               25

<210> SEQ ID NO 15
<211> LENGTH: 25
<212> TYPE: RNA
<213> ORGANISM: Artificial Sequence
<220> FEATURE:
<223> OTHER INFORMATION: oligonucleotide

<400> SEQUENCE: 15
ugaauuauuu cuucccagu ugcau                                               25

<210> SEQ ID NO 16
<211> LENGTH: 25
<212> TYPE: RNA
<213> ORGANISM: Artificial Sequence
<220> FEATURE:
<223> OTHER INFORMATION: oligonucleotide
```

```
<400> SEQUENCE: 16
gaauuauuuc uuccccaguu gcauu                                           25

<210> SEQ ID NO 17
<211> LENGTH: 25
<212> TYPE: RNA
<213> ORGANISM: Artificial Sequence
<220> FEATURE:
<223> OTHER INFORMATION: oligonucleotide

<400> SEQUENCE: 17
aauuauuucu uccccaguug cauuc                                           25

<210> SEQ ID NO 18
<211> LENGTH: 25
<212> TYPE: RNA
<213> ORGANISM: Artificial Sequence
<220> FEATURE:
<223> OTHER INFORMATION: oligonucleotide

<400> SEQUENCE: 18
auuauuucuu ccccaguugc auuca                                           25

<210> SEQ ID NO 19
<211> LENGTH: 25
<212> TYPE: RNA
<213> ORGANISM: Artificial Sequence
<220> FEATURE:
<223> OTHER INFORMATION: oligonucleotide

<400> SEQUENCE: 19
uuauuucuuc cccaguugca uucaa                                           25

<210> SEQ ID NO 20
<211> LENGTH: 25
<212> TYPE: RNA
<213> ORGANISM: Artificial Sequence
<220> FEATURE:
<223> OTHER INFORMATION: oligonucleotide

<400> SEQUENCE: 20
uauuucuucc ccaguugcau ucaau                                           25

<210> SEQ ID NO 21
<211> LENGTH: 25
<212> TYPE: RNA
<213> ORGANISM: Artificial Sequence
<220> FEATURE:
<223> OTHER INFORMATION: oligonucleotide

<400> SEQUENCE: 21
auuucuuccc caguugcauu caaug                                           25

<210> SEQ ID NO 22
<211> LENGTH: 25
<212> TYPE: RNA
<213> ORGANISM: Artificial Sequence
<220> FEATURE:
<223> OTHER INFORMATION: oligonucleotide

<400> SEQUENCE: 22
uuucuucccc aguugcauuc aaugu                                           25

<210> SEQ ID NO 23
```

```
<211> LENGTH: 25
<212> TYPE: RNA
<213> ORGANISM: Artificial Sequence
<220> FEATURE:
<223> OTHER INFORMATION: oligonucleotide

<400> SEQUENCE: 23
uucuucccca guugcauuca auguu                                      25

<210> SEQ ID NO 24
<211> LENGTH: 25
<212> TYPE: RNA
<213> ORGANISM: Artificial Sequence
<220> FEATURE:
<223> OTHER INFORMATION: oligonucleotide

<400> SEQUENCE: 24 ucuucccag uugcauucaa uguuc                                       25

<210> SEQ ID NO 25
<211> LENGTH: 25
<212> TYPE: RNA
<213> ORGANISM: Artificial Sequence
<220> FEATURE:
<223> OTHER INFORMATION: oligonucleotide

<400> SEQUENCE: 25 cuucccagu ugcauucaau guucu                                       25

<210> SEQ ID NO 26
<211> LENGTH: 25
<212> TYPE: RNA
<213> ORGANISM: Artificial Sequence
<220> FEATURE:
<223> OTHER INFORMATION: oligonucleotide

<400> SEQUENCE: 26 uucccaguu gcauucaaug uucug                                       25

<210> SEQ ID NO 27
<211> LENGTH: 25
<212> TYPE: RNA
<213> ORGANISM: Artificial Sequence
<220> FEATURE:
<223> OTHER INFORMATION: oligonucleotide

<400> SEQUENCE: 27 ucccaguug cauucaaugu ucuga                                       25

<210> SEQ ID NO 28
<211> LENGTH: 25
<212> TYPE: RNA
<213> ORGANISM: Artificial Sequence
<220> FEATURE:
<223> OTHER INFORMATION: oligonucleotide

<400> SEQUENCE: 28
ccccaguugc auucaauguu cugac                                      25

<210> SEQ ID NO 29
<211> LENGTH: 25
<212> TYPE: RNA
<213> ORGANISM: Artificial Sequence
<220> FEATURE:
<223> OTHER INFORMATION: oligonucleotide

<400> SEQUENCE: 29
```
cccaguugca uucaauguuc ugaca                                    25

<210> SEQ ID NO 30
<211> LENGTH: 25
<212> TYPE: RNA
<213> ORGANISM: Artificial Sequence
<220> FEATURE:
<223> OTHER INFORMATION: oligonucleotide

<400> SEQUENCE: 30
ccaguugcau ucaauguucu gacaa                                    25

<210> SEQ ID NO 31
<211> LENGTH: 25
<212> TYPE: RNA
<213> ORGANISM: Artificial Sequence
<220> FEATURE:
<223> OTHER INFORMATION: oligonucleotide

<400> SEQUENCE: 31
caguugcauu caauguucug acaac                                    25

<210> SEQ ID NO 32
<211> LENGTH: 25
<212> TYPE: RNA
<213> ORGANISM: Artificial Sequence
<220> FEATURE:
<223> OTHER INFORMATION: oligonucleotide

<400> SEQUENCE: 32
aguugcauuc aauguucuga caaca                                    25

<210> SEQ ID NO 33
<211> LENGTH: 20
<212> TYPE: RNA
<213> ORGANISM: Artificial Sequence
<220> FEATURE:
<223> OTHER INFORMATION: oligonucleotide

<400> SEQUENCE: 33
uccuguagaa uacuggcauc                                          20

<210> SEQ ID NO 34
<211> LENGTH: 27
<212> TYPE: RNA
<213> ORGANISM: Artificial Sequence
<220> FEATURE:
<223> OTHER INFORMATION: oligonucleotide

<400> SEQUENCE: 34
ugcagaccuc cugccaccgc agauuca                                  27

<210> SEQ ID NO 35
<211> LENGTH: 34
<212> TYPE: RNA
<213> ORGANISM: Artificial Sequence
<220> FEATURE:
<223> OTHER INFORMATION: oligonucleotide

<400> SEQUENCE: 35
uugcagaccu ccugccaccg cagauucagg cuuc                          34

<210> SEQ ID NO 36
<211> LENGTH: 25
<212> TYPE: RNA

```
<213> ORGANISM: Artificial Sequence
<220> FEATURE:
<223> OTHER INFORMATION: oligonucleotide

<400> SEQUENCE: 36
guugcauuca auguucugac aacag                                       25

<210> SEQ ID NO 37
<211> LENGTH: 25
<212> TYPE: RNA
<213> ORGANISM: Artificial Sequence
<220> FEATURE:
<223> OTHER INFORMATION: oligonucleotide

<400> SEQUENCE: 37
uugcauucaa uguucugaca acagu                                       25

<210> SEQ ID NO 38
<211> LENGTH: 25
<212> TYPE: RNA
<213> ORGANISM: Artificial Sequence
<220> FEATURE:
<223> OTHER INFORMATION: oligonucleotide

<400> SEQUENCE: 38
ugcauucaau guucugacaa caguu                                       25

<210> SEQ ID NO 39
<211> LENGTH: 25
<212> TYPE: RNA
<213> ORGANISM: Artificial Sequence
<220> FEATURE:
<223> OTHER INFORMATION: oligonucleotide

<400> SEQUENCE: 39
gcauucaaug uucugacaac aguuu                                       25

<210> SEQ ID NO 40
<211> LENGTH: 25
<212> TYPE: RNA
<213> ORGANISM: Artificial Sequence
<220> FEATURE:
<223> OTHER INFORMATION: oligonucleotide

<400> SEQUENCE: 40
cauucaaugu ucugacaaca guuug                                       25

<210> SEQ ID NO 41
<211> LENGTH: 25
<212> TYPE: RNA
<213> ORGANISM: Artificial Sequence
<220> FEATURE:
<223> OTHER INFORMATION: oligonucleotide

<400> SEQUENCE: 41
auucaauguu cugacaacag uuugc                                       25

<210> SEQ ID NO 42
<211> LENGTH: 25
<212> TYPE: RNA
<213> ORGANISM: Artificial Sequence
<220> FEATURE:
<223> OTHER INFORMATION: oligonucleotide

<400> SEQUENCE: 42
ucaauguucu gacaacaguu ugccg                                       25
```

<210> SEQ ID NO 43
<211> LENGTH: 25
<212> TYPE: RNA
<213> ORGANISM: Artificial Sequence
<220> FEATURE:
<223> OTHER INFORMATION: oligonucleotide

<400> SEQUENCE: 43
caauguucug acaacaguuu gccgc                                         25

<210> SEQ ID NO 44
<211> LENGTH: 25
<212> TYPE: RNA
<213> ORGANISM: Artificial Sequence
<220> FEATURE:
<223> OTHER INFORMATION: oligonucleotide

<400> SEQUENCE: 44
aauguucuga caacaguuug ccgcu                                         25

<210> SEQ ID NO 45
<211> LENGTH: 25
<212> TYPE: RNA
<213> ORGANISM: Artificial Sequence
<220> FEATURE:
<223> OTHER INFORMATION: oligonucleotide

<400> SEQUENCE: 45
auguucugac aacaguuugc cgcug                                         25

<210> SEQ ID NO 46
<211> LENGTH: 25
<212> TYPE: RNA
<213> ORGANISM: Artificial Sequence
<220> FEATURE:
<223> OTHER INFORMATION: oligonucleotide

<400> SEQUENCE: 46
uguucugaca acaguuugcc gcugc                                         25

<210> SEQ ID NO 47
<211> LENGTH: 25
<212> TYPE: RNA
<213> ORGANISM: Artificial Sequence
<220> FEATURE:
<223> OTHER INFORMATION: oligonucleotide

<400> SEQUENCE: 47
guucugacaa caguuugccg cugcc                                         25

<210> SEQ ID NO 48
<211> LENGTH: 25
<212> TYPE: RNA
<213> ORGANISM: Artificial Sequence
<220> FEATURE:
<223> OTHER INFORMATION: oligonucleotide

<400> SEQUENCE: 48
uucugacaac aguuugccgc ugccc                                         25

<210> SEQ ID NO 49
<211> LENGTH: 25
<212> TYPE: RNA
<213> ORGANISM: Artificial Sequence
<220> FEATURE:

<223> OTHER INFORMATION: oligonucleotide

<400> SEQUENCE: 49
ucugacaaca guuugccgcu gccca                                          25

<210> SEQ ID NO 50
<211> LENGTH: 25
<212> TYPE: RNA
<213> ORGANISM: Artificial Sequence
<220> FEATURE:
<223> OTHER INFORMATION: oligonucleotide

<400> SEQUENCE: 50
cugacaacag uuugccgcug cccaa                                          25

<210> SEQ ID NO 51
<211> LENGTH: 25
<212> TYPE: RNA
<213> ORGANISM: Artificial Sequence
<220> FEATURE:
<223> OTHER INFORMATION: oligonucleotide

<400> SEQUENCE: 51
ugacaacagu uugccgcugc ccaau                                          25

<210> SEQ ID NO 52
<211> LENGTH: 25
<212> TYPE: RNA
<213> ORGANISM: Artificial Sequence
<220> FEATURE:
<223> OTHER INFORMATION: oligonucleotide

<400> SEQUENCE: 52
gacaacaguu ugccgcugcc caaug                                          25

<210> SEQ ID NO 53
<211> LENGTH: 25
<212> TYPE: RNA
<213> ORGANISM: Artificial Sequence
<220> FEATURE:
<223> OTHER INFORMATION: oligonucleotide

<400> SEQUENCE: 53
acaacaguuu gccgcugccc aaugc                                          25

<210> SEQ ID NO 54
<211> LENGTH: 25
<212> TYPE: RNA
<213> ORGANISM: Artificial Sequence
<220> FEATURE:
<223> OTHER INFORMATION: oligonucleotide

<400> SEQUENCE: 54
caacaguuug ccgcugccca augcc                                          25

<210> SEQ ID NO 55
<211> LENGTH: 25
<212> TYPE: RNA
<213> ORGANISM: Artificial Sequence
<220> FEATURE:
<223> OTHER INFORMATION: oligonucleotide

<400> SEQUENCE: 55
aacaguuugc cgcugcccaa ugcca                                          25

```
<210> SEQ ID NO 56
<211> LENGTH: 25
<212> TYPE: RNA
<213> ORGANISM: Artificial Sequence
<220> FEATURE:
<223> OTHER INFORMATION: oligonucleotide

<400> SEQUENCE: 56
acaguuugcc gcugcccaau gccau                                        25

<210> SEQ ID NO 57
<211> LENGTH: 25
<212> TYPE: RNA
<213> ORGANISM: Artificial Sequence
<220> FEATURE:
<223> OTHER INFORMATION: oligonucleotide

<400> SEQUENCE: 57
caguuugccg cugcccaaug ccauc                                        25

<210> SEQ ID NO 58
<211> LENGTH: 25
<212> TYPE: RNA
<213> ORGANISM: Artificial Sequence
<220> FEATURE:
<223> OTHER INFORMATION: oligonucleotide

<400> SEQUENCE: 58
aguuugccgc ugcccaaugc caucc                                        25

<210> SEQ ID NO 59
<211> LENGTH: 25
<212> TYPE: RNA
<213> ORGANISM: Artificial Sequence
<220> FEATURE:
<223> OTHER INFORMATION: oligonucleotide

<400> SEQUENCE: 59
guuugccgcu gcccaaugcc auccu                                        25

<210> SEQ ID NO 60
<211> LENGTH: 25
<212> TYPE: RNA
<213> ORGANISM: Artificial Sequence
<220> FEATURE:
<223> OTHER INFORMATION: oligonucleotide

<400> SEQUENCE: 60
uuugccgcug cccaaugcca uccug                                        25

<210> SEQ ID NO 61
<211> LENGTH: 25
<212> TYPE: RNA
<213> ORGANISM: Artificial Sequence
<220> FEATURE:
<223> OTHER INFORMATION: oligonucleotide

<400> SEQUENCE: 61
uugccgcugc ccaaugccau ccugg                                        25

<210> SEQ ID NO 62
<211> LENGTH: 25
<212> TYPE: RNA
<213> ORGANISM: Artificial Sequence
<220> FEATURE:
<223> OTHER INFORMATION: oligonucleotide
```

```
<400> SEQUENCE: 62
ugccgcugcc caaugccauc cugga                                      25

<210> SEQ ID NO 63
<211> LENGTH: 25
<212> TYPE: RNA
<213> ORGANISM: Artificial Sequence
<220> FEATURE:
<223> OTHER INFORMATION: oligonucleotide

<400> SEQUENCE: 63
gccgcugccc aaugccaucc uggag                                      25

<210> SEQ ID NO 64
<211> LENGTH: 25
<212> TYPE: RNA
<213> ORGANISM: Artificial Sequence
<220> FEATURE:
<223> OTHER INFORMATION: oligonucleotide

<400> SEQUENCE: 64
ccgcugccca augccauccu ggagu                                      25

<210> SEQ ID NO 65
<211> LENGTH: 25
<212> TYPE: RNA
<213> ORGANISM: Artificial Sequence
<220> FEATURE:
<223> OTHER INFORMATION: oligonucleotide

<400> SEQUENCE: 65
cgcugcccaa ugccauccug gaguu                                      25

<210> SEQ ID NO 66
<211> LENGTH: 20
<212> TYPE: RNA
<213> ORGANISM: Artificial Sequence
<220> FEATURE:
<223> OTHER INFORMATION: oligoncleotide

<400> SEQUENCE: 66
uguuuuugag gauugcugaa                                            20

<210> SEQ ID NO 67
<211> LENGTH: 40
<212> TYPE: RNA
<213> ORGANISM: Artificial Sequence
<220> FEATURE:
<223> OTHER INFORMATION: oligonucleotide

<400> SEQUENCE: 67
uguucugaca acaguuugcc gcugcccaau gccauccugg                      40

<210> SEQ ID NO 68
<211> LENGTH: 17
<212> TYPE: RNA
<213> ORGANISM: Artificial Sequence
<220> FEATURE:
<223> OTHER INFORMATION: oligonucleotide

<400> SEQUENCE: 68
gcccaaugcc auccugg                                               17

<210> SEQ ID NO 69
<211> LENGTH: 25
```

<212> TYPE: RNA
<213> ORGANISM: Artificial Sequence
<220> FEATURE:
<223> OTHER INFORMATION: oligonucleotide

<400> SEQUENCE: 69
agagcaggua ccuccaacau caagg                                              25

<210> SEQ ID NO 70
<211> LENGTH: 25
<212> TYPE: RNA
<213> ORGANISM: Artificial Sequence
<220> FEATURE:
<223> OTHER INFORMATION: oligonucleotide

<400> SEQUENCE: 70
gagcagguac cuccaacauc aagga                                              25

<210> SEQ ID NO 71
<211> LENGTH: 25
<212> TYPE: RNA
<213> ORGANISM: Artificial Sequence
<220> FEATURE:
<223> OTHER INFORMATION: oligonucleotide

<400> SEQUENCE: 71
agcagguacc uccaacauca aggaa                                              25

<210> SEQ ID NO 72
<211> LENGTH: 25
<212> TYPE: RNA
<213> ORGANISM: Artificial Sequence
<220> FEATURE:
<223> OTHER INFORMATION: oligonucleotide

<400> SEQUENCE: 72
gcagguaccu ccaacaucaa ggaag                                              25

<210> SEQ ID NO 73
<211> LENGTH: 25
<212> TYPE: RNA
<213> ORGANISM: Artificial Sequence
<220> FEATURE:
<223> OTHER INFORMATION: oligonucleotide

<400> SEQUENCE: 73
cagguaccuc caacaucaag gaaga                                              25

<210> SEQ ID NO 74
<211> LENGTH: 25
<212> TYPE: RNA
<213> ORGANISM: Artificial Sequence
<220> FEATURE:
<223> OTHER INFORMATION: oligonucleotide

<400> SEQUENCE: 74
agguaccucc aacaucaagg aagau                                              25

<210> SEQ ID NO 75
<211> LENGTH: 25
<212> TYPE: RNA
<213> ORGANISM: Artificial Sequence
<220> FEATURE:
<223> OTHER INFORMATION: oligonucleotide

<400> SEQUENCE: 75
gguaccucca acaucaagga agaug                                   25

<210> SEQ ID NO 76
<211> LENGTH: 25
<212> TYPE: RNA
<213> ORGANISM: Artificial Sequence
<220> FEATURE:
<223> OTHER INFORMATION: oligonucleotide

<400> SEQUENCE: 76
guaccuccaa caucaaggaa gaugg                                   25

<210> SEQ ID NO 77
<211> LENGTH: 25
<212> TYPE: RNA
<213> ORGANISM: Artificial Sequence
<220> FEATURE:
<223> OTHER INFORMATION: oligonucleotide

<400> SEQUENCE: 77
uaccuccaac aucaaggaag auggc                                   25

<210> SEQ ID NO 78
<211> LENGTH: 25
<212> TYPE: RNA
<213> ORGANISM: Artificial Sequence
<220> FEATURE:
<223> OTHER INFORMATION: oligonucleotide

<400> SEQUENCE: 78
accuccaaca ucaaggaaga uggca                                   25

<210> SEQ ID NO 79
<211> LENGTH: 25
<212> TYPE: RNA
<213> ORGANISM: Artificial Sequence
<220> FEATURE:
<223> OTHER INFORMATION: oligonucleotide

<400> SEQUENCE: 79
ccuccaacau caaggaagau ggcau                                   25

<210> SEQ ID NO 80
<211> LENGTH: 25
<212> TYPE: RNA
<213> ORGANISM: Artificial Sequence
<220> FEATURE:
<223> OTHER INFORMATION: oligonucleotide

<400> SEQUENCE: 80
cuccaacauc aaggaagaug gcauu                                   25

<210> SEQ ID NO 81
<211> LENGTH: 30
<212> TYPE: RNA
<213> ORGANISM: Artificial Sequence
<220> FEATURE:
<223> OTHER INFORMATION: oligonucleotide

<400> SEQUENCE: 81
cuccaacauc aaggaagaug gcauuucuag                              30

<210> SEQ ID NO 82
<211> LENGTH: 25
<212> TYPE: RNA
<213> ORGANISM: Artificial Sequence

```
<220> FEATURE:
<223> OTHER INFORMATION: oligonucleotide

<400> SEQUENCE: 82
uccaacauca aggaagaugg cauuu                                      25

<210> SEQ ID NO 83
<211> LENGTH: 25
<212> TYPE: RNA
<213> ORGANISM: Artificial Sequence
<220> FEATURE:
<223> OTHER INFORMATION: oligonucleotide

<400> SEQUENCE: 83
ccaacaucaa ggaagauggc auuuc                                      25

<210> SEQ ID NO 84
<211> LENGTH: 25
<212> TYPE: RNA
<213> ORGANISM: Artificial Sequence
<220> FEATURE:
<223> OTHER INFORMATION: oligonucleotide

<400> SEQUENCE: 84
caacaucaag gaagauggca uuucu                                      25

<210> SEQ ID NO 85
<211> LENGTH: 25
<212> TYPE: RNA
<213> ORGANISM: Artificial Sequence
<220> FEATURE:
<223> OTHER INFORMATION: oligonucleotide

<400> SEQUENCE: 85
aacaucaagg aagauggcau uucua                                      25

<210> SEQ ID NO 86
<211> LENGTH: 25
<212> TYPE: RNA
<213> ORGANISM: Artificial Sequence
<220> FEATURE:
<223> OTHER INFORMATION: oligonucleotide

<400> SEQUENCE: 86
acaucaagga agauggcauu ucuag                                      25

<210> SEQ ID NO 87
<211> LENGTH: 30
<212> TYPE: RNA
<213> ORGANISM: Artificial Sequence
<220> FEATURE:
<223> OTHER INFORMATION: oligonucleotide

<400> SEQUENCE: 87
acaucaagga agauggcauu ucuaguuugg                                 30

<210> SEQ ID NO 88
<211> LENGTH: 25
<212> TYPE: RNA
<213> ORGANISM: Artificial Sequence
<220> FEATURE:
<223> OTHER INFORMATION: oligonucleotide

<400> SEQUENCE: 88
acaucaagga agauggcauu ucuag                                      25
```

```
<210> SEQ ID NO 89
<211> LENGTH: 25
<212> TYPE: RNA
<213> ORGANISM: Artificial Sequence
<220> FEATURE:
<223> OTHER INFORMATION: oligonucleotide

<400> SEQUENCE: 89
caucaaggaa gauggcauuu cuagu                                              25

<210> SEQ ID NO 90
<211> LENGTH: 25
<212> TYPE: RNA
<213> ORGANISM: Artificial Sequence
<220> FEATURE:
<223> OTHER INFORMATION: oligonucleotide

<400> SEQUENCE: 90
aucaaggaag auggcauuuc uaguu                                              25

<210> SEQ ID NO 91
<211> LENGTH: 25
<212> TYPE: RNA
<213> ORGANISM: Artificial Sequence
<220> FEATURE:
<223> OTHER INFORMATION: oligonucleotide

<400> SEQUENCE: 91
ucaaggaaga uggcauuucu aguuu                                              25

<210> SEQ ID NO 92
<211> LENGTH: 20
<212> TYPE: RNA
<213> ORGANISM: Artificial Sequence
<220> FEATURE:
<223> OTHER INFORMATION: oligonucleotide

<400> SEQUENCE: 92
ucaaggaaga uggcauuucu                                                    20

<210> SEQ ID NO 93
<211> LENGTH: 25
<212> TYPE: RNA
<213> ORGANISM: Artificial Sequence
<220> FEATURE:
<223> OTHER INFORMATION: oligonucleotide

<400> SEQUENCE: 93
caaggaagau ggcauuucua guuug                                              25

<210> SEQ ID NO 94
<211> LENGTH: 25
<212> TYPE: RNA
<213> ORGANISM: Artificial Sequence
<220> FEATURE:
<223> OTHER INFORMATION: oligonucleotide

<400> SEQUENCE: 94
aaggaagaug gcauuucuag uuugg                                              25

<210> SEQ ID NO 95
<211> LENGTH: 25
<212> TYPE: RNA
<213> ORGANISM: Artificial Sequence
<220> FEATURE:
<223> OTHER INFORMATION: oligonucleotide
```

```
<400> SEQUENCE: 95
aggaagaugg cauuucuagu uugga                                                25

<210> SEQ ID NO 96
<211> LENGTH: 25
<212> TYPE: RNA
<213> ORGANISM: Artificial Sequence
<220> FEATURE:
<223> OTHER INFORMATION: oligonucleotide

<400> SEQUENCE: 96
ggaagauggc auuucuaguu uggag                                                25

<210> SEQ ID NO 97
<211> LENGTH: 25
<212> TYPE: RNA
<213> ORGANISM: Artificial Sequence
<220> FEATURE:
<223> OTHER INFORMATION: oligonucleotide

<400> SEQUENCE: 97
gaagauggca uuucuaguuu ggaga                                                25

<210> SEQ ID NO 98
<211> LENGTH: 25
<212> TYPE: RNA
<213> ORGANISM: Artificial Sequence
<220> FEATURE:
<223> OTHER INFORMATION: oligonucleotide

<400> SEQUENCE: 98
aagauggcau uucuaguuug gagau                                                25

<210> SEQ ID NO 99
<211> LENGTH: 25
<212> TYPE: RNA
<213> ORGANISM: Artificial Sequence
<220> FEATURE:
<223> OTHER INFORMATION: oligonucleotide

<400> SEQUENCE: 99
agauggcauu ucuaguuugg agaug                                                25

<210> SEQ ID NO 100
<211> LENGTH: 25
<212> TYPE: RNA
<213> ORGANISM: Artificial Sequence
<220> FEATURE:
<223> OTHER INFORMATION: oligonucleotide

<400> SEQUENCE: 100
gauggcauuu cuaguuugga gaugg                                                25

<210> SEQ ID NO 101
<211> LENGTH: 25
<212> TYPE: RNA
<213> ORGANISM: Artificial Sequence
<220> FEATURE:
<223> OTHER INFORMATION: oligonucleotide

<400> SEQUENCE: 101
auggcauuuc uaguuuggag auggc                                                25

<210> SEQ ID NO 102
```

```
<211> LENGTH: 25
<212> TYPE: RNA
<213> ORGANISM: Artificial Sequence
<220> FEATURE:
<223> OTHER INFORMATION: oligonucleotide

<400> SEQUENCE: 102
uggcauuucu aguuggaga uggca                                   25

<210> SEQ ID NO 103
<211> LENGTH: 25
<212> TYPE: RNA
<213> ORGANISM: Artificial Sequence
<220> FEATURE:
<223> OTHER INFORMATION: oligonucleotide

<400> SEQUENCE: 103
ggcauuucua guuggagau ggcag                                   25

<210> SEQ ID NO 104
<211> LENGTH: 25
<212> TYPE: RNA
<213> ORGANISM: Artificial Sequence
<220> FEATURE:
<223> OTHER INFORMATION: oligonucleotide

<400> SEQUENCE: 104
gcauuucuag uuggagaug gcagu                                   25

<210> SEQ ID NO 105
<211> LENGTH: 25
<212> TYPE: RNA
<213> ORGANISM: Artificial Sequence
<220> FEATURE:
<223> OTHER INFORMATION: oligonucleotide

<400> SEQUENCE: 105
cauuucuagu uggagaugg caguu                                   25

<210> SEQ ID NO 106
<211> LENGTH: 25
<212> TYPE: RNA
<213> ORGANISM: Artificial Sequence
<220> FEATURE:
<223> OTHER INFORMATION: oligonucleotide

<400> SEQUENCE: 106
auuucuaguu ggagauggc aguuu                                   25

<210> SEQ ID NO 107
<211> LENGTH: 25
<212> TYPE: RNA
<213> ORGANISM: Artificial Sequence
<220> FEATURE:
<223> OTHER INFORMATION: oligonucleotide

<400> SEQUENCE: 107
uuucuaguuu ggagauggca guuuc                                  25

<210> SEQ ID NO 108
<211> LENGTH: 25
<212> TYPE: RNA
<213> ORGANISM: Artificial Sequence
<220> FEATURE:
<223> OTHER INFORMATION: oligonucleotide

<400> SEQUENCE: 108
```
uucuaguuug gagauggcag uuucc                                         25

<210> SEQ ID NO 109
<211> LENGTH: 25
<212> TYPE: RNA
<213> ORGANISM: Artificial Sequence
<220> FEATURE:
<223> OTHER INFORMATION: oligonucleotide

<400> SEQUENCE: 109
ccauuguguu gaauccuuua acauu                                         25

<210> SEQ ID NO 110
<211> LENGTH: 22
<212> TYPE: RNA
<213> ORGANISM: Artificial Sequence
<220> FEATURE:
<223> OTHER INFORMATION: oligonucleotide

<400> SEQUENCE: 110
ccauuguguu gaauccuuua ac                                            22

<210> SEQ ID NO 111
<211> LENGTH: 20
<212> TYPE: RNA
<213> ORGANISM: Artificial Sequence
<220> FEATURE:
<223> OTHER INFORMATION: oligonucleotide

<400> SEQUENCE: 111
auuguguuga auccuuuaac                                               20

<210> SEQ ID NO 112
<211> LENGTH: 20
<212> TYPE: RNA
<213> ORGANISM: Artificial Sequence
<220> FEATURE:
<223> OTHER INFORMATION: oligonucleotide

<400> SEQUENCE: 112
ccugyccuaa gaccugcuca                                               20

<210> SEQ ID NO 113
<211> LENGTH: 25
<212> TYPE: RNA
<213> ORGANISM: Artificial Sequence
<220> FEATURE:
<223> OTHER INFORMATION: oligonucleotide

<400> SEQUENCE: 113
cuuuuggauu gcaucuacug uauag                                         25

<210> SEQ ID NO 114
<211> LENGTH: 25
<212> TYPE: RNA
<213> ORGANISM: Artificial Sequence
<220> FEATURE:
<223> OTHER INFORMATION: oligonucleotide

<400> SEQUENCE: 114
cauucaacug uugccuccgg uucug                                         25

<210> SEQ ID NO 115
<211> LENGTH: 24
<212> TYPE: RNA

```
<213> ORGANISM: Artificial Sequence
<220> FEATURE:
<223> OTHER INFORMATION: oligonucleotide

<400> SEQUENCE: 115 cguugccuc cgguucugaa ggug                                              24

<210> SEQ ID NO 116
<211> LENGTH: 31
<212> TYPE: RNA
<213> ORGANISM: Artificial Sequence
<220> FEATURE:
<223> OTHER INFORMATION: oligonucleotide

<400> SEQUENCE: 116
cauucaacug uugccuccgg uucugaaggu g                                     31

<210> SEQ ID NO 117
<211> LENGTH: 25
<212> TYPE: RNA
<213> ORGANISM: Artificial Sequence
<220> FEATURE:
<223> OTHER INFORMATION: oligonucleotide

<400> SEQUENCE: 117
cugaaggugu ucuuguacuu caucc                                            25

<210> SEQ ID NO 118
<211> LENGTH: 27
<212> TYPE: RNA
<213> ORGANISM: Artificial Sequence
<220> FEATURE:
<223> OTHER INFORMATION: oligonucleotide

<400> SEQUENCE: 118
uguauaggga cccuccuucc augacuc                                          27

<210> SEQ ID NO 119
<211> LENGTH: 20
<212> TYPE: RNA
<213> ORGANISM: Artificial Sequence
<220> FEATURE:
<223> OTHER INFORMATION: oligonucleotide

<400> SEQUENCE: 119
aucccacuga uucugaauuc                                                  20

<210> SEQ ID NO 120
<211> LENGTH: 22
<212> TYPE: RNA
<213> ORGANISM: Artificial Sequence
<220> FEATURE:
<223> OTHER INFORMATION: oligonucleotide

<400> SEQUENCE: 120
uuggcucugg ccuguccuaa ga                                               22

<210> SEQ ID NO 121
<211> LENGTH: 35
<212> TYPE: RNA
<213> ORGANISM: Artificial Sequence
<220> FEATURE:
<223> OTHER INFORMATION: oligonucleotide

<400> SEQUENCE: 121
aagaccugcu cagcuucuuc cuuagcuucc agcca                                 35
```

<210> SEQ ID NO 122
<211> LENGTH: 23
<212> TYPE: RNA
<213> ORGANISM: Artificial Sequence
<220> FEATURE:
<223> OTHER INFORMATION: oligonucleotide

<400> SEQUENCE: 122
ugcauguucc agucguugug ugg                                              23

<210> SEQ ID NO 123
<211> LENGTH: 25
<212> TYPE: RNA
<213> ORGANISM: Artificial Sequence
<220> FEATURE:
<223> OTHER INFORMATION: oligonucleotide

<400> SEQUENCE: 123
cacuauucca gucaaauagg ucugg                                            25

<210> SEQ ID NO 124
<211> LENGTH: 25
<212> TYPE: RNA
<213> ORGANISM: Artificial Sequence
<220> FEATURE:
<223> OTHER INFORMATION: oligonucleotide

<400> SEQUENCE: 124
auuuaccaac cuucaggauc gagua                                            25

<210> SEQ ID NO 125
<211> LENGTH: 21
<212> TYPE: RNA
<213> ORGANISM: Artificial Sequence
<220> FEATURE:
<223> OTHER INFORMATION: oligonucleotide

<400> SEQUENCE: 125
ggccuaaaac acauacacau a                                                21

<210> SEQ ID NO 126
<211> LENGTH: 20
<212> TYPE: RNA
<213> ORGANISM: Artificial Sequence
<220> FEATURE:
<223> OTHER INFORMATION: oligonucleotide

<400> SEQUENCE: 126
ucagcuucug uuagccacug                                                  20

<210> SEQ ID NO 127
<211> LENGTH: 20
<212> TYPE: RNA
<213> ORGANISM: Artificial Sequence
<220> FEATURE:
<223> OTHER INFORMATION: oligonucleotide

<400> SEQUENCE: 127
uucagcuucu guuagccacu                                                  20

<210> SEQ ID NO 128
<211> LENGTH: 21
<212> TYPE: RNA
<213> ORGANISM: Artificial Sequence
<220> FEATURE:

<223> OTHER INFORMATION: oligonucleotide

<400> SEQUENCE: 128
uucagcuucu guuagccacu g                                            21

<210> SEQ ID NO 129
<211> LENGTH: 21
<212> TYPE: RNA
<213> ORGANISM: Artificial Sequence
<220> FEATURE:
<223> OTHER INFORMATION: oligonucleotide

<400> SEQUENCE: 129
ucagcuucug uuagccacug a                                            21

<210> SEQ ID NO 130
<211> LENGTH: 22
<212> TYPE: RNA
<213> ORGANISM: Artificial Sequence
<220> FEATURE:
<223> OTHER INFORMATION: oligonucleotide

<400> SEQUENCE: 130
uucagcuucu guuagccacu ga                                           22

<210> SEQ ID NO 131
<211> LENGTH: 21
<212> TYPE: RNA
<213> ORGANISM: Artificial Sequence
<220> FEATURE:
<223> OTHER INFORMATION: oligonucleotide

<400> SEQUENCE: 131
ucagcuucug uuagccacug a                                            21

<210> SEQ ID NO 132
<211> LENGTH: 22
<212> TYPE: RNA
<213> ORGANISM: Artificial Sequence
<220> FEATURE:
<223> OTHER INFORMATION: oligonucleotide

<400> SEQUENCE: 132
uucagcuucu guuagccacu ga                                           22

<210> SEQ ID NO 133
<211> LENGTH: 22
<212> TYPE: RNA
<213> ORGANISM: Artificial Sequence
<220> FEATURE:
<223> OTHER INFORMATION: oligonucleotide

<400> SEQUENCE: 133
ucagcuucug uuagccacug au                                           22

<210> SEQ ID NO 134
<211> LENGTH: 23
<212> TYPE: RNA
<213> ORGANISM: Artificial Sequence
<220> FEATURE:
<223> OTHER INFORMATION: oligonucleotide

<400> SEQUENCE: 134
uucagcuucu guuagccacu gau                                          23

<210> SEQ ID NO 135
<211> LENGTH: 23
<212> TYPE: RNA
<213> ORGANISM: Artificial Sequence
<220> FEATURE:
<223> OTHER INFORMATION: oligonucleotide

<400> SEQUENCE: 135
ucagcuucug uuagccacug auu                                               23

<210> SEQ ID NO 136
<211> LENGTH: 24
<212> TYPE: RNA
<213> ORGANISM: Artificial Sequence
<220> FEATURE:
<223> OTHER INFORMATION: oligonucleotide

<400> SEQUENCE: 136
uucagcuucu guuagccacu gauu                                              24

<210> SEQ ID NO 137
<211> LENGTH: 24
<212> TYPE: RNA
<213> ORGANISM: Artificial Sequence
<220> FEATURE:
<223> OTHER INFORMATION: oligonucleotide

<400> SEQUENCE: 137
ucagcuucug uuagccacug auua                                              24

<210> SEQ ID NO 138
<211> LENGTH: 24
<212> TYPE: RNA
<213> ORGANISM: Artificial Sequence
<220> FEATURE:
<223> OTHER INFORMATION: oligonucleotide

<400> SEQUENCE: 138
uucagcuucu guuagccacu gaua                                              24

<210> SEQ ID NO 139
<211> LENGTH: 25
<212> TYPE: RNA
<213> ORGANISM: Artificial Sequence
<220> FEATURE:
<223> OTHER INFORMATION: oligonucleotide

<400> SEQUENCE: 139
ucagcuucug uuagccacug auuaa                                             25

<210> SEQ ID NO 140
<211> LENGTH: 26
<212> TYPE: RNA
<213> ORGANISM: Artificial Sequence
<220> FEATURE:
<223> OTHER INFORMATION: oligonucleotide

<400> SEQUENCE: 140
uucagcuucu guuagccacu gauuaa                                            26

<210> SEQ ID NO 141
<211> LENGTH: 26
<212> TYPE: RNA
<213> ORGANISM: Artificial Sequence
<220> FEATURE:
<223> OTHER INFORMATION: oligonucleotide

```
<400> SEQUENCE: 141
ucagcuucug uuagccacug auuaaa                                          26

<210> SEQ ID NO 142
<211> LENGTH: 27
<212> TYPE: RNA
<213> ORGANISM: Artificial Sequence
<220> FEATURE:
<223> OTHER INFORMATION: oligonucleotide

<400> SEQUENCE: 142
uucagcuucu guuagccacu gauuaaa                                         27

<210> SEQ ID NO 143
<211> LENGTH: 19
<212> TYPE: RNA
<213> ORGANISM: Artificial Sequence
<220> FEATURE:
<223> OTHER INFORMATION: oligonucleotide

<400> SEQUENCE: 143
cagcuucugu uagccacug                                                  19

<210> SEQ ID NO 144
<211> LENGTH: 21
<212> TYPE: RNA
<213> ORGANISM: Artificial Sequence
<220> FEATURE:
<223> OTHER INFORMATION: oligonucleotide

<400> SEQUENCE: 144
cagcuucugu uagccacuga u                                               21

<210> SEQ ID NO 145
<211> LENGTH: 21
<212> TYPE: RNA
<213> ORGANISM: Artificial Sequence
<220> FEATURE:
<223> OTHER INFORMATION: oligonucleotide

<400> SEQUENCE: 145
agcuucuguu agccacugau u                                               21

<210> SEQ ID NO 146
<211> LENGTH: 22
<212> TYPE: RNA
<213> ORGANISM: Artificial Sequence
<220> FEATURE:
<223> OTHER INFORMATION: oligonucleotide

<400> SEQUENCE: 146
cagcuucugu uagccacuga uu                                              22

<210> SEQ ID NO 147
<211> LENGTH: 22
<212> TYPE: RNA
<213> ORGANISM: Artificial Sequence
<220> FEATURE:
<223> OTHER INFORMATION: oligonucleotide

<400> SEQUENCE: 147
agcuucuguu agccacugau ua                                              22

<210> SEQ ID NO 148
<211> LENGTH: 23
```

```
<212> TYPE: RNA
<213> ORGANISM: Artificial Sequence
<220> FEATURE:
<223> OTHER INFORMATION: oligonculeotide

<400> SEQUENCE: 148
cagcuucugu uagccacuga uua                                           23

<210> SEQ ID NO 149
<211> LENGTH: 23
<212> TYPE: RNA
<213> ORGANISM: Artificial Sequence
<220> FEATURE:
<223> OTHER INFORMATION: oligonucleotide

<400> SEQUENCE: 149
agcuucuguu agccacugau uaa                                           23

<210> SEQ ID NO 150
<211> LENGTH: 24
<212> TYPE: RNA
<213> ORGANISM: Artificial Sequence
<220> FEATURE:
<223> OTHER INFORMATION: oligonucleotide

<400> SEQUENCE: 150
cagcuucugu uagccacuga uuaa                                          24

<210> SEQ ID NO 151
<211> LENGTH: 24
<212> TYPE: RNA
<213> ORGANISM: Artificial Sequence
<220> FEATURE:
<223> OTHER INFORMATION: oligonucleotide

<400> SEQUENCE: 151
agcuucuguu agccacugau uaaa                                          24

<210> SEQ ID NO 152
<211> LENGTH: 25
<212> TYPE: RNA
<213> ORGANISM: Artificial Sequence
<220> FEATURE:
<223> OTHER INFORMATION: oligonucleotide

<400> SEQUENCE: 152
cagcuucugu uagccacuga uuaaa                                         25

<210> SEQ ID NO 153
<211> LENGTH: 24
<212> TYPE: RNA
<213> ORGANISM: Artificial Sequence
<220> FEATURE:
<223> OTHER INFORMATION: oligonucleotide

<400> SEQUENCE: 153
agcuucuguu agccacugau uaaa                                          24

<210> SEQ ID NO 154
<211> LENGTH: 20
<212> TYPE: RNA
<213> ORGANISM: Artificial Sequence
<220> FEATURE:
<223> OTHER INFORMATION: oligonucleotide

<400> SEQUENCE: 154
```
agcuucuguu agccacugau                                          20

<210> SEQ ID NO 155
<211> LENGTH: 20
<212> TYPE: RNA
<213> ORGANISM: Artificial Sequence
<220> FEATURE:
<223> OTHER INFORMATION: oligonucleotide

<400> SEQUENCE: 155
gcuucuguua gccacugauu                                          20

<210> SEQ ID NO 156
<211> LENGTH: 21
<212> TYPE: RNA
<213> ORGANISM: Artificial Sequence
<220> FEATURE:
<223> OTHER INFORMATION: oligonucleotide

<400> SEQUENCE: 156
agcuucuguu agccacugau u                                        21

<210> SEQ ID NO 157
<211> LENGTH: 21
<212> TYPE: RNA
<213> ORGANISM: Artificial Sequence
<220> FEATURE:
<223> OTHER INFORMATION: oligonucleotide

<400> SEQUENCE: 157
gcuucuguua gccacugauu a                                        21

<210> SEQ ID NO 158
<211> LENGTH: 22
<212> TYPE: RNA
<213> ORGANISM: Artificial Sequence
<220> FEATURE:
<223> OTHER INFORMATION: oligonculeotide

<400> SEQUENCE: 158
agcuucuguu agccacugau ua                                       22

<210> SEQ ID NO 159
<211> LENGTH: 22
<212> TYPE: RNA
<213> ORGANISM: Artificial Sequence
<220> FEATURE:
<223> OTHER INFORMATION: oligonucleotide

<400> SEQUENCE: 159
gcuucuguua gccacugauu aa                                       22

<210> SEQ ID NO 160
<211> LENGTH: 23
<212> TYPE: RNA
<213> ORGANISM: Artificial Sequence
<220> FEATURE:
<223> OTHER INFORMATION: oligonucleotide

<400> SEQUENCE: 160
agcuucuguu agccacugau uaa                                      23

<210> SEQ ID NO 161
<211> LENGTH: 23
<212> TYPE: RNA
<213> ORGANISM: Artificial Sequence

```
<220> FEATURE:
<223> OTHER INFORMATION: oligonucleotide

<400> SEQUENCE: 161
gcuucuguua gccacugauu aaa                                              23

<210> SEQ ID NO 162
<211> LENGTH: 24
<212> TYPE: RNA
<213> ORGANISM: Artificial Sequence
<220> FEATURE:
<223> OTHER INFORMATION: oligonucleotide

<400> SEQUENCE: 162
agcuucuguu agccacugau uaaa                                             24

<210> SEQ ID NO 163
<211> LENGTH: 23
<212> TYPE: RNA
<213> ORGANISM: Artificial Sequence
<220> FEATURE:
<223> OTHER INFORMATION: oligonucleotide

<400> SEQUENCE: 163
gcuucuguua gccacugauu aaa                                              23

<210> SEQ ID NO 164
<211> LENGTH: 23
<212> TYPE: RNA
<213> ORGANISM: Artificial Sequence
<220> FEATURE:
<223> OTHER INFORMATION: oligonucleotide

<400> SEQUENCE: 164
ccauuuguau uuagcauguu ccc                                              23

<210> SEQ ID NO 165
<211> LENGTH: 20
<212> TYPE: RNA
<213> ORGANISM: Artificial Sequence
<220> FEATURE:
<223> OTHER INFORMATION: oligonucleotide

<400> SEQUENCE: 165
agauaccauu uguauuuagc                                                  20

<210> SEQ ID NO 166
<211> LENGTH: 19
<212> TYPE: RNA
<213> ORGANISM: Artificial Sequence
<220> FEATURE:
<223> OTHER INFORMATION: oligonucleotide

<400> SEQUENCE: 166
gccauuucuc aacagaucu                                                   19

<210> SEQ ID NO 167
<211> LENGTH: 23
<212> TYPE: RNA
<213> ORGANISM: Artificial Sequence
<220> FEATURE:
<223> OTHER INFORMATION: oligonucleotide

<400> SEQUENCE: 167
gccauuucuc aacagaucug uca                                              23
```

```
<210> SEQ ID NO 168
<211> LENGTH: 23
<212> TYPE: RNA
<213> ORGANISM: Artificial Sequence
<220> FEATURE:
<223> OTHER INFORMATION: oligonucleotide

<400> SEQUENCE: 168
auucucagga auugugucu uuc                                              23

<210> SEQ ID NO 169
<211> LENGTH: 21
<212> TYPE: RNA
<213> ORGANISM: Artificial Sequence
<220> FEATURE:
<223> OTHER INFORMATION: oligonucleotide

<400> SEQUENCE: 169
ucucaggaau uugugucuuu c                                               21

<210> SEQ ID NO 170
<211> LENGTH: 18
<212> TYPE: RNA
<213> ORGANISM: Artificial Sequence
<220> FEATURE:
<223> OTHER INFORMATION: oligonucleotide

<400> SEQUENCE: 170
guucagcuuc uguuagcc                                                   18

<210> SEQ ID NO 171
<211> LENGTH: 21
<212> TYPE: RNA
<213> ORGANISM: Artificial Sequence
<220> FEATURE:
<223> OTHER INFORMATION: oligonucleotide

<400> SEQUENCE: 171
cugauuaaau aucuuuauau c                                               21

<210> SEQ ID NO 172
<211> LENGTH: 18
<212> TYPE: RNA
<213> ORGANISM: Artificial Sequence
<220> FEATURE:
<223> OTHER INFORMATION: oligonucleotide

<400> SEQUENCE: 172
gccgccauuu cucaacag                                                   18

<210> SEQ ID NO 173
<211> LENGTH: 18
<212> TYPE: RNA
<213> ORGANISM: Artificial Sequence
<220> FEATURE:
<223> OTHER INFORMATION: oligonucleotide

<400> SEQUENCE: 173
guauuuagca uguuccca                                                   18

<210> SEQ ID NO 174
<211> LENGTH: 18
<212> TYPE: RNA
<213> ORGANISM: Artificial Sequence
<220> FEATURE:
<223> OTHER INFORMATION: oligonucleotide
```

<400> SEQUENCE: 174
caggaauuug ugucuuuc                                              18

<210> SEQ ID NO 175
<211> LENGTH: 25
<212> TYPE: RNA
<213> ORGANISM: Artificial Sequence
<220> FEATURE:
<223> OTHER INFORMATION: oligonucleotide

<400> SEQUENCE: 175 gcuuucuuu uaguugcugc ucuuu                                       25

<210> SEQ ID NO 176
<211> LENGTH: 25
<212> TYPE: RNA
<213> ORGANISM: Artificial Sequence
<220> FEATURE:
<223> OTHER INFORMATION: oligonucleotide

<400> SEQUENCE: 176 cuuucuuuu aguugcugcu cuuuu                                       25

<210> SEQ ID NO 177
<211> LENGTH: 25
<212> TYPE: RNA
<213> ORGANISM: Artificial Sequence
<220> FEATURE:
<223> OTHER INFORMATION: oligonucleotide

<400> SEQUENCE: 177
uuuucuuuua guugcugcuc uuuuc                                      25

<210> SEQ ID NO 178
<211> LENGTH: 25
<212> TYPE: RNA
<213> ORGANISM: Artificial Sequence
<220> FEATURE:
<223> OTHER INFORMATION: oligonucleotide

<400> SEQUENCE: 178
uuucuuuuag uugcugcucu uuucc                                      25

<210> SEQ ID NO 179
<211> LENGTH: 25
<212> TYPE: RNA
<213> ORGANISM: Artificial Sequence
<220> FEATURE:
<223> OTHER INFORMATION: oligonucleotide

<400> SEQUENCE: 179
uucuuuuagu ugcugcucuu uucca                                      25

<210> SEQ ID NO 180
<211> LENGTH: 25
<212> TYPE: RNA
<213> ORGANISM: Artificial Sequence
<220> FEATURE:
<223> OTHER INFORMATION: oligonucleotide

<400> SEQUENCE: 180
ucuuuuaguu gcugcucuuu uccag                                      25

<210> SEQ ID NO 181

```
<211> LENGTH: 25
<212> TYPE: RNA
<213> ORGANISM: Artificial Sequence
<220> FEATURE:
<223> OTHER INFORMATION: oligonucleotide

<400> SEQUENCE: 181
cuuuuaguug cugcucuuuu ccagg                                        25

<210> SEQ ID NO 182
<211> LENGTH: 25
<212> TYPE: RNA
<213> ORGANISM: Artificial Sequence
<220> FEATURE:
<223> OTHER INFORMATION: oligonucleotide

<400> SEQUENCE: 182
uuuuaguugc ugcucuuuuc caggu                                        25

<210> SEQ ID NO 183
<211> LENGTH: 25
<212> TYPE: RNA
<213> ORGANISM: Artificial Sequence
<220> FEATURE:
<223> OTHER INFORMATION: oligonucleotide

<400> SEQUENCE: 183
uuuaguugcu gcucuuuucc agguu                                        25

<210> SEQ ID NO 184
<211> LENGTH: 25
<212> TYPE: RNA
<213> ORGANISM: Artificial Sequence
<220> FEATURE:
<223> OTHER INFORMATION: oligonucleotide

<400> SEQUENCE: 184
uuaguugcug cucuuuucca gguuc                                        25

<210> SEQ ID NO 185
<211> LENGTH: 25
<212> TYPE: RNA
<213> ORGANISM: Artificial Sequence
<220> FEATURE:
<223> OTHER INFORMATION: oligonucleotide

<400> SEQUENCE: 185
uaguugcugc ucuuuuccag guuca                                        25

<210> SEQ ID NO 186
<211> LENGTH: 25
<212> TYPE: RNA
<213> ORGANISM: Artificial Sequence
<220> FEATURE:
<223> OTHER INFORMATION: oligonucleotide

<400> SEQUENCE: 186
aguugcugcu cuuuuccagg uucaa                                        25

<210> SEQ ID NO 187
<211> LENGTH: 25
<212> TYPE: RNA
<213> ORGANISM: Artificial Sequence
<220> FEATURE:
<223> OTHER INFORMATION: oligonucleotide

<400> SEQUENCE: 187
```
guugcugcuc uuuuccaggu ucaag                                        25

<210> SEQ ID NO 188
<211> LENGTH: 25
<212> TYPE: RNA
<213> ORGANISM: Artificial Sequence
<220> FEATURE:
<223> OTHER INFORMATION: oligonucleotide

<400> SEQUENCE: 188
uugcugcucu uuuccagguu caagu                                        25

<210> SEQ ID NO 189
<211> LENGTH: 25
<212> TYPE: RNA
<213> ORGANISM: Artificial Sequence
<220> FEATURE:
<223> OTHER INFORMATION: oligonucleotide

<400> SEQUENCE: 189
ugcugcucuu uuccagguuc aagug                                        25

<210> SEQ ID NO 190
<211> LENGTH: 25
<212> TYPE: RNA
<213> ORGANISM: Artificial Sequence
<220> FEATURE:
<223> OTHER INFORMATION: oligonucleotide

<400> SEQUENCE: 190
gcugcucuuu uccagguuca agugg                                        25

<210> SEQ ID NO 191
<211> LENGTH: 25
<212> TYPE: RNA
<213> ORGANISM: Artificial Sequence
<220> FEATURE:
<223> OTHER INFORMATION: oligonucleotide

<400> SEQUENCE: 191
cugcucuuuu ccagguucaa guggg                                        25

<210> SEQ ID NO 192
<211> LENGTH: 25
<212> TYPE: RNA
<213> ORGANISM: Artificial Sequence
<220> FEATURE:
<223> OTHER INFORMATION: oligonucleotide

<400> SEQUENCE: 192
ugcucuuuuc cagguucaag uggga                                        25

<210> SEQ ID NO 193
<211> LENGTH: 25
<212> TYPE: RNA
<213> ORGANISM: Artificial Sequence
<220> FEATURE:
<223> OTHER INFORMATION: oligonucleotide

<400> SEQUENCE: 193
gcucuuuucc agguucaagu gggac                                        25

<210> SEQ ID NO 194
<211> LENGTH: 25
<212> TYPE: RNA

```
<213> ORGANISM: Artificial Sequence
<220> FEATURE:
<223> OTHER INFORMATION: oligonucleotide

<400> SEQUENCE: 194
cucuuuucca gguucaagug ggaua                                              25

<210> SEQ ID NO 195
<211> LENGTH: 25
<212> TYPE: RNA
<213> ORGANISM: Artificial Sequence
<220> FEATURE:
<223> OTHER INFORMATION: oligonucleotide

<400> SEQUENCE: 195
ucuuuuccag guucaagugg gauac                                              25

<210> SEQ ID NO 196
<211> LENGTH: 25
<212> TYPE: RNA
<213> ORGANISM: Artificial Sequence
<220> FEATURE:
<223> OTHER INFORMATION: oligonucleotide

<400> SEQUENCE: 196
cuuuuccagg uucaagugggg auacu                                             25

<210> SEQ ID NO 197
<211> LENGTH: 25
<212> TYPE: RNA
<213> ORGANISM: Artificial Sequence
<220> FEATURE:
<223> OTHER INFORMATION: oligonucleotide

<400> SEQUENCE: 197
uuuuccaggu ucaaguggga uacua                                              25

<210> SEQ ID NO 198
<211> LENGTH: 25
<212> TYPE: RNA
<213> ORGANISM: Artificial Sequence
<220> FEATURE:
<223> OTHER INFORMATION: oligonucleotide

<400> SEQUENCE: 198
uuuccagguu caagugggau acuag                                              25

<210> SEQ ID NO 199
<211> LENGTH: 25
<212> TYPE: RNA
<213> ORGANISM: Artificial Sequence
<220> FEATURE:
<223> OTHER INFORMATION: oligonucleotide

<400> SEQUENCE: 199
uuccagguuc aagugggaua cuagc                                              25

<210> SEQ ID NO 200
<211> LENGTH: 25
<212> TYPE: RNA
<213> ORGANISM: Artificial Sequence
<220> FEATURE:
<223> OTHER INFORMATION: oligonucleotide

<400> SEQUENCE: 200
uccagguuca agugggauac uagca                                              25
```

<210> SEQ ID NO 201
<211> LENGTH: 25
<212> TYPE: RNA
<213> ORGANISM: Artificial Sequence
<220> FEATURE:
<223> OTHER INFORMATION: oligonucleotide

<400> SEQUENCE: 201
ccagguucaa gugggauacu agcaa                                           25

<210> SEQ ID NO 202
<211> LENGTH: 25
<212> TYPE: RNA
<213> ORGANISM: Artificial Sequence
<220> FEATURE:
<223> OTHER INFORMATION: oligonucleotide

<400> SEQUENCE: 202
cagguucaag ugggauacua gcaau                                           25

<210> SEQ ID NO 203
<211> LENGTH: 25
<212> TYPE: RNA
<213> ORGANISM: Artificial Sequence
<220> FEATURE:
<223> OTHER INFORMATION: oligonucleotide

<400> SEQUENCE: 203
agguucaagu gggauacuag caaug                                           25

<210> SEQ ID NO 204
<211> LENGTH: 25
<212> TYPE: RNA
<213> ORGANISM: Artificial Sequence
<220> FEATURE:
<223> OTHER INFORMATION: oligonucleotide

<400> SEQUENCE: 204
gguucaagug ggauacuagc aaugu                                           25

<210> SEQ ID NO 205
<211> LENGTH: 25
<212> TYPE: RNA
<213> ORGANISM: Artificial Sequence
<220> FEATURE:
<223> OTHER INFORMATION: oligonucleotide

<400> SEQUENCE: 205
guucaagugg gauacuagca auguu                                           25

<210> SEQ ID NO 206
<211> LENGTH: 25
<212> TYPE: RNA
<213> ORGANISM: Artificial Sequence
<220> FEATURE:
<223> OTHER INFORMATION: oligonucleotide

<400> SEQUENCE: 206
uucaaguggg auacuagcaa uguua                                           25

<210> SEQ ID NO 207
<211> LENGTH: 25
<212> TYPE: RNA
<213> ORGANISM: Artificial Sequence
<220> FEATURE:

<223> OTHER INFORMATION: oligonucleotide

<400> SEQUENCE: 207
ucaaguggga uacuagcaau guuau                                              25

<210> SEQ ID NO 208
<211> LENGTH: 25
<212> TYPE: RNA
<213> ORGANISM: Artificial Sequence
<220> FEATURE:
<223> OTHER INFORMATION: oligonucleotide

<400> SEQUENCE: 208
caagugggau acuagcaaug uuauc                                              25

<210> SEQ ID NO 209
<211> LENGTH: 25
<212> TYPE: RNA
<213> ORGANISM: Artificial Sequence
<220> FEATURE:
<223> OTHER INFORMATION: oligonucleotide

<400> SEQUENCE: 209
aagugggaua cuagcaaugu uaucu                                              25

<210> SEQ ID NO 210
<211> LENGTH: 25
<212> TYPE: RNA
<213> ORGANISM: Artificial Sequence
<220> FEATURE:
<223> OTHER INFORMATION: oligonucleotide

<400> SEQUENCE: 210
agugggauac uagcaauguu aucug                                              25

<210> SEQ ID NO 211
<211> LENGTH: 25
<212> TYPE: RNA
<213> ORGANISM: Artificial Sequence
<220> FEATURE:
<223> OTHER INFORMATION: oligonucleotide

<400> SEQUENCE: 211
gugggauacu agcaauguua ucugc                                              25

<210> SEQ ID NO 212
<211> LENGTH: 25
<212> TYPE: RNA
<213> ORGANISM: Artificial Sequence
<220> FEATURE:
<223> OTHER INFORMATION: oligonucleotide

<400> SEQUENCE: 212
ugggauacua gcaauguuau cugcu                                              25

<210> SEQ ID NO 213
<211> LENGTH: 25
<212> TYPE: RNA
<213> ORGANISM: Artificial Sequence
<220> FEATURE:
<223> OTHER INFORMATION: oligonucleotide

<400> SEQUENCE: 213
gggauacuag caauguuauc ugcuu                                              25

```
<210> SEQ ID NO 214
<211> LENGTH: 25
<212> TYPE: RNA
<213> ORGANISM: Artificial Sequence
<220> FEATURE:
<223> OTHER INFORMATION: oligonucleotide

<400> SEQUENCE: 214
ggauacuagc aauguuaucu gcuuc                                          25

<210> SEQ ID NO 215
<211> LENGTH: 25
<212> TYPE: RNA
<213> ORGANISM: Artificial Sequence
<220> FEATURE:
<223> OTHER INFORMATION: oligonucleotide

<400> SEQUENCE: 215
gauacuagca auguuaucug cuucc                                          25

<210> SEQ ID NO 216
<211> LENGTH: 25
<212> TYPE: RNA
<213> ORGANISM: Artificial Sequence
<220> FEATURE:
<223> OTHER INFORMATION: oligonucleotide

<400> SEQUENCE: 216
auacuagcaa uguuaucugc uuccu                                          25

<210> SEQ ID NO 217
<211> LENGTH: 25
<212> TYPE: RNA
<213> ORGANISM: Artificial Sequence
<220> FEATURE:
<223> OTHER INFORMATION: oligonucleotide

<400> SEQUENCE: 217
uacuagcaau guuaucugcu uccuc                                          25

<210> SEQ ID NO 218
<211> LENGTH: 25
<212> TYPE: RNA
<213> ORGANISM: Artificial Sequence
<220> FEATURE:
<223> OTHER INFORMATION: oligonucleotide

<400> SEQUENCE: 218
acuagcaaug uuaucugcuu ccucc                                          25

<210> SEQ ID NO 219
<211> LENGTH: 25
<212> TYPE: RNA
<213> ORGANISM: Artificial Sequence
<220> FEATURE:
<223> OTHER INFORMATION: oligonucleotide

<400> SEQUENCE: 219
cuagcaaugu uaucugcuuc cucca                                          25

<210> SEQ ID NO 220
<211> LENGTH: 25
<212> TYPE: RNA
<213> ORGANISM: Artificial Sequence
<220> FEATURE:
<223> OTHER INFORMATION: oligonucleotide
```

```
<400> SEQUENCE: 220
uagcaauguu aucugcuucc uccaa                                              25

<210> SEQ ID NO 221
<211> LENGTH: 25
<212> TYPE: RNA
<213> ORGANISM: Artificial Sequence
<220> FEATURE:
<223> OTHER INFORMATION: oligonucleotide

<400> SEQUENCE: 221
agcaauguua ucugcuuccu ccaac                                              25

<210> SEQ ID NO 222
<211> LENGTH: 25
<212> TYPE: RNA
<213> ORGANISM: Artificial Sequence
<220> FEATURE:
<223> OTHER INFORMATION: oligonucleotide

<400> SEQUENCE: 222
gcaauguuau cugcuuccuc caacc                                              25

<210> SEQ ID NO 223
<211> LENGTH: 25
<212> TYPE: RNA
<213> ORGANISM: Artificial Sequence
<220> FEATURE:
<223> OTHER INFORMATION: oligonucleotide

<400> SEQUENCE: 223
caauguuauc ugcuuccucc aacca                                              25

<210> SEQ ID NO 224
<211> LENGTH: 25
<212> TYPE: RNA
<213> ORGANISM: Artificial Sequence
<220> FEATURE:
<223> OTHER INFORMATION: oligonucleotide

<400> SEQUENCE: 224
aauguuaucu gcuuccucca accau                                              25

<210> SEQ ID NO 225
<211> LENGTH: 25
<212> TYPE: RNA
<213> ORGANISM: Artificial Sequence
<220> FEATURE:
<223> OTHER INFORMATION: oligonucleotide

<400> SEQUENCE: 225
auguuaucug cuuccuccaa ccaua                                              25

<210> SEQ ID NO 226
<211> LENGTH: 25
<212> TYPE: RNA
<213> ORGANISM: Artificial Sequence
<220> FEATURE:
<223> OTHER INFORMATION: oligonucleotide

<400> SEQUENCE: 226
uguuaucugc uuccuccaac cauaa                                              25

<210> SEQ ID NO 227
<211> LENGTH: 25
```

```
<212> TYPE: RNA
<213> ORGANISM: Artificial Sequence
<220> FEATURE:
<223> OTHER INFORMATION: oligonucleotide

<400> SEQUENCE: 227
guuaucugcu uccuccaacc auaaa                                            25

<210> SEQ ID NO 228
<211> LENGTH: 19
<212> TYPE: RNA
<213> ORGANISM: Artificial Sequence
<220> FEATURE:
<223> OTHER INFORMATION: oligonucleotide

<400> SEQUENCE: 228
gcugcucuuu uccagguuc                                                   19

<210> SEQ ID NO 229
<211> LENGTH: 20
<212> TYPE: RNA
<213> ORGANISM: Artificial Sequence
<220> FEATURE:
<223> OTHER INFORMATION: oligonucleotide

<400> SEQUENCE: 229
ucuuuuccag guucaagugg                                                  20

<210> SEQ ID NO 230
<211> LENGTH: 19
<212> TYPE: RNA
<213> ORGANISM: Artificial Sequence
<220> FEATURE:
<223> OTHER INFORMATION: oligonucleotide

<400> SEQUENCE: 230
agguucaagu gggauacua                                                   19

<210> SEQ ID NO 231
<211> LENGTH: 21
<212> TYPE: RNA
<213> ORGANISM: Artificial Sequence
<220> FEATURE:
<223> OTHER INFORMATION: oligonucleotide

<400> SEQUENCE: 231
caauuuuucc cacucaguau u                                                21

<210> SEQ ID NO 232
<211> LENGTH: 19
<212> TYPE: RNA
<213> ORGANISM: Artificial Sequence
<220> FEATURE:
<223> OTHER INFORMATION: oligonucleotide

<400> SEQUENCE: 232
uugaaguucc uggagucuu                                                   19

<210> SEQ ID NO 233
<211> LENGTH: 22
<212> TYPE: RNA
<213> ORGANISM: Artificial Sequence
<220> FEATURE:
<223> OTHER INFORMATION: oligonucleotide

<400> SEQUENCE: 233
```

```
uccucaggag gcagcucuaa au                                             22

<210> SEQ ID NO 234
<211> LENGTH: 26
<212> TYPE: RNA
<213> ORGANISM: Artificial Sequence
<220> FEATURE:
<223> OTHER INFORMATION: oligonucleotide

<400> SEQUENCE: 234
gcgcugguca caaaauccug uugaac                                         26

<210> SEQ ID NO 235
<211> LENGTH: 27
<212> TYPE: RNA
<213> ORGANISM: Artificial Sequence
<220> FEATURE:
<223> OTHER INFORMATION: oligonucleotide

<400> SEQUENCE: 235
cacuugcuug aaaaggucua caaagga                                        27

<210> SEQ ID NO 236
<211> LENGTH: 26
<212> TYPE: RNA
<213> ORGANISM: Artificial Sequence
<220> FEATURE:
<223> OTHER INFORMATION: oligonucleotide

<400> SEQUENCE: 236
ggugaauaac uuacaaauuu ggaagc                                         26
```